(12) United States Patent
Cha et al.

(10) Patent No.: US 6,297,370 B1
(45) Date of Patent: Oct. 2, 2001

(54) HCV GENOMIC SEQUENCES FOR DIAGNOSTICS AND THERAPEUTICS

(75) Inventors: Tai-An Cha, San Ramon; Eileen Beall, Walnut Creek; Bruce Irvine, Concord; Janice Kolberg, Hercules; Michael S. Urdea, Alamo, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/441,970

(22) Filed: May 16, 1995

Related U.S. Application Data

(62) Division of application No. 08/221,653, filed on Apr. 1, 1994, now Pat. No. 6,190,864, which is a continuation of application No. 07/881,528, filed on May 8, 1992, now abandoned, which is a continuation-in-part of application No. 07/697,326, filed on May 8, 1991, now abandoned.

(51) Int. Cl.$^7$ .......................... C07H 21/04; C07H 21/02; C12Q 1/68; C12N 15/00

(52) U.S. Cl. ........................... 536/24.3; 536/23.1; 435/6; 935/76; 935/77; 935/78

(58) Field of Search .................. 435/6; 536/22.1, 536/23.1, 24.3, 24.32

(56) References Cited

U.S. PATENT DOCUMENTS

| | | | |
|---|---|---|---|
| 4,341,761 | 7/1982 | Garfield et al. | 424/85 |
| 4,399,121 | 8/1983 | Albarella et al. | 260/112.5 |
| 4,427,783 | 1/1984 | Newman et al. | 436/542 |
| 4,444,887 | 4/1984 | Hoffman | 435/240 |
| 4,458,066 | 7/1984 | Caruthers et al. | 536/27 |
| 4,466,917 | 8/1984 | Nussenzweig et al. | 260/112 |
| 4,472,500 | 9/1984 | Milstein et al. | 435/68 |
| 4,491,632 | 1/1985 | Wands et al. | 435/240 |
| 4,493,890 | 1/1985 | Morris | 435/7 |
| 4,683,202 | * 7/1987 | Mullis | 435/91 |
| 4,868,105 | 9/1989 | Urdea et al. | 435/6 |
| 5,055,393 | * 10/1991 | Kwoh et al. | 435/6 |
| 5,107,065 | * 4/1992 | Shewmaker | 800/205 |
| 5,147,777 | * 9/1992 | Sutton et al. | 435/5 |
| 5,175,147 | * 12/1992 | Folkman et al. | 514/12 |
| 5,175,268 | * 12/1992 | Iwasa et al. | 536/27 |
| 5,225,546 | * 7/1993 | Dryja et al. | 536/24.31 |
| 5,258,283 | * 11/1993 | Frazier et al. | 435/6 |
| 5,264,558 | * 11/1993 | Kim et al. | 530/402 |
| 5,387,505 | * 2/1995 | Wu | 435/6 |
| 5,424,184 | * 6/1995 | Santemaria e al. | 435/6 |
| 5,457,089 | * 10/1995 | Fibi et al. | 514/8 |
| 5,484,886 | * 1/1996 | Fong et al. | 530/350 |
| 5,688,666 | * 11/1997 | Bass et al. | 435/69.4 |
| 5,747,267 | * 5/1998 | Mulvihill et al. | 435/7.21 |

FOREIGN PATENT DOCUMENTS

WO11547 * 11/1989 (WO).

OTHER PUBLICATIONS

Enomoto et al., Biochem. and Biophys. Research Communication 170(3): 1021–1025 (1990).*
Matthews et al., Analytical Biochemistry 169: 1–25 (1989).*
Takamizawa et al., J of Virology 65(3): 1105–1113 (1991).*
Okamoto et al., Japan. J of Exp. Med. 60(3): 167–177 (1990).*
Ogata et al. PNAS 88:3392–3396 (1991).*
The Pharmacia Catalog pp. 18–25 (1988 Edition).*
Kato et al., PNAS 87: 9524–9528 (1990).*
Sommer et al., Nucleic Acids Research 17(16): 6749 (1989).*
Yamane et al., Nucleic Acids Research, Symposium Series No. 20: pp. 91–92 (Sep. 1988).*
Saiki et al., Science 230: 1350–1354 (1985).*
Takeuchi et al., Nucleic Acids Research 18 (15) : 4626 (Aug. 1990).*
Weiner et al., Virology 180 : 842–848 (Feb. 1991).*
*Barr et al. (1986), Biotechniques 4:428.
*Beaucage et al. (1981), Tetrahedron Letters 22:1859.
*Borstein (1979), Gene 8;17.
*Brinton, M. A. (1986), The Viruses: the Togavirodae and Flaviviridae (Series Eds. Fraenkel–Conrat and Wagner, vol. eds. Schlesinger and Schlesinger, Plenum Press), pp. 327–374.
*Broach (1981), Molecular Biology of the Yeast Saccharoymces, vol. 1, p. 445, Cold Sping Harbor Press.
*Broach et al. (1983), Meth. Enz. 101:307.
*Brown et al. (1979), Methods in Enzymology 68: 109.
*Byrne et al. (1988), Nucleic Acids Res. 16:4165.
*Castle et al. (1986), Virology 119:10.
*Chang et al. (1977), Nature 198:1056.
*Chirqwin et al. (1979), Biochemistry 18:5494.
*Choo et al. (1989), Science 244:359.
*Chomczynski and Sacchi (1987), Analytical Biochemistry 162:156.
*Clewell et al. (1969), Proc. Natl. Acad. Sci. USA 62:1159.
*Clewell (1972), J. Bacteriol. 110:667.
*Cohen (1972), Proc. Natl. Acad. Sci. USA 69:2110.
*Cousens et al. (1987), Gene 61:265.
*De Boer et al. (1983), Proc. Nat., Acad. Sci. USA 292:128.
*Dreesman et al. (1985), J. Infect. Disease 151:761.
*Feinstone et al., (1981), J. Infect. Disease 144:588.
*Feinstone et al. (1983), Infection and Immunology 41:816.
*Feinstone, S.M. & Hoofnagle, J. H. (1984), New Engl J Med 311–185.
*Fields & Knipe (1986), Fundamentel Virology (Raven Press, N.Y.).

(List continued on next page.)

Primary Examiner—Ethan Whisenant
(74) Attorney, Agent, or Firm—Gwilym J. O. Attwell; Alisa A. Harbin; Robert P. Blackburn

(57) ABSTRACT

The present application features nucleic acid, peptide and antibody compositions relating to genotypes of hepatitis C virus and methods of using such compositions for diagnostic and therapeutic purposes.

11 Claims, 21 Drawing Sheets

OTHER PUBLICATIONS

Figure 1:
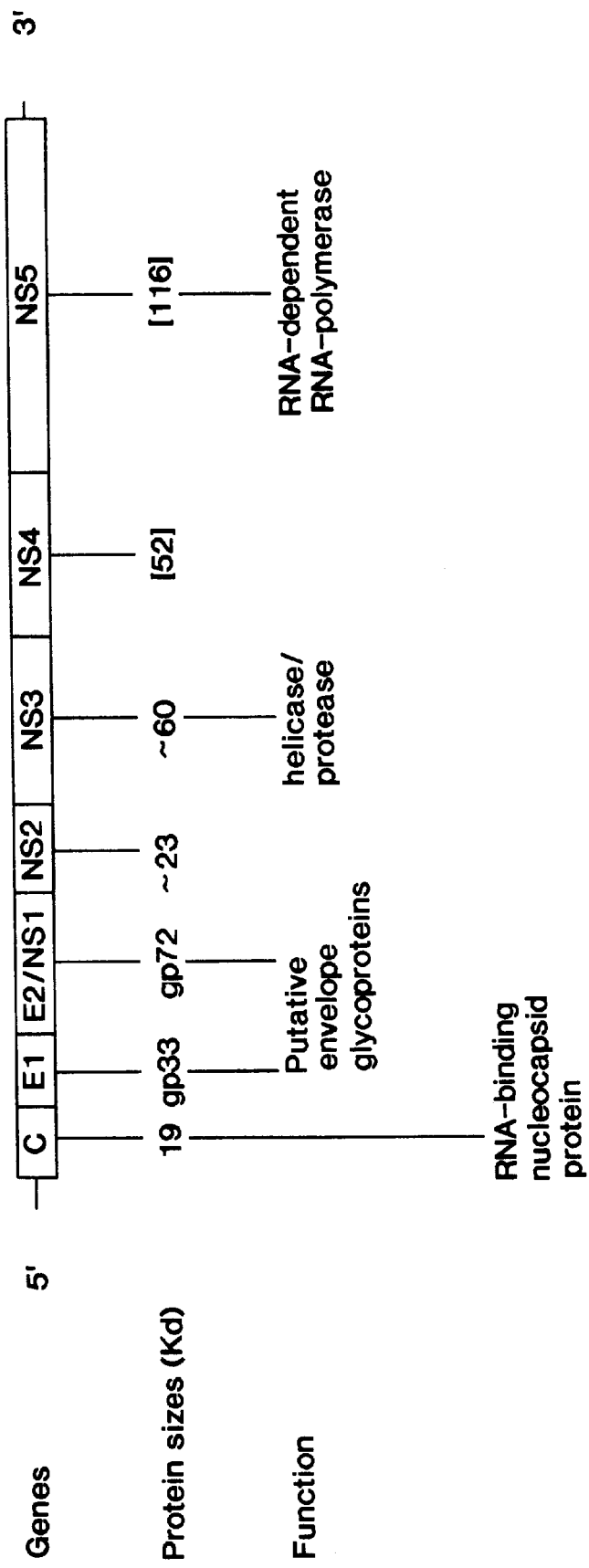

*Fiers et al., (1978), Nature 273:113.
*Gerety, R.J. et al., "Viral Hepatitis and Liver Disease,"(Vyas B. N., Dienstag, J. L., and Hoofnagle, J. H., eds, Grune and Stratton, Inc., 1984) pp. 23–47.
*Goeddel et al., (1980), Nucleic Acids Res. 8:4057.
*Graham and Van der Eb (1978), Virology 52:546.
*Grunstein and Hogness (1975), Proc. Natl. Acad. Sci. USA 73:3961.
*Grych et al., (1985), Nature 316:74.
*Gubler and Hoffman (1983), Gene 25:263.
*Hahn et al. (1988), Virology 162:167.
*Han (1987), Biochemistry 26:1617.
*Hammerling et al. (1981), Monoclonal Antibodies and T–Cell Hybridomas.
*Hess et al. (1968), J. Adv. Enzyme Reg 7:149.
*Hinnen et al. (1978), Proc. Natl. Acad. Sci. 75:1929.
*Hitzeman et al. (1980), J. Biol. Chem. 255:2073.
*Holland et al. (1978), Biochemistry 17:4900.
*Holland (1981), J. Biol. Chem. 256:1385.
*Houghton et al. (1981), Nucleic Acids Res. 9:247.
*Huynh, T. V. et al. (1985), *DNA Cloning Techniques: A Practical Approach*, (D. Glover, Ed., IRL Press, Oxford, U.K.) pp. 49–78.
*Immun. Rev. (1982) 62:185.
*Iwarson (1987), British Medical J. 295:946.
*Kennett et al. (1980) Monoclonal Antibodies.
*Kuo et al. (1989), Science 244:362.
*Kyte and Doolottle (1982), J. Mol. Biol. 157:105–132.
*Landegren et al. (1988), Science 242:229.
*Maniatis, T. et al. (1982) *Molecular Cloning; A Laboratory Manual* (Cold Spring Harbor Press, Cold Spring Harbor, N.Y.).
*Mattews and Kricka (1988), Analytical Biochemistry 169:1.
**Methods in Enzymology* (Academic Press).
*Mittlin (1989), Clinical Chem. 35:1819.
*Laemmli (1970), Nature 227, 680.
*Lee et al. (1988), Science 239:1288.
*Loh et al. (1989), Science 243:217.
*Mackow et al. (1987), Virology 159:217.
*Mayer and Walker, eds. (1987), *Immunochemical Methods in Cell and Molecular Biology* (Academic Press, London).
*Mayumi et al. (1990), Japanese J. Exp. Med. 60:167.
*Maxam et al. (1980), Methods in Enzymology 65:499.
*MacNamara et al. (1984), Science 226:1325.
*Messing et al. (1981), Nucleic Acids Res. 9:309.
*Messing (1983), Methods in Enzymology 101–20–37.
*Michelle et al., Int. Symposium on Viral Hepatitis.
*Monath (1986) in The Viruses: The Togaviridae and Flaviviridae Series eds. Fraenkel–Conrat and Wagner, vol. eds. Schlesinger and Schlesinger, (Plenum Press), pp. 375–440.
*Murakawa et al. (1988), DNA 7:287.
*Nagahuma et al. (1984), Anal. Biochem. 141:74.
*Narang et al. (1979), Methods in Enzymology 68:90.
*Neurath et al. (1984), Science 224:392.
*Nisonoff et al. (1981), Clin. Immunol. Immunopathol. 21:397–406.
*Overby, L. R. (1985), Curr. Hepatol. 5:49.
*Overby, L. R. (1986), Curr. Hepatol. 7:35.
*Peleg (1969), Nature 221:193.
*Pfefferkorn and Shapiro (1974), in Comprehensive Virology, vol. 2 (Fraenkel–Conrat & Wagner, eds., Planum, N.Y.) pp. 171–230.

*Prince, A. M. (1983), Annu. Rev. Microbiol. 37:217.

*Rice et al. (1985), Science 229:726.

*Rice et al. (1986) in the Viruses: The Togaviridae and Falviviridae (Series eds. Fraenkel–Conrat and Wagner, vol. eds. Schlesinger and Schlesinger, Plenum Press), pp. 279–328.

*Roehrig (1986) in The Viruses: The Togaviridae and Flaviridae (Series eds. Fraenkel–Congrat and Wagner, vol. eds. Schlesinger and Schlesinger. Plenum Press).

*Rosenberg et al. (1984), Nature 312:7.

*Sadler et al. (1980), Gene 8, 279.

*Saiki et al. (1985), Science 230:1350.

*Saiki et al. (1986), Nature 324:163.

*Saiki et al. (1988), Science 239–487.

*Sanger et al. (1977), Proc. Natl. Acad. Sci. USA 74:5463.

*Scharf et al. (1986) et al. (1986), Science 233:1076.

*Schlesinger et al. (1986), J. Virol. 60:1153.

*Schreier, M. et al. (1980) Hybridoma Techniques.

*Scopes (1984), Protein Purification, Principles and Practice, Second Edition, (Speinger–Verlag, N.Y.).

*Shimatake et al. (1981), Nature 292:128.

*Shigekawa and Dower (1988), BioTechniques 6:742.

*Steimer et al. (1986), J. Virol. 58:9.

*Stollar (1980), in The Togaviruses (R. W. Schlesinger, eds., Academic Press, N.Y.), pp. 584–622.

*Sumiyoshi et al. (1987), Virology 161:497.

*Taylor et al. (1976), Biochem. Biophys. Acta 442:324.

*Towbin et al. (1979), Proc. Natl. Acad. Sci. USA 76, 4350.

*Tsu and Herzenberg (1980), in *Selected Methods in Cellular Immunology* (W. H. Freeman and Co.) pp. 373–391.

*Vytdehaag et al. (1985), J. Immunol. 134:1225.

*Valenzuela, P., et al. (1982), Nature 298:344.

*Valenzuela, P., et al. (1984), in Hepatitis B (Millman, I., et al., ed., Plenum Press) pp. 225–236.

*Warner (1984), DNA 3:401.

Wu and Grossman (1987), Methods in Enzymology Vol. 154, Recombinant DNA, Part E.

Wu (1987), Methods in Enzymology vol. 155, Recombinant DNA, Part F.

Zoller (1982), Nucleic Acids Res. 10:6487.

* cited by examiner

| SEQUENCE ID NUMBER | GENOTYPE | | | | | | | |
|---|---|---|---|---|---|---|---|---|
| 1 | GI | CTCCACAGTC | ACTGAGAGCG | ACATCCGTAC | GGAGGAGGCA | ATCTACCAAT | GTTGTGACCT | CGACCCCCAA |
| 2 | | CTCCACAGTC | ACTGAGAGCG | ACATCCGTAC | GGAGGAGGCA | ATTTACCAAT | GTTGTGACCT | GGACCCCCAA |
| 3 | | CTCACACAGTC | ACTGAGAGCG | ACATCCGTAC | GGAGGAGGCA | ATCTACCAAT | GTTGTGATCT | GGACCCCCAA |
| 4 | | CTTACACAGTC | ACTGAGAACG | ACATCCGTAC | GGAGGAGGCA | ATTTACCAAT | GTTGTGACCT | GGACCCCCAA |
| 5 | | CTCCACAGTC | ACTGAGAGCG | ATATCCGTAC | GGAGGAGGCA | ATCTACCAGT | GTTGTGACCT | GGACCCCCAA |
| 6 | | CTCTACAGTC | ACTGAGAGCG | ATATCCGTAC | GGAGGAGGCA | ATCTACCAAT | GTTGTGACCT | GGACCCCCAA |
| 7 | GII | CTCCACAGTC | ACTGAGAATG | ACACCCGTGT | TGAGGAGTCA | ATTTACCAAT | GTTGTGACTT | GGCCCCCGAA |
| 8 | | CTCTACGGTC | ACTGAGAATG | ACATCCGTGT | TGAGGAGTCA | ATTTACCAAA | GTTGTGACTT | GGCCCCCGAG |
| 9 | | ACCACGGTC | ACCGAGAATG | ACATCCGTGT | TGAGGAGTCA | ATTTATCAAT | GTTGTGCCTT | GGCCCCCGAG |
| 10 | | CTCAACGGTC | ACTGAGAGTG | ACATCCGTGT | TGAGGAGTCA | ATTTACCAAT | GTTGTGACTT | GGCCCCCGAA |
| 11 | | CTCCACAGTC | ACTGAGAGTG | ACATCCGTGT | CGAGGAGTCA | ATTTACCAAT | GTTGTGACTT | GGCCCCCGAA |
| 12 | | CTCAACAGTC | ACTGAGAGTG | ACATCCGTGT | TGAGGAGTCA | ATCTACCAAT | GTTGTGACTT | GGCCCCCGAA |
| 13 | GIII | CTCAACCGTC | ACTGAGAGAG | ACATCAGAAC | TGAGGAGTCC | ATATACCGAG | CCTGCTCCCT | GCCTGAGGAG |
| 14 | | CTCTACAGTC | ACGTAAAAGG | ACATCACATC | CTAGGAGTCC | ATCTACCAGT | CCTGTTCACT | GCCCGAGGAG |
| 15 | | CTCTACAGTC | ACAGAGAGGG | ACATCAGAAC | CGAGGAGTCC | ATCTATCTGT | CCTGCTCACT | GCCTGAGGAG |
| 16 | | CTTACAGTC | ACGGAGAGGG | ACATCAGAAC | CGAGGAGTCC | ATCTATCTGT | CCTGTTCACT | GCCTGAGGAG |
| 17 | | CTCAACCGTC | ACGGAGAGGG | ACATCAGAAC | AGAAGAATCC | ATATATCAGG | GTTGTTCCCT | GCCTCAGGAG |
| 18 | GV | CTCGACCGTT | ACCGAACATG | ACATAATGAC | TGAAGAGTCT | ATTTACCAAT | CATTGTACTT | GCAGCCTGAG |
| 19 | | CTCGACCGTT | ACCGAACATG | ACATAATGAC | TGAAGAGTCC | ATTTACCAAT | CATTGTACTT | GCAGCCTGAG |
| 20 | GIV | CTCTACTGTC | ACTGAACAGG | ACATCAGGGT | GGAAGAGGAG | ATATACCAGT | GCTGTAACCT | TGAACCGGAG |
| 21 | | CTCGACTGTC | ACTGAACAGG | ACATCAGGGT | GGAAGAGGAG | ATATACCAAT | GCTGTAACCT | TGAACCGGAG |
| 22 | | CTCAACTGTC | ACTGAACAGG | ACATCAGGGT | GGAAGAGGAG | ATATACCAAT | GCTGTAACCT | TGAACCGGAG |

FIG. 2A

| SEQUENCE ID NUMBER | GENOTYPE | | | | | | | |
|---|---|---|---|---|---|---|---|---|
| 1 | GI | 71 | GCCCGCGTGG | CCATCAAGTC | CCTCACCGAG | AGGCTTTATG | TTGGGGGCCC | TCTTACCAAT | TCAAGGGGGG |
| 2 | GI | 71 | GCCCGCATGG | CCATCAAGTC | CCTCACTGAG | AGGCTTTATG | TCGGGGGCCC | TCTTACCAAT | TCAAGGGGGG |
| 3 | GI | 71 | GCCCGCGTGG | CCATCAAGTC | CCTCACTGAG | AGGCTTTACG | TTGGGGGCCC | TCTTACCAAT | TCAAGGGGGG |
| 4 | GI | 71 | GCCCGCGTGG | CCATCAAGTC | CCTCACTGAG | AGGCTTTATG | TTGGGGGCCC | CCTTACCAAT | TCAAGGGGGG |
| 5 | GI | 71 | GCCCGCGTGG | CCATCAAGTC | CCTCACCGAG | AGGCTTTATG | TCGGGGGCCC | TCTTACCAAT | TCAAGGGGGG |
| 6 | GI | 71 | GCCCGTGTGG | CCATCAAGTC | CCTCACTGAG | AGGCTTTATG | TTGGGGGCCC | TCTTACCAAT | TCAAGGGGGG |
| 7 | GII | 71 | GCCAGACAGG | CCATAAGGTC | GCTCACAGAG | CGGCTCTATG | TCGGGGGTCC | TATGACTAAC | TCCAAAGGGC |
| 8 | | 71 | GCCAGACAAG | CCATAAGGTC | GCTCACAGAG | CGGCTCTACA | TCGGGGGCCC | CCTGACTAAT | TCAAAAGGGC |
| 9 | | 71 | GCTAGACAGG | CCATAAGGTC | GCTCACAGAG | CGGCTTTATA | TCGGGGGCCC | CCTGACCAAT | TCAAAGGGGC |
| 10 | | 71 | GCCAGGCAGG | CCATAAGGTC | GCTCACCGAG | CGACTTTATA | TCGGGGGCCC | CCTGACTAAT | TCAAAGGGGC |
| 11 | | 71 | GCCAGACAGG | CTATAAGGTC | GCTCACAGAG | CGGCTGTACA | TCGGGGGTCC | CCTGACTAAC | TCAAAAGGGC |
| 12 | | 71 | GCCAGACAGG | CTATAAGGTC | GCTCACAGAG | CGGCTGTACA | TCGGGGGTCC | CCTGACTAAT | TCAAAGGGGC |
| 13 | GIII | 71 | GCTCACATTG | CCATACACTC | GCTGACTGAG | AGGCTCTACG | TGGGAGGGCC | CATGTTCAAC | AGCAAGGGGC |
| 14 | | 71 | GCTCGAACTG | CTATACACTC | ACTGACTGAG | AGACTATACG | TAGGGGGGCC | CATGACAAAC | AGCAAGGGGC |
| 15 | | 71 | GCCCGAACTG | CTATACACTC | ACTGACTGAG | AGACTGTACG | TAGGGGGGCC | CATGACAAAC | AGCAAGGGGC |
| 16 | | 71 | GCTCGAACTG | CCATACACTC | ACTGACTGAG | AGGCTGTACG | TAGGGGGGCC | CATGACAAAC | AGCAAGGGAC |
| 17 | | 71 | GCTAGAACAGG | CTATCCACTC | GCTCACTGAG | AGACTCTACG | TAGGAGGGCC | CATGACAAAC | AGCAAGGGGC |
| 18 | GV | 71 | GCGCGTGTGG | CAATACGGTC | ACTCACCCAA | CGCCTGTACT | GTGGAGGCCC | GTGGAGCCCC | AGCAAGGGGC |
| 19 | | 71 | GCACGCGCGG | CAATACGGTC | ACTCACCCAA | CGCCTGTACT | GTGGAGGCCC | GTGGAGCCCC | AGCAAGGGGC |
| 20 | GIV | 71 | GCCAGGAAAG | TGATCTCCTC | CCTCACGGAG | CGGCTTTACT | GCGGGGGCCC | TATGTTCAAC | AGCAAGGGGG |
| 21 | | 71 | GCCAGGAAAG | TGATCTCCTC | CCTCACGGAG | CGGCTTTACT | GCGGGGGCCC | TATGTTCAAT | AGCAAGGGGG |
| 22 | | 71 | GCCAGGAAAG | TGATCTCCTC | CCTCACGGAA | CGGCTTTACT | GCGGGGGCCC | TATGTTCAAC | AGCAAGGGGG |

FIG. 2B

| SEQUENCE ID NUMBER | GENOTYPE | | | | | | | |
|---|---|---|---|---|---|---|---|---|
| 1 | GI | 141 | AGAACTGCGG | CTATCGCCAGG | TGCCGCGCGA | GCGGCGTACT | GACAACTAGC | TGTGGTAACA | CCCTCACTTG |
| 2 | | 141 | AGAACTGCGG | CTACCGCCAGG | TGCCGCGCGA | GCGGCGTACT | GACAACTAGC | TGTGGTAACA | CCCTCACTTG |
| 3 | | 141 | AGAACTGCGG | CTACCGCCAGG | TGCCGGGCGA | GCGGCGTACT | GACAACTAGC | TGTGGTAATA | CCCTCACTTG |
| 4 | | 141 | AGAACTGCGG | CTATCGCCAGG | TGCCGCGCGA | GCGGCGTACT | GACAACTAGC | TGTGGTAACA | CCCTCACTTG |
| 5 | | 141 | AAAACTGCGG | CTATCGCCAGG | TGCCGCGCAA | GCGGCGTACT | GACAACTAGC | TGTGGTAACA | CCCTCACTTG |
| 6 | | 141 | AGAACTGCGG | CTACCGCCAGG | TGCCGCGCAA | GCGGCGTACT | GACGACTAGC | TGTGGTAATA | CCCTCACTTG |
| 7 | GII | 141 | AGAACTGCGG | CTATCGCCGG | TGCCGCGCGA | GCGGCGTGCT | GACGACTAGC | TGCGGTAATA | CCCTCACATG |
| 8 | | 141 | AGAACTGCGG | CTATCGCCGG | TGCCGCGCCA | GCGTGCGTGCT | GACGACTAGC | TGCGGTAATA | CCCTCACATG |
| 9 | | 141 | AGAACTGCGG | TTATCGCCGG | TGCCGCGCCA | GCGGCGTACT | GACGACCAGC | TGCGGTAATA | CCCTTACATG |
| 10 | | 141 | AGAACTGCGG | TTATCGCCGG | TGCCGCGCGA | GCGGCGTGCT | GACGACTAGC | TGCGGTAATA | CCCTCACATG |
| 11 | | 141 | AGAACTGCGG | CTATCGCCGG | TGCCGCGCAA | GCGGCGTGCT | GACGACTAGC | TGCGGTAACA | CCCTCACATG |
| 12 | | 141 | AGAACTGCGG | CTATCGCCGG | TGCCGCGCAA | GCGGCGTGCT | GACGACTAGC | TGCGGTAATA | CCCTCACATG |
| 13 | GIII | 141 | AGAACTGCGG | GTACAGGCGT | TGCCGCGCCA | GCGGGGTGCT | CACCACTAGC | ATGGGAACA | CCATGACGTG |
| 14 | | 141 | AATCCTGCGG | GTACAGGCGT | TGCCGCGCGA | GCGCAGTGCT | CACCACCAGC | ATGGGCAACA | CACTCACGTG |
| 15 | | 141 | AATCCTGCGG | GTACAGGCGT | TGCCGCGCGA | GCGGAGTGCT | CACCACCAGC | ATGGGCAACA | CGCTCACGTG |
| 16 | | 141 | AATCCTGCGG | GTACAGGCGT | TGCCGCGCGA | GCGGAGTGCT | CACCACCAGC | ATGGGTAACA | CACTCACGTG |
| 17 | | 141 | AATCCTGCGG | TTACAGGCGT | TGCCGCGCCA | GCGGGGTCTT | CACCACCAGC | ATGGGAATA | CCATGACATG |
| 18 | GV | 141 | AACAATGTGG | TTATCGTAGA | TGCCGCGCCA | GCGGCGTCTT | CACCACTAGT | ATGGGCAACA | CCATGACGTG |
| 19 | | 141 | AACAATGTGG | TTACCGTAGA | TGCCGCGCCA | GCGGCGTCTT | CACCACCAGT | ATGGGCAACA | CCATGACGTG |
| 20 | GIV | 141 | CCCAGTGTGG | TTATCGCCGT | TGCCGTGCTA | GTGGAGTCCT | GCTACCAGC | TTCGGCAACA | CAATCACTTG |
| 21 | | 141 | CCCAGTGTGG | TTATCGCCGT | TGCCGTGCTA | GTGGAGTTCT | GCTACCAGC | TTCGGCAACA | CAATCACTTG |
| 22 | | 141 | CCCAGTGTGG | TTATCGCCGT | TGCCGTGCCA | GTGGAGTTCT | GCCTACCAGC | TTCGGCAACA | CAATCACTTG |

FIG. 2C

| SEQUENCE ID NUMBER | GENOTYPE | | | | | | | | |
|---|---|---|---|---|---|---|---|---|---|
| 1 | GI | 211 | CTACATCAAG | GCCCGGGCAG | CCTGTCGAGC | CGCAGGGCTC | CAGGACTGCA | CCATGCTCGT | GTGTGGCGAC |
| 2 | | 211 | CTACATCAAG | GCCCGGGCAG | CCTGTCGAGC | CGCAGGGCTC | CAGGACTGCA | CCATGCTCGT | GTGTGGCGAC |
| 3 | | 211 | CTACATCAAG | GCCCGGGCAG | CCTGTCGAGC | CGCAGGGCTC | CGGGACTGCA | CCATGCTCGT | GTGTGGTGAC |
| 4 | | 211 | CTACATTAAG | GCCCGGGCAG | CCTGTCGAGC | CGCAGGGCTC | CAGGACTGCA | CCATGCTCGT | GTGTGGCGAC |
| 5 | | 211 | TTACATCAAG | GCCCAAGCAG | CCTGTCGAGC | CGCAGGGCTC | CGGGACTGCA | CCATGCTCGT | GTGTGGCGAC |
| 6 | | 211 | TTACATCAAG | GCCCGGGCAG | CCTGTCGAGC | CGCAGGGCTC | CAGGACTGCA | CCATGCTCGT | GTGTGGCGAC |
| 7 | GII | 211 | CTACCTGAAG | GCCACAGCGG | CCTGTCGAGC | TGCCAAGCTC | CAGGACTGCA | CGATGCTCGT | GAACGGAGAC |
| 8 | | 211 | TTACTTGAAG | GCCACTGCGG | CCTGTAGAGC | TGCGAAGCTC | CAGGACTGCA | CGATGCTCGT | GTGCGGAGAC |
| 9 | | 211 | TTACTTGAAG | GCCTCTGCAG | CCTGTCGAGC | CGCGAAGCTC | CAGGACTGCA | CGATGCTCGT | GTGTGGGGAC |
| 10 | | 211 | TTACTTGAAG | GCCTCTGCAG | CCTGTCGAGC | TGCAAAGCTC | CAGGACTGCA | CGATGCTCGT | GAACGGGGAC |
| 11 | | 211 | TTACTTGAAG | GCCTCTCCGG | CCTGTCGAGC | TGCGAAGCTC | CAGGACTGCA | CGATGCTCGT | GTCGGTGAC |
| 12 | | 211 | TTACATGAAG | GCCAGTGCGG | CCTGTCGAGC | TGCGAAGCTC | CAGGACTGCA | CAATGCTCGT | GTGCGGTGAC |
| 13 | GIII | 211 | CTATGTAAAA | GCCCTAGCGG | CTTGCAAGGC | TGCAGGGATA | GTTGCACCCT | CAATGCTCGT | ATGCGGCGAC |
| 14 | | 211 | CTACGTAAAA | GCCAGGGCGG | CCCCTAGAGC | CGTGTAACGC | GTTGCTCCCA | CCATGCTGGT | GTGCGGTGAC |
| 15 | | 211 | CTACGTGAAA | GCCAGAGCGG | CCTCTCGAGC | CGTGTAACGC | GTTGCTCCCA | CCATGTTGGT | GTGCGGCGAC |
| 16 | | 211 | CTACGTGAAA | GCTAAAGCGG | GCTCTCTGAGC | CATGTAACGC | GTTGCCCCCA | CCATGTTGGT | GTGCGGCGAC |
| 17 | | 211 | CTACATCAAA | GCCCTTGCAG | CCCCTAGAGC | CGTGCAAAGC | GTGGACCCTA | TCATGCTGGT | GTGTGGAGAC |
| 18 | GV | 211 | CTACATTAAG | GCTTTAGCCT | CCTGTAGAGC | CGCAAAGCTC | CAGGACTGCA | CGCTCCTGGT | GTGTGGTGAT |
| 19 | | 211 | CTACATCAAG | GCTTCAGCCG | CCTGTAGAGC | TGCAAAGCTC | CAGGACTGCA | CGCTCCTGGT | GTGTGGTGTG |
| 20 | GIV | 211 | TTACATCAAG | GCTAGAGCGG | CTTCGAAGC | CGCAGGCCTC | CGGAACCCGG | ACTTTCTTGT | CTGCGGAGAT |
| 21 | | 211 | TTACATCAAG | GCTAGAGCGG | CTGAGAGCGG | CGCAGGGCGG | CGGACCCCGG | ACTTTCTTCT | CTGCGGAGAT |
| 22 | | 211 | TTACATCAAA | GCTAGAGCGG | CTGCCAGAGC | CGCAGGCCTC | CGGAACCCGG | ACTTTCTTGT | CTGCGGAGAT |

FIG. 2D

| SEQUENCE ID NUMBER | GENOTYPE | | | | | | | |
|---|---|---|---|---|---|---|---|---|
| 1 | GI | 281 | GACTTAGTCG | TTATCTGTGA | AAGCCAGGAG | GTCCAGGAGG | ACGCGGCGAG | CCTGAGAGCC |
| 2 | | 281 | GACTTAGTCG | TTATCTGTGA | AAGTGCCGGG | GTCCAGGAGG | ACGCGGCGAG | CCTGAGAGCC |
| 3 | | 281 | GACTTGGTCG | TTATCTGTGA | GAGTGCCGGG | GTCCAGGAGG | ACGCGGCGAG | CCTGAGAGCC |
| 4 | | 281 | GACTTAGTCG | TTATCTGTGA | GAGTGCGGGA | GTCCAGGAGG | ACGCGGCGAA | CTTGAGAGCC |
| 5 | | 281 | GACTTAGTCG | TTATCTGTGA | AAGTCAGGGA | GTCCAGGAGG | ATGCAGCGAA | CCTGAGAGCC |
| 6 | | 281 | GACCTAGTCG | TTATCTGCGA | AAGTGCCGGG | GTCCAGGAGG | ACGCGGCGAG | CCTGAGAGCC |
| 7 | GII | 281 | GACCTTGTCG | TTATCTGTGA | AAGCGCGGGG | AACCAGAGG | ACGCGGCAAG | CCTACGAGCC |
| 8 | | 281 | GACCTTGTCG | TTATCTGTGA | AAGCGCCGGA | ACCCAGAGG | ATGCGGCGAG | CCTACGAGTC |
| 9 | | 281 | GACCTTGTCG | TTATCTGTGA | AAGCCGCGGA | ACCCAGAGG | ACGCGGCGAA | CCTACGAGTC |
| 10 | | 281 | GACCTTGTCG | TTATCTGCGA | GAGCGCGGGA | ACCAAGAGG | ACGCGGCGAG | CCTACGAGTC |
| 11 | | 281 | GACCTTGTCG | TTATCTGTGA | GAGCGCGGGA | ACCAAGAGG | ACGCGGCGAG | CCTACGAGTC |
| 12 | | 281 | GACCTTGTCG | TTATCTGCGA | GAGCGCGGGG | ACCCAGAGG | ACGCGGCGAG | CCTACGAGTC |
| 13 | GIII | 281 | GACTTAGTTG | TCATCTCAGA | AAGCCAGGGG | ACTGAGGAGG | ACGAGCGAA | CCTGAGAGCT |
| 14 | | 281 | GACCTAGTCG | TCATCTCAGA | GAGTCAAGGG | GCTGAGGAGG | ACGAGCAGA | CCTGAGAGTC |
| 15 | | 281 | GACCTGGTTG | TCATCTCAGA | GAGTCAGGGG | GTCGAGGAAG | ATGAGCGAA | CCTGAGAGTC |
| 16 | | 281 | GACCTAGTCG | TCATCTCAGA | GAGTCAAGGG | GTCGAGGAGG | ATGAGCGAA | CCTGAGAGCT |
| 17 | | 281 | GACCTGGTCG | TCATCTCGGA | GAGCGAAGGT | AACGAGGAGG | ACGAGCGAA | CCTGAGAGCC |
| 18 | GV | 281 | GATCTTGTGG | CCATTGCGA | GAGCCAGGGG | ACGCACGAGG | ATAAAGCGAG | CCTGAGAGCC |
| 19 | | 281 | ACCTTGGTGG | CCATTGCGA | GAGCCAAGGG | ACGCACGAGG | ATGAAGCGTG | CCTGAGAGTC |
| 20 | GIV | 281 | GATCTGGTCG | TGGTGGCTGA | GAGTGATGGC | GTCGACGAGG | ATAGAGCAGC | CCTGCGAGCC |
| 21 | | 281 | GATCTGGTTG | TGGTGGCTGA | GAGTGATGGC | GTCGACGAGG | ATAGAACAGC | CCTGCGAGCC |
| 22 | | 281 | GATCTGGTTG | TGGTGGCTGA | GAGTGATGGC | GTCAATGAGG | ATAGAGCAGC | CCTGGGAGCC |

340 TOTAL

C0772/7000
/1842R

FIG. 2E

| SEQUENCE ID NUMBER | GENOTYPE | | | | | | |
|---|---|---|---|---|---|---|---|
| 23 | GI | 1 | GACGGCGTTG | GTAATGCTC | AGTGCTCCG | GATCCCACAA | GCCATCTTGG ACATGATCGC |
| 24 | GI | 1 | GACGGCGTTG | GTGTAGCTC | AGTACTCCG | GATCCCACAA | GCCATCATGG ACATGATCGC |
| 25 | GI | 1 | AACGGCGCTG | GTAGTAGCTC | AGTCGCTCAG | GGTCCCGCAA | GCCATCGTGG ACATGATCGC |
| 26 | GII | 1 | GACAGCCCTA | GTGGTATCGC | AGTTACTCCG | GATCCCACAA | GCCGTCATGG ATATGGTGGC |
| 27 | GII | 1 | AGCAGCCCTA | GTGGTGTCGC | AGTTACTCCG | GATCCCACAA | AGCATCGTGG ACATGGTGGC |
| 28 | GII | 1 | GGCAGCCCTA | GTGGTGTCGC | AGTTACTCCG | GATCCCGCAA | GCTGTCGTGG ACATGGTGGC |
| 29 | GIV | 1 | TGTGGGTATG | GTGGTGGCGC | ACGTCCTGCG | TTTGCCCCAG | ACCTTGTTCG ACATAATAGC |
| 30 | GIV | 1 | TGTGGGTATG | GTGGTAGCAC | ACGTCCTGCG | TCTGCCCCAG | ACCTTGTTCG ACATAATAGC |
| 31 | GIV | 1 | TGTGGGTATG | GTGGTGGGGC | AAGTCCTGCG | TTTGCCCCAG | ACCTTGTTCG ACGTGCTAGC |
| 32 | GIII | 1 | TACCACTATG | CTCCTGGCAT | ACTTGGTGCG | CATCCGGAG | GTCATCCGGT ACATTATCAC |
| 23 | GI | 61 | TGGTGCTCAC | TGGGAGTCC | TGGCGGGCAT | AGCGTATTTC | |
| 24 | GI | 61 | TGGAGCCCAC | TGGGAGTCC | TGGCGGGCAT | AGCGTATTTC | |
| 25 | GI | 61 | TGGTGCCCAC | TGGGAGTCC | TAGCGGGCAT | AGCGTATTTT | |
| 26 | GII | 61 | GGGGGCCCAC | TGGGAGTCC | TGGCGGGCCT | TGCCTACTAT | |
| 27 | GII | 61 | GGGGGCCCAC | TGGGAGTCC | TGGCGGGCCT | TGCTTACTAT | |
| 28 | GII | 61 | GGGGGCCCAC | TGGGAATCC | TAGCGGGTCT | TGCCTACTAT | |
| 29 | GIV | 61 | CGGGGCCCAT | TGGGCATCT | TGGCGGGCTT | GGCCTATTAC | |
| 30 | GIV | 61 | CGGGGCCCAT | TGGGGCATCT | TGGCAGGCCT | AGCCTATTAC | |
| 31 | GIV | 61 | CGGGGCCCAT | TGGGGCATCT | TGGCGGGCCT | GGCCTATTAC | |
| 32 | GIII | 61 | GGGAGGACAC | TGGGCGTGA | TGTTTGGCCT | GGCTTATTTC | |

100 Total
/1843R

FIG. 3

| SEQUENCE ID NUMBER | GENOTYPE | | | | | | |
|---|---|---|---|---|---|---|---|
| 33 | GI | 1 | GTTAGTATGA | GTGTCGTGCA | GCCTCCAGGA | CCCCCCCTCC | CGGGAGAGCC | ATAGTGGTCT |
| 34 | | 1 | GTTAGTATGA | GTGTCGTGCA | GCCTCCAGGA | CCCCCCCTCC | CGGGAGAGCC | ATAGTGGTCT |
| 35 | | 1 | GTTAGTATGA | GTGTCGTGCA | GCCTCCAGGA | CCCCCCCTCC | CGGGAGAGCC | ATAGTGGTCT |
| 36 | | 1 | GTTAGTATGA | GTGTCGTGCA | GCCTCCAGGA | CCCCCCCTCC | CGGGAGAGCC | ATAGTGGTCT |
| 37 | | 1 | GTTAGTATGA | GTGTCGTGCA | GCCTCCAGGA | CCCCCCCTCC | CGGGAGAGCC | ATAGTGGTCT |
| 38 | | 1 | GTTAGTATGA | GTGTCGTGCA | GCCTCCAGGA | CCCCCCCTCC | CGGGAGAGCC | ATAGTGGTCT |
| 39 | GII | 1 | GTTAGTATGA | GTGTCGTGCA | GCCTCCAGGA | CCCCCCCTCC | CGGGAGAGCC | ATAGTGGTCT |
| 40 | | 1 | GTTAGTATGA | GTGTCGTGCA | GCCTCCAGGA | CCCCCCCTCC | CGGGAGAGCC | ATAGTGGTCT |
| 41 | | 1 | GTTAGTATGA | GTGTCGTGCA | GCCTCCAGGA | CCCCCCCTCC | CGGGAGAGCC | ATAGTGGTCT |
| 42 | | 1 | GTTAGTATGA | GTGTCGTGCA | GCCTCCAGGA | CCCCCCCTCC | CGGGAGAGCC | ATAGTGGTCT |
| 43 | | 1 | GTTAGTATGA | GTGTCGTGCA | GCCTCCAGGA | CCCCCCCTCC | CGGGAGAGCC | ATAGTGGTCT |
| 44 | | 1 | GTTAGTATGA | GTGTCGTGCA | GCCTCCAGGA | CCCCCCCTCC | CGGGAGAGCC | ATAGTGGTCT |
| 45 | | 1 | GTTAGTATGA | GTGTCGTGCA | GCCTCCAGGA | CCCCCCCTCC | CGGGAGAGCC | ATAGTGGTCT |
| 46 | GIII | 1 | GCTAGTATCA | GTCTCGTACA | GCCTCCAGGC | CCCCCCCTCC | CGGGAGAGCC | ATAGTGGTCT |
| 47 | | 1 | GTTAGTATGA | GTCTCGTACA | GCCTCCAGGC | CCCCCCTCC | CGGGAGAGCC | ATAGTGGTCT |
| 48 | GIV | 1 | GTTAGTACGA | GTGTCGTGCA | GCCTCCAGGA | CTCCCCCTCC | CGGGAGAGCC | ATAGTGGTCT |
| 49 | | 1 | GTTAGTACGA | GTGTCGTGCA | GCCTCCAGGA | CCCCCCCTCC | CGGGAGAGCC | ATAGTGGTCT |
| 50 | GV | 1 | GTTAGTATGA | GTGTCGAACA | GCCTCCAGGA | CCCCCCCTCC | CGGGAGAGCC | ATAGTGGTCT |
| 51 | | 1 | GTTAGTATGA | GTGTCGAACA | GCCTCCAGGA | CCCCCCCTCC | CGGGAGAGCC | ATAGTGGTCT |

FIG. 4A

| SEQUENCE ID NUMBER | GENOTYPE | | | | | |
|---|---|---|---|---|---|---|
| 33 | GI | 61 | GCGGAACCGG TGAGTACACC | GGAATTGCCA | GGACGACCGG | GTCCTTTCTT | GGATCAACCC |
| 34 | | 61 | GCGGAACCGG TGAGTACACC | GGAATTGCCA | GGACGACCGG | GTCCTTTCTT | GGATCAACCC |
| 35 | | 61 | GCGGAACCGG TGAGTACACC | GGAATTGCCA | GGACGACCGG | GTCCTTTCTT | GGATCAACCC |
| 36 | | 61 | GCGGAACCGG TGAGTACACC | GGAATTGCCA | GGACGACCGG | GTCCTTTCTT | GGATAAACCC |
| 37 | | 61 | GCGGAACCGG TGAGTACACC | GGAATTGCCA | GGACGACCGG | GTCCTTTCTT | GGATCAACCC |
| 38 | | 61 | GCGGAACCGG TGAGTACACC | GGAATTGCCA | GGACGACCGG | GTCCTTTCTT | GGATAAACCC |
| 39 | GII | 61 | GCGGAACCGG TGAGTACACC | GGAATTGCCA | GGACGACCGG | GTCCTTTCTT | GGATCAACCC |
| 40 | | 61 | GCGGAACCGG TGAGTACACC | GGAATTGCCA | GGACGACCGG | GTCCTTTCTT | GGATCAACCC |
| 41 | | 61 | GCGGAACCGG TGAGTACACC | GGAATTGCCA | GGACGACCGG | GTCCTTTCTT | GGATCAACCC |
| 42 | | 61 | GCGGAACCGG TGAGTACACC | GGAATTGCCA | GGACGACCGG | GTCCTTTCTT | GGATCAACCC |
| 43 | | 61 | GCGGAACCGG TGAGTACACC | GGAATTGCCA | GGACGACCGG | GTCCTTTCTT | GGATCAACCC |
| 44 | | 61 | GCGGAACCGG TGAGTACACC | GGAATTGCCA | GGACGACCGG | GTCCTTTCTT | GGATCAACCC |
| 45 | | 61 | GCGGAACCGG TGAGTACACC | GGAATTGCCA | GGACGACCGG | GTCCTTTCTT | GGATCAACCC |
| 46 | GIII | 61 | GCGGAACCGG TGAGTACACC | GGAATTGCCG | GGAAGACTGG | GTCCTTTCTT | GGATAAACCC |
| 47 | | 61 | GCGGAACCGG TGAGTACACC | GGAATTGCTG | GGAAGACTGG | GTCCTTTCTT | GGATAAACCC |
| 48 | GIV | 61 | GCGGAACCGG TGAGTACACC | GGAATCGCTG | GGGTGACCGG | GTCCTTTCTT | GGAGCAACCC |
| 49 | | 61 | GCGGAACCGG TGAGTACACC | GGAATCGCTG | GGGTGACCGG | GTCCTTTCTT | GGAGTAACCC |
| 50 | GV | 61 | GCGGAACCGG TGAGTACACC | GGAATTGCCG | GGATGACCGG | GTCCTTTCTT | GGATAAACCC |
| 51 | | 61 | GCGGAACCGG TGAGTACACC | GGAATTGCCA | GGATGACCGG | GTCCTTTCTT | GGATAAACCC |

FIG. 4B

| SEQUENCE ID NUMBER | GENOTYPE | | | | | | |
|---|---|---|---|---|---|---|---|
| 33 | GI | 121 | GCTCAATGCC | TGGAGATTTG | GGCGTGCCCC | CGCAAGACTG | CTAGCCGAGT | AGTGTTGGGT |
| 34 | | 121 | GCTCAATGCC | TGGAGATTTG | GGCGTGCCCC | CGCAAGACTG | CTAGCCGAGT | AGTGTTGGGT |
| 35 | | 121 | GCTCAATGCC | TGGAGATTTG | GGCACGCCCC | CGCAAGATCA | CTAGCCGAGT | AGTGTTGGGT |
| 36 | | 121 | GCTCAATGCC | TGGAGATTTG | GGCGTGCCCC | CGCGAGACTG | CTAGCCGAGT | AGTGTTGGGT |
| 37 | | 121 | GCTCAATGCC | TGGAGATTTG | GGCGTGCCCC | CGCAAGACTG | CTAGCCGAGT | AGTGTTGGGT |
| 38 | | 121 | GCTCAATGCC | TGGAGATTTG | GGCGTGCCCC | CGCAAGACTG | CTAGCCGAGT | AGTGTTGGGT |
| 39 | GII | 121 | GCTCAATGCC | TGGAGATTTG | GGCGTGCCCC | CGCGAGACTG | CTAGCCGAGT | AGTGTTGGGT |
| 40 | | 121 | GCTCAATGCC | TGGAGATTTG | GGCGTGCCCC | CGCGAGACTG | CTAGCCGAGT | AGTGTTGGGT |
| 41 | | 121 | GCTCAATGCC | TGGAGATTTG | GGCGTGCCCC | CGCGAGACTG | CTAGCCGAGT | AGTGTTGGGT |
| 42 | | 121 | GCTCAATGCC | TGGAGATTTG | GGCGTGCCCC | CGCGAGACTG | CTAGCCGAGT | AGTGTTGGGT |
| 43 | | 121 | GCTCAATGCC | TGGAGATTTG | GGCGTGCCCC | CGCGAGACTG | CTAGCCGAGT | AGTGTTGGGT |
| 44 | | 121 | GCTCAATGCC | TGGAGATTTG | GGCGTGCCCC | CGCGAGACTG | CTAGCCGAGT | AGTGTTGGGT |
| 45 | | 121 | GCTCAATGCC | TGGAGATTTG | GGCGTGCCCC | CGCGAGACTG | CTAGCCGAGT | AGTGTTGGGT |
| 46 | GIII | 121 | ACTCTATGCC | CGGCCATTTG | GGCGTGCCCC | CGCAAGACTG | CTAGCCGAGT | AGCGTTGGGT |
| 47 | | 121 | ACTCTATGCC | CAGCCATTTG | GGCGTGCCCC | CGCAAGACTG | CTAGCCGAGT | AGCGTTGGGT |
| 48 | GIV | 121 | GCTCAATACC | CAGAAATTTG | GGCGTGCCCC | CGCGAGATCA | CTAGCCGAGT | AGTGTTGGGT |
| 49 | | 121 | GCTCAATACC | CAGAAATTTG | GGCGTGCCCC | CGCGAGATCA | CTAGCCGAGT | AGTGTTGGGT |
| 50 | GV | 121 | GCTCAATGCC | CGGAGATTTG | GGCGTGCCCC | CGCGAGACTG | CTAGCCGAGT | AGTGTTGGGT |
| 51 | | 121 | GCTCAATGCC | CGGAGATTTG | GGCGTGCCCC | CGCGAGACTG | CTAGCCGAGT | AGTGTTGGGT |

FIG. 4C

| SEQUENCE ID NUMBER | GENOTYPE | | | | | | |
|---|---|---|---|---|---|---|---|
| 33 | GI | 181 | CGCGAAAGGC | CTTGTGGTAC | TGCCTGATAG | GGTGCTTGCG | AGTGCCCCGG | GAGGTCTCGT |
| 34 | | 181 | CGCGAAAGGC | CTTGTGGTAC | TGCCTGATAG | GGTGCTTGCG | AGTGCCCCGG | GAGGTCTCGT |
| 35 | | 181 | CGCGAAAGGC | CTTGTGGTAC | TGCCTGATAG | GGTGCTTGCG | AGTGCCCCGG | GAGGTCTCGT |
| 36 | | 181 | CGCGAAAGGC | CTTGTGGTAC | TGCCTGATAG | GGTGCTTGCG | AGTGCCCCGG | GAGGTCTCGT |
| 37 | | 181 | CGCGAAAGGC | CTTGTGGTAC | TGCCTGATAG | GGTGCTTGCG | AGTGCCCCGG | GAGGTCTCGT |
| 38 | | 181 | CGCGAAAGGC | CTTGTGGTAC | TGCCTGATAG | GGTGCTTGCG | AGTGCCCCGG | GAGGTCTCGT |
| 39 | GII | 181 | CGCGAAAGGC | CTTGTGGTAC | TGCCTGATAG | GGTGCTTGCG | AGTGCCCCGG | GAGGTCTCGT |
| 40 | | 181 | CGCGAAAGGC | CTTGTGGTAC | TGCCTGATAG | GGTGCTTGCG | AGTGCCCCGG | GAGGTCTCGT |
| 41 | | 181 | CGCGAAAGGC | CTTGTGGTAC | TGCCTGATAG | GGTGCTTGCG | AGTGCCCCGG | GAGGTCTCGT |
| 42 | | 181 | CGCGAAAGGC | CTTGTGGTAC | TGCCTGATAG | GGTGCTTGCG | AGTGCCCCGG | GAGGTCTCGT |
| 43 | | 181 | CGCGAAAGGC | CTTGTGGTAC | TGCCTGATAG | GGTGCTTGCG | AGTGCCCCGG | GAGGTCTCGT |
| 44 | | 181 | CGCGAAAGGC | CTTGTGGTAC | TGCCTGATAG | GGTGCTTGCG | AGTGCCCCGG | GAGGTCTCGT |
| 45 | | 181 | CGCGAAAGGC | CTTGTGGTAC | TGCCTGATAG | GGTGCTTGCG | AGTGCCCCGG | GAGGTCTCGT |
| 46 | GIII | 181 | TGCGAAAGGC | CTTGTGGTAC | TGCCTGATAG | GGTGCTTGCG | AGTGCCCCGG | GAGGTCTCGT |
| 47 | | 181 | TGCGAAAGGC | CTTGTGGTAC | TGCCTGATAG | GGTGCTTGCG | AGTGCCCCGG | GAGGTCTCGT |
| 48 | GIV | 181 | CGCGAAAGGC | CTTGTGGTAC | TGCCTGATAG | GGTGCTTGCG | AGTGCCCCGG | GAGGTCTCGT |
| 49 | | 181 | CGCGAAAGGC | CTTGTGGTAC | TGCCTGATAG | GGTGCTTGCG | AGTGCCCCGG | GAGGTCTCGT |

FIG. 4D

```
==========================================
SEQUENCE
ID NUMBER   GENOTYPE
==========================================
    33         GI      241    AGACCGTGCA CC
    34                 241    AGACCGTGCA CC
    35                 241    AGACCGTGCA CC
    36                 241    AGACCGTGCA CC
    37                 241    AGACCGTGCA CC
    38                 241    AGACCGTGCA CC
==========================================
    39         GII     241    AGACCGTGCA CC
    40                 241    AGACCGTGCA TC
    41                 241    AGACCGTGCA CC
    42                 241    AGACCGTGCA CC
    43                 241    AGACCGTGCA CC
    44                 241    AGACCGTGCA CC
    45                 241    AGACCGTGCA CC
==========================================
    46         GIII    241    AGACCGTGCA TC
    47                 241    AGACCGTGCA TC
==========================================
    48         GIV     241    AGACCGTGCA AC
    49                 241    AGACCGTGCA AC
==========================================

252 Total

C0772/7000
/1975R
```

FIG. 4E

| SEQUENCE ID NUMBER | GENOTYPE | | | | | | | |
|---|---|---|---|---|---|---|---|---|
| 52 | GI | 1 | ATGAGCACGA | ATCCTAAACC | TCAAAAAAAA | AACAAACGTA | ACACCAACCG | TCGCCCACAG |
| 53 | | 1 | ATGAGCACGA | ATCCTAAACC | TCAAAGAAAA | ACCAAACGTA | ACACCAACCG | TCGCCCACAG |
| 54 | | 1 | ATGAGCACGA | ATCCTAAACC | TCAAAGAAAA | ACCAAACGTA | ACACCAACCG | TCGCCCACAG |
| 55 | | 1 | ATGAGCACGA | ATCCTAAACC | TCAAAGAAAA | ACCAAACGTA | ACACCAACCG | TCGCCCACAG |
| 56 | | 1 | ATGAGCACGA | ATCCTAAACC | TCAAAGAAGA | ACCAAACGTA | ACACCAACCG | TCGCCCACAG |
| 57 | | 1 | ATGAGCACGA | ATCCTAAACC | TCAAAGAAAA | ACCAAACGTA | ACACCAACCG | TCGCCCACAG |
| 58 | GII | 1 | ATGAGCACGA | ATCCTAAACC | TCAAAGAAAA | ACCAAACGTA | ACACCAACCG | CCGCCCACAG |
| 59 | | 1 | ATGAGCACGA | ATCCTAAACC | TCAAAGAAAA | ACCAAACGTA | ACACCAACCG | CCGCCCACAG |
| 60 | | 1 | ATGAGCACAA | ATCCTAAACC | CCAAAGAAAA | ACCAAACGTA | ACACCAACCG | TCGCCCACAG |
| 61 | | 1 | ATGAGCACAA | ATCCTAAACC | TCAAAGAAAA | ACCAAACGTA | ACACCAACCG | CCGCCCACAG |
| 62 | | 1 | ATGAGCACGA | ATCCTAAACC | TCAAAGAAAA | ACCAAACGTA | ACACCAACCG | CCGCCCACAG |
| 63 | | 1 | ATGAGCACGA | ATCCTAAACC | TCAAAGAAAA | ACCAAACGTA | ACACCAACCG | CCGCCCACAG |
| 64 | | 1 | ATGAGCACGA | ATCCTAAACC | TCAAAGAAAA | ACCAAACGTA | ACACCAACCG | CCGCCCACAG |
| 65 | GIII | 1 | ATGAGCACAA | ATCCTAAACC | TCAAAGAAAA | ACCAAAAGAA | ACACTAACCG | CCGCCCACAG |
| 66 | | 1 | ATGAGCACAA | ATCCTCAACC | TCAAAGAAAA | ACCAAAAGAA | ACACTAACCG | CCGCCCACAG |

FIG. 5A

| SEQUENCE ID NUMBER | GENOTYPE | | | | | | |
|---|---|---|---|---|---|---|---|
| 52 | GI | 61 | GACGTCAAGT | TCCCGGGTGG | CGGTCAGATC | GTTGGTGGAG | TTTACTTGTT | GCCGCGCAGG |
| 53 | | 61 | GACGTCAAGT | TCCCGGGTGG | CGGTCAGATC | GTTGGTGGAG | TTTACTTGTT | GCCGCGCAGG |
| 54 | | 61 | GACGTTAAGT | TCCCGGGTGG | CGGTCAGATC | GTTGGTGGAG | TTTACTTGTT | GCCGCGCAGG |
| 55 | | 61 | GACGTCAAGT | TCCCGGGTGG | CGGTCAGATC | GTTGGTGGAG | TTTACTTGTT | GCCGCGCAGG |
| 56 | | 61 | GACGTCAAGT | TCCCGGGTGG | CGGTCAGATC | GTTGGTGGAG | TTTACTTGTT | GCCGCGCAGG |
| 57 | | 61 | GACGTCAAGT | TCCCGGGTGG | CGGTCAGATC | GTTGGTGGAG | TTTACTTGTT | GCCGCGCAGG |
| 58 | GII | 61 | GACGTTAAGT | TCCCGGGCGG | TGGCCAGGTC | GTTGGTGGAG | TTTACTTGTT | GCCGCGCAGG |
| 59 | | 61 | GACGTCAAGT | TCCCGGGCGG | TGGTCAGATC | GTTGGTGGAG | TTTACTTGTT | GCCGCGCAGG |
| 60 | | 61 | GACGTCAAGT | TCCCGGGCGG | TGGTCAGATC | GTTGGTGGAG | TTTACCTGTT | GCCGCGCAGG |
| 61 | | 61 | GACGTCAAGT | TCCCGGGCGG | TGGTCAGATC | GTTGGTGGAG | TTTACTTGTT | GCCGCGCAGG |
| 62 | | 61 | GACGTCAAGT | TCCCGGGCGG | TGGTCAGATC | GTTGGTGGAG | TTTACCTGTT | GCCGCGCAGG |
| 63 | | 61 | GACGTCAAGT | TCCCGGGCGG | TGGTCAGATC | GTTGGTGGAG | TTTACCTGTT | GCCGCGCAGG |
| 64 | | 61 | GACGTCAAGT | TCCCGGGCGG | TGGTCAGATC | GTTGGTGGAG | TTTACCTGTT | GCCGCGCAGG |
| 65 | GIII | 61 | GACGTCAAGT | TCCCGGGCGG | TGGCCAGATC | GTTGGCGGAG | TATACTTGCT | GCCGCGCAGG |
| 66 | | 61 | GACGTCAAGT | TCCCGGGCGG | TGGTCAGATC | GTTGGCGGAG | TATACTTGTT | GCCGCGCAGG |

FIG. 5B

| SEQUENCE ID NUMBER | GENOTYPE | | | | | | |
|---|---|---|---|---|---|---|---|
| 52 | GI | 121 | GGCCCTAGAT | TGGGTGTGCG | CGCGACGAGA | AAGACTTCCG | AGCGGTCGCA | ACCTCGAGGT |
| 53 | | 121 | GGCCCTAGAT | TGGGTGTGCG | CGCGACGAGG | AAGACTTCCG | AGCGGTCGCA | ACCTCGAGGT |
| 54 | | 121 | GGCCCTAGAT | TGGGTGTGCG | CGCGACGAGG | AAGACTTCCG | AGCGGTCGCA | ACCTCGAGGT |
| 55 | | 121 | GGCCCTAGAT | TGGGTGTGCG | CACGACGAGG | AAGACTTCCG | AGCGGTCGCA | ACCTCGAGGT |
| 56 | | 121 | GGCCCTAGAT | TGGGTGTGCG | CGCGACGAGG | AAGACTTCCG | AGCGGTCGCA | ACCTCGAGGT |
| 57 | | 121 | GGCCCTAGAT | TGGGTGTGCG | CGCGACGAGG | AAGACTTCCG | AGCGGTCGCA | ACCTCGTGGT |
| 58 | GII | 121 | GGCCCCAGGT | TGGGTGTGCC | CGCGACTAGG | AAGACTTCCG | AGCGGTCGCA | ACCTCGTGGA |
| 59 | | 121 | GGCCCCAGGT | TGGGTGTGCC | CGCGACTAGG | AAGACTTCCG | AGCGGTCGCA | ACCTCGTGGA |
| 60 | | 121 | GGCCCCAGGT | TGGGTGTGCC | CGCGACTAGG | AAGACTTCCG | AGCGGTCGCA | ACCTCGTGGA |
| 61 | | 121 | GGCCCCAGGT | TGGGTGTGCC | CGCGACTAGG | AAGACTTCCG | AGCGGTCGCA | ACCTCGTGGA |
| 62 | | 121 | GGCCCCAGGT | TGGGTGTGCC | CGCGACTAGG | AAGACTTCCG | AGCGGTCGCA | ACCTCGTGGA |
| 63 | | 121 | GGCCCCAGGT | TGGGTGTGCC | CGCGACTAGG | AAGACTTCCG | AGCGGTCGCA | ACCTCGTGGA |
| 64 | | 121 | GGCCCCAGGT | TGGGTGTGCC | CGCGACTAGG | AAGACTTCCG | AGCGGTCGCA | ACCTCGTGGA |
| 65 | GIII | 121 | GGCCCGAGAT | TGGGTGTGCC | CGCGACGAGG | AAAACTTCCG | AACGATCCCA | GCCACGCGGA |
| 66 | | 121 | GGCCCCAGGT | TGGGTGTGCC | CGCGACGAGG | AAAACTTCCG | AACGGTCCCA | GCCACGTGGG |

FIG. 5C

| SEQUENCE ID NUMBER | GENOTYPE | | | | | | |
|---|---|---|---|---|---|---|---|
| 52 | GI | 181 | AGACGTCAGC | CTATCCCCAA | GGCTCGTCGG | CCCGAGGGCA | GGACCTGGGC | TCAGCCCGGG |
| 53 | | 181 | AGACGTCAGC | CTATCCCCAA | GGCGCGTCGG | CCCGAGGGCA | GGACCTGGGC | TCAGCCCGGG |
| 54 | | 181 | AGACGTCAGC | CTATCCCTAA | GGCGCGTCGG | CCCGAGGGCA | GGACCTGGGC | TCAGCCCGGG |
| 55 | | 181 | AGACGTCAGC | CCATCCCCAA | GGCTCGTCGA | CCCGAGGGCA | GGACCTGGGC | TCAGCCCGGG |
| 56 | | 181 | AGACGTCAGC | CTATCCCCAA | GGCACGTCGG | CCCGAGGGTA | GGACCTGGGC | TCAGCCCGGG |
| 57 | | 181 | AGACGCCAGC | CTATCCCCAA | GGCGCGTCGG | CCCGAGGGCA | GGACCTGGGC | TCAGCCCGGG |
| 58 | GII | 181 | AGGCGACAAC | CTATCCCCAA | GGCTCGCCAG | CCCGAGGGCA | GGGCCTGGGC | TCAGCCCGGG |
| 59 | | 181 | AGGCGACAAC | CTATCCCCAA | GGCTCGCCAG | CCCGAGGGCA | GGGCCTGGGC | TCAGCCCGGG |
| 60 | | 181 | AGGCGACAAC | CTATCCCCAA | GGCTCGCCGG | CCCGAGGGCA | GGTCCTGGGC | TCAGCCCGGG |
| 61 | | 181 | AGGCGACAAC | CTATCCCCAA | GGCTCGCCAA | CCCGAGGGTA | GGGCCTGGGC | TCAGCCCGGG |
| 62 | | 181 | AGGCGACAAC | CTATCCCCAA | GGCTCGCCGG | CCCGAGGGCG | GGGCCTGGGC | TCAGCCCGGG |
| 63 | | 181 | AGGCGACAAC | CTATCCCCAA | GGCTCGCCGG | CCCGAGGGCA | GGGCCTGGGC | TCAGCCCGGG |
| 64 | | 181 | AGGCGCCAGC | CTATCCCCAA | GGCTCGCCAG | CCCGAGGGCA | GGGCCTGGGC | TCAGCCCGGG |
| 65 | GIII | 181 | AGGCGTCAGC | CCATCCCTAA | AGATCGTCGC | ACCGCTGGCA | AGTCCTGGGG | AAGGCCAGGA |
| 66 | | 181 | AGGCGCCAGC | CCATCCCCAA | AGATCGGCGC | ACCACTGGCA | AGTCCTGGGG | GAAGCCAGGA |

FIG. 5D

| SEQUENCE ID NUMBER | GENOTYPE | | | | | | | |
|---|---|---|---|---|---|---|---|---|
| 52 | GI | 241 | TACCCTTGGC | CCCTCTATGG | CAATGAGGGC | TGCGGGTGGG | CGGGATGGCT | CCTGTCTCCC |
| 53 | | 241 | TACCCTTGGC | CCCTCTATGG | CAATGAGGGT | TCCGGGTGGG | CGGGATGGCT | CCTGTCTCCC |
| 54 | | 241 | TACCCCTGGC | CCCTCTATGG | TAATGAGGGT | TGCGGATGGG | CGGGATGGCT | CCTGTCCCCC |
| 55 | | 241 | TACCCTTGGC | CCCTCTATGG | CAATGAGGGC | TGCGGGTGGG | CGGGATGGCT | CCTGTCTCCC |
| 56 | | 241 | TACCCTTGGC | CCCTCTATGG | CAATGAGGGT | TGCGGGTGGG | CGGGATGGCT | CCTGTCTCCC |
| 57 | | 241 | TACCCTTGGC | CCCTCTATGG | CAATGAGGGT | TGCGGGTGGG | CGGGATGGCT | CCTGTCTCCC |
| 58 | GII | 241 | TACCCTTGGC | CCCTCTATGG | CAATGAGGGT | ATGGGGTGGG | CAGGATGGCT | CCTGTCACCC |
| 59 | | 241 | TACCCTTGGC | CCCTCTATGG | CAACGAGGGT | ATGGGGTGGG | CAGGATGGCT | CCTGTCACCC |
| 60 | | 241 | TACCCTTGGC | CCCTCTATGG | CAACGAGGGT | ATGGGGTGGG | CAGGATGGCT | CCTGTCACCC |
| 61 | | 241 | TACCCTTGGC | CCCTCTATGG | CAATGAGGGT | ATGGGGTGGG | CAGGATGGCT | CCTGTCACCC |
| 62 | | 241 | TATCCTTGGC | CCCTCTATGG | CAATGAGGGT | CTGGGGTGGG | CAGGATGCT | CCTGTCACCC |
| 63 | | 241 | TACCCTTGGC | CCCTCTATGG | CAATGAGGGT | ATGGGGTGGG | CAGGATGGCT | CCTGTCACCC |
| 64 | | 241 | TACCCCTGGC | CCCTCTATGG | CAATGAGGGT | ATGGGGTGGG | CAGGATGGCT | CCTGTCACCC |
| 65 | GIII | 241 | TATCCTTGGC | CCCTGTATGG | GAATGAGGGT | CTCGGCTGGG | CAGGGTGGCT | CCTGTCCCCC |
| 66 | | 241 | TACCCTTGGC | CCCTGTATGG | GAATGAGGGT | CTCGGCTGGG | CAGGGTGGCT | CCTGTCCCCC |

FIG. 5E

| SEQUENCE ID NUMBER | GENOTYPE | | | | | | |
|---|---|---|---|---|---|---|---|
| 52 | GI | 301 | CGTGGCTCTC | GGCCTAGCTG | GGGCCCCACA | GACCCCCGGC | GTAGGTCGCG | CAATTTGGGT |
| 53 | | 301 | CGTGGCTCTC | GGCCTAGTTG | GGGCCCCACA | GACCCCCGGC | GTAGGTCGCG | CAATTTGGGT |
| 54 | | 301 | CGTGGCTCTC | GGCCTAGTTG | GGGCCCCTACA | GACCCCCGGC | GTAGGTCGCG | CAATTTGGGT |
| 55 | | 301 | CGTGGCTCTC | GGCCTAGCTG | GGGCCCCACA | GACCCCCGGC | GTAGGTCGCG | CAATTTGGGT |
| 56 | | 301 | CGCGGCTCTC | GGCCTAACTG | GGGCCCCACA | GACCCCCGGC | GTAGGTCGCG | CAATTTGGGT |
| 57 | | 301 | CGTGGCTCTC | GGCCTAGCTG | GGGCCCCACA | GACCCCCGGC | GTAGGTCGCG | CAATTTGGGT |
| 58 | GII | 301 | CGTGGCTCTC | GGCCTAGTTG | GGGCCCCACG | GACCCCCGGC | GTAGGTCGCG | TAATTTGGGT |
| 59 | | 301 | CGTGGCTCTC | GGCCTAGTTG | GGGCCCCACG | GACCCCCGGC | GTAGGTCGCG | TAATTTGGGT |
| 60 | | 301 | CGCGGCTCCC | GGCCTAGTTG | GGGCCCCACG | GACCCCCGGC | GTAGGTCGCG | TAATTTGGGT |
| 61 | | 301 | CGCGGCTCCC | GGCCTAGCTG | GGGCCCCACA | GACCCCCGGC | GTAGGTCGCG | TAATTTGGGT |
| 62 | | 301 | CGCGGCTCTC | GGCCTAGCTG | GGGCCCCTACC | GACCCCCGGC | GTAGGTCGCG | CAACTTGGGT |
| 63 | | 301 | CGTGGTTCTC | GGCCTAGTTG | GGGCCCCACG | GACCCCCGGC | GTAGGTCGCG | CAATTTGGGT |
| 64 | | 301 | CGCGGCTCCC | GGCCTAGTTG | GGGCCCCAAA | GACCCCCGGC | GTAGGTCGCG | TAATTTGGGT |
| 65 | GIII | 301 | CGTGGCTCTC | GCCCTTCATG | GGGCCCCACT | GACCCCCGGC | ATAGATCGCG | CAACTTGGGT |
| 66 | | 301 | CGCGGTTCTC | GCCCTTCATG | GGGCCCCACT | GACCCCCGGC | ATAGATCACG | CAACTTGGGT |

FIG. 5F

| SEQUENCE ID NUMBER | GENOTYPE | | | | | | | |
|---|---|---|---|---|---|---|---|---|
| 52 | GI  | 361 | AAGGTCATCG | ATACCCTTAC | GTGCGGCTTC | GCCGACCTCA | TGGGGTACAT | ACCGCTCGTC |
| 53 |     | 361 | AAGGTCATCG | ATACCCTTAC | GTGCGGCTTC | GCCGACCACA | TGGGGTACAT | ACCGCTCGTC |
| 54 |     | 361 | AAGGTCATCG | ATACCCTCAC | GTGCGGCTTC | GCCGACCACA | TGGGGTACAT | TCCGCTCGTT |
| 55 |     | 361 | AAGGTCATCG | ATACCCTTAC | GTGCGGCTTC | GCCGACCTCA | TGGGGTACAT | ACCGCTCGTC |
| 56 |     | 361 | AAGGTCATCG | ATACCCTTAC | GTGCGGCTTC | GCCGACCTCA | TGGGGTACAT | ACCGCTCGTC |
| 57 |     | 361 | AAGGTCATCG | ATACCCTTAC | GTGCGGCTTC | GCCGACCTCA | TGGGGTACAT | ACCGCTCGTC |
| 58 | GII | 361 | AAGGTCATCG | ATACCCTCAC | ATGCGGCTTC | GCCGACCTCA | TGGGGTACAT | TCCGCTCGTC |
| 59 |     | 361 | AAGGTCATCG | ATACCCTCAC | ATGCGGCTTC | GCCGACCTCA | TGGGGTACAT | TCCGCTTGTC |
| 60 |     | 361 | AAGGTCATCG | ATACCCTCAC | ATGCGGCTTC | GCCGACCTCA | TGGGGTACAT | TCCGCTCGTC |
| 61 |     | 361 | AAGGTCATCG | ATACCCTCAC | ATGCGGCTTC | GCCGACCTCA | TGGGGTACAT | TCCGCTCGTC |
| 62 |     | 361 | AAGGTCATCG | ATACCCTTAC | GTGCGGCTTC | GCCGACCTCA | TGGGGTACAT | TCCGCTCGTC |
| 63 |     | 361 | AAGATCATCG | ATACCCTTAC | GTGCGGCTTC | GCCGACCTCA | TGGGGTACAT | TCCGCTCGTC |
| 64 |     | 361 | AAGGTCATCG | ATACCCTCAC | ATGCGGCTTC | GCCGACCTCA | TGGGGTACAT | TCCGCTCGTC |
| 65 | GIII| 361 | AAGGTCATCG | ATACCCTAAC | GTGCGGTTTT | GCCGACCTCA | TGGGGTACAT | TCCGCTCATC |
| 66 |     | 361 | AAGGTCATCG | ATACCCTAAC | GTGTGGTTTT | GCCGACCTCA | TGGGGTACAT | TCCGTCGGT |

FIG. 5G

| SEQUENCE ID NUMBER | GENOTYPE | | | | | | | |
|---|---|---|---|---|---|---|---|---|
| 52 | GI | 421 | GGCGCCCCTC | TTGGAGGCGC | TGCCAGGGCC | CTGGCGCATG | GCGTCCGGGT | TCTGGAAGAC |
| 53 | | 421 | GGCGCCCCTC | TTGGAGGCGC | TGCCAGGGCT | CTGGCGCATG | GCGTCCGGGT | TCTGGAAGAC |
| 54 | | 421 | GGCGCCCCTC | TTGGGGGCGC | TGCCAGGGCC | CTGGCGCATG | GCGTCCGGGT | TCTGGAAGAC |
| 55 | | 421 | GGCGCCCCTC | TTGGAGGCGC | TGCCAGAGCC | CTGGCGCATG | GCGTCCGGGT | TCTGGAAGAC |
| 56 | | 421 | GGCGCCCCTC | TTGGAGGCGC | TGCCAGGGCC | CTGGCGCATG | GCGTCCGGGT | TCTGGAAGAC |
| 57 | | 421 | GGCGCCCCTC | TTGGAGGCGC | TGCCAGGGCC | CTGGCGCATG | GCGTCCGGGT | TCTGGAAGAC |
| 58 | GII | 421 | GGCGCCCCCC | TTAGGGGCGC | TGCCAGGGCC | TTGGCGCATG | GCGTCCGGGT | TCTGGAGGAC |
| 59 | | 421 | GGCGCCCCCC | TAGGGGGCGC | TGCCAGGGCC | CTGGCACATG | GTGTCCGGGT | TCTGGAGGAC |
| 60 | | 421 | GGCGCCCCCC | TAGGGGGCGC | TGCCAGGGCC | CTGGCACATG | GTGTCCGGGT | TCTGGAGGAC |
| 61 | | 421 | GGCGCCCCCC | TTGGGGGCGC | TGCCAGGGCC | CTGGCGCATG | GCGTCCGGGT | TCTGGAGGAC |
| 62 | | 421 | GGCGCCCCCC | TAGGGGGCGC | TGCCAGGGCC | CTGGCGCATG | GCGTCCGGGT | TCTGGAGGAC |
| 63 | | 421 | GGCGCCCCCC | TAGGGGGCGC | TGCCAGGGCC | CTGGCGCATG | GCGTCCGGGT | TCTGGAGGAC |
| 64 | | 421 | GGCGCCCCCT | TAGGGGGCGC | TGCCAGGGCC | CTGGCGCATG | GCGTCCGGGT | TCTGGAGGAC |
| 65 | GIII | 421 | GGCGCCCCCG | TTGGAGGCGT | TGCCAGAGCT | CTCGCCCACG | GAGTGAGGGT | TCTGGAGGAT |
| 66 | | 421 | GGTGCCCCCG | TTGGTGGTGT | CGCCAGAGCC | CTTGCCCATG | GGGTGAGGGT | TCTGGAAGAC |

FIG. 5H

| SEQUENCE ID NUMBER | GENOTYPE | | | | | | | | |
|---|---|---|---|---|---|---|---|---|---|
| 52 | GI | 481 | GGCGTGAACT | ATGCAACAGG | GAACCTTCCT | GGTTGCTCTT | TCTCTATCTT | CCTTCTGGCC | CTGCTCTCT |
| 53 | GI | 481 | GGCGTGAACT | ATGCAACAGG | GAACCTTCCT | GGTTGCTCTT | TCTCTATCTT | CCTTCTGGCC | CTGCTCTCT |
| 54 | GI | 481 | GGCGTGAACT | ATGCAACAGG | GAATCTTCCT | GGTTGCTCTT | TCTCTATCTT | CCTTCTGGCC | CTGCTCTCT |
| 55 | GI | 481 | GGCGTGAACT | ATGCAACAGG | GAACCTTCCT | GGTTGCTCTT | TCTCTATCTT | CCTTCTGGCC | CTGCTCTCT |
| 56 | GI | 481 | GGCGTGAACT | ATGCAACAGG | GAACCTTCCT | GGTTGCTCTT | TCTCTATCTT | CCTTCTGGCC | CTGCTCTCT |
| 57 | GI | 481 | GGCGTGAACT | ATGCAACAGG | GAACCTTCCT | GGTTGCTCTT | TTTCTATTTT | CCTTCTGGCC | CTGCTCTCT |
| 58 | GII | 481 | GGCGTGAACT | ACGCAACAGG | GAATCTGCCC | GGTTGCTCCT | TTTCTATCTT | CTGCTTGGCT | CTGCTGTCC |
| 59 | GII | 481 | GGCGTGAACT | ATGCAACAGG | GAATTTGCCT | GGTTGCTCTT | TCTCTATCTT | CCTTCTGGCT | CTGCTGTCC |
| 60 | GII | 481 | GGCGTGAACT | ATGCAACAGG | GAATTTGCCT | GGTTGCTCTT | TCTCTATCTT | CCTTCTGGCT | CTGCTGTCC |
| 61 | GII | 481 | GGCGTGAACT | ATGCAACAGG | GAATCTGCCC | GGTTGCTCTT | TCTCTATCTT | CCTTCTGGCT | TTGCTGTCC |
| 62 | GII | 481 | GGCGTGAACT | ATGCAACAGG | GAATTGCCC | GGTTGCTCTT | TCTCTATCTT | CCTTCTGGCT | TTGCTGTCC |
| 63 | GII | 481 | GGCGTGAACT | ATGCAACAGG | GAATCTGCCC | GGTTGCTCCT | TTTCTATCTT | CCTTCTGGCT | TTGCTGTCC |
| 64 | GII | 481 | GGCGTGAACT | ATGCAACAGG | GAATCTACCC | GGTTGCTCTT | TCTCTATCTT | CCTTCTGGCT | TTGCTGTCC |
| 65 | GIII | 481 | GGGTAAATT | ATGCAACAGG | GAATTGCCC | GGTTGCTCTT | TCTCTATCTT | TCTCTTAGCC | CTCTGTCT |
| 66 | GIII | 481 | GGGATAAATT | ATGCAACAGG | GAATCTGCCC | | | | |

549 Total

C0772/7000
/1845R

FIG. 5I

```
                        SEQUENCE LISTING (1) GENERAL INFORMATION:

(iii) NUMBER OF SEQUENCES:  147

(2) INFORMATION FOR SEQ ID NO: 1:

(i) SEQUENCE CHARACTERISTICS:
          (A) LENGTH:  340 nucleotides
          (B) TYPE:  nucleic acid
          (C) STRANDEDNESS:  single
          (D) TOPOLOGY:  linear (ii) MOLECULE TYPE:  DNA (vi) ORIGINAL SOURCE:   (ATCC # 40394)
          (C) INDIVIDUAL ISOLATE:  ns5hcv1

(xi) SEQUENCE DESCRIPTION: SEQ ID NO: 1:

CTCCACAGTC ACTGAGAGCG ACATCCGTAC GGAGGAGGCA                      40

ATCTACCAAT GTTGTGACCT CGACCCCCAA GCCCGCGTGG                      80

CCATCAAGTC CCTCACCGAG AGGCTTTATG TTGGGGGCCC                     120

TCTTACCAAT TCAAGGGGGG AGAACTGCGG CTATCGCAGG                     160

TGCCGCGCGA GCGGCGTACT GACAACTAGC TGTGGTAACA                     200

CCCTCACTTG CTACATCAAG GCCCGGGCAG CCTGTCGAGC                     240

CGCAGGGCTC CAGGACTGCA CCATGCTCGT GTGTGGCGAC                     280

GACTTAGTCG TTATCTGTGA AAGCGCGGGG GTCCAGGAGG                     320

ACGCGGCGAG CCTGAGAGCC                                           340

(2) INFORMATION FOR SEQ ID NO: 2:

(i) SEQUENCE CHARACTERISTICS:
          (A) LENGTH:  340 nucleotides
          (B) TYPE:  nucleic acid
          (C) STRANDEDNESS:  single
          (D) TOPOLOGY:  linear (ii) MOLECULE TYPE:  DNA (vi) ORIGINAL SOURCE:
```

(C) INDIVIDUAL ISOLATE: ns5i21

(xi) SEQUENCE DESCRIPTION: SEQ ID NO: 2:

| | |
|---|---:|
| CTCCACAGTC ACTGAGAGCG ACATCCGTAC GGAGGAGGCA | 40 |
| ATTTACCAAT GTTGTGACCT GGACCCCCAA GCCCGCATGG | 80 |
| CCATCAAGTC CCTCACTGAG AGGCTTTATG TCGGGGCCC | 120 |
| TCTTACCAAT TCAAGGGGGG AGAACTGCGG CTACCGCAGG | 160 |
| TGCCGCGCGA GCGGCGTACT GACAACTAGC TGTGGTAACA | 200 |
| CCCTCACTTG CTACATCAAG GCCCGGGCAG CCTGTCGAGC | 240 |
| CGCAGGGCTC CAGGACTGCA CCATGCTTGT GTGTGGCGAC | 280 |
| GACTTAGTCG TTATCTGTGA AAGTGCGGGG GTCCAGGAGG | 320 |
| ACGCGGCGAG CCTGAGAGCC | 340 |

(2) INFORMATION FOR SEQ ID NO: 3:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5pt1

(xi) SEQUENCE DESCRIPTION: SEQ ID NO: 3:

| | |
|---|---:|
| CTCCACAGTC ACTGAGAGCG ACATCCGTAC GGAGGAGGCA | 40 |
| ATCTACCAAT GTTGTGATCT GGACCCCCAA GCCCGCGTGG | 80 |
| CCATCAAGTC CCTCACTGAG AGGCTTTACG TTGGGGGCCC | 120 |
| TCTTACCAAT TCAAGGGGGG AGAACTGCGG CTACCGCAGG | 160 |
| TGCCGGGCGA GCGGCGTACT GACAACTAGC TGTGGTAATA | 200 |
| CCCTCACTTG CTACATCAAG GCCCGGGCAG CCTGTCGAGC | 240 |
| CGCAGGGCTC CGGGACTGCA CCATGCTCGT GTGTGGTGAC | 280 |
| GACTTGGTCG TTATCTGTGA GAGTGCGGGG GTCCAGGAGG | 320 |
| ACGCGGCGAG CCTGAGAGCC | 340 |

(2) INFORMATION FOR SEQ ID NO:4:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5gm2

(xi) SEQUENCE DESCRIPTION: SEQ ID NO: 4:

| | |
|---|---:|
| CTCTACAGTC ACTGAGAACG ACATCCGTAC GGAGGAGGCA | 40 |
| ATTTACCAAT GTTGTGACCT GGACCCCCAA GCCCGCGTGG | 80 |
| CCATCAAGTC CCTCACTGAG AGGCTTTATG TTGGGGGCCC | 120 |
| CCTTACCAAT TCAAGGGGGG AAAACTGCGG CTATCGCAGG | 160 |

```
TGCCGCGCGA GCGGCGTACT GACAACTAGC TGTGGTAACA                200

CCCTCACTTG CTACATTAAG GCCCGGGCAG CCTGTCGAGC                240

CGCAGGGCTC CAGGACTGCA CCATGCTCGT GTGTGGCGAC                280

GACTTAGTCG TTATCTGTGA GAGTGCGGGA GTCCAGGAGG                320

ACGCGGCGAA CTTGAGAGCC                                      340
```

(2) INFORMATION FOR SEQ ID NO:5:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5us17

(xi) SEQUENCE DESCRIPTION: SEQ ID NO: 5:

```
CTCCACAGTC ACTGAGAGCG ATATCCGTAC GGAGGAGGCA                40

ATCTACCAGT GTTGTGACCT GGACCCCCAA GCCCGCGTGG                80

CCATCAAGTC CCTCACCGAG AGGCTTTATG TCGGGGGCCC                120

TCTTACCAAT TCAAGGGGGG AAAACTGCGG CTATCGCAGG                160

TGCCGCGCAA GCGGCGTACT GACAACTAGC TGTGGTAACA                200

CCCTCACTTG TTACATCAAG GCCCAAGCAG CCTGTCGAGC                240

CGCAGGGCTC CGGGACTGCA CCATGCTCGT GTGTGGCGAC                280

GACTTAGTCG TTATCTGTGA AAGTCAGGGA GTCCAGGAGG                320

ATGCAGCGAA CCTGAGAGCC                                      340
```

(2) INFORMATION FOR SEQ ID NO:6:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5sp2

(xi) SEQUENCE DESCRIPTION: SEQ ID NO: 6:

```
CTCTACAGTC ACTGAGAGCG ATATCCGTAC GGAGGAGGCA                40

ATCTACCAAT GTTGTGACCT GGACCCCGAA GCCCGTGTGG                80

CCATCAAGTC CCTCACTGAG AGGCTTTATG TTGGGGGCCC                120

TCTTACCAAT TCAAGGGGGG AGAACTGCGG CTACCGCAGG                160

TGCCGCGCAA GCGGCGTACT GACGACTAGC TGTGGTAATA                200

CCCTCACTTG TTACATCAAG GCCCGGGCAG CCTGTCGAGC                240

CGCAGGGCTC CAGGACTGCA CCATGCTCGT GTGTGGCGAC                280

GACCTAGTCG TTATCTGCGA AAGTGCGGGG GTCCAGGAGG                320

ACGCGGCGAG CCTGAGAGCC                                      340
```

(2) INFORMATION FOR SEQ ID NO:7:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5j1

(xi) SEQUENCE DESCRIPTION: SEQ ID NO: 7:

```
CTCCACAGTC ACTGAGAATG ACACCCGTGT TGAGGAGTCA                          40
ATTTACCAAT GTTGTGACTT GGCCCCCGAA GCCAGACAGG                          80
CCATAAGGTC GCTCACAGAG CGGCTCTATG TCGGGGGTCC                         120
TATGACTAAC TCCAAAGGGC AGAACTGCGG CTATCGCCGG                         160
TGCCGCGCGA GCGGCGTGCT GACGACTAGC TGCGGTAATA                         200
CCCTCACATG CTACCTGAAG GCCACAGCGG CCTGTCGAGC                         240
TGCCAAGCTC CAGGACTGCA CGATGCTCGT GAACGGAGAC                         280
GACCTTGTCG TTATCTGTGA AAGCGCGGGG AACCAAGAGG                         320
ACGCGGCAAG CCTACGAGCC                                               340
```

(2) INFORMATION FOR SEQ ID NO:8:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5k1

(xi) SEQUENCE DESCRIPTION: SEQ ID NO: 8:

```
CTCAACGGTC ACTGAGAATG ACATCCGTGT TGAGGAGTCA                          40
ATTTACCAAA GTTGTGACTT GGCCCCCGAG GCCAGACAAG                          80
CCATAAGGTC GCTCACAGAG CGGCTTTACA TCGGGGGCCC                         120
CCTGACTAAT TCAAAAGGGC AGAACTGCGG CTATCGCCGA                         160
TGCCGCGCCA GCGGTGTGCT GACGACTAGC TGCGGTAATA                         200
CCCTCACATG TTACTTGAAG GCCACTGCGG CCTGTAGAGC                         240
TGCGAAGCTC CAGGACTGCA CGATGCTCGT GTGCGGAGAC                         280
GACCTTGTCG TTATCTGTGA AAGCGCGGGA ACCCAGGAGG                         320
ATGCGGCGAG CCTACGAGTC                                               340
```

(2) INFORMATION FOR SEQ ID NO:9:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
              (C) INDIVIDUAL ISOLATE: ns5k1.1

(xi) SEQUENCE DESCRIPTION: SEQ ID NO: 9:

| | |
|---|---|
| CTCAACGGTC ACCGAGAATG ACATCCGTGT TGAGGAGTCA | 40 |
| ATTTATCAAT GTTGTGCCTT GGCCCCCGAG GCTAGACAGG | 80 |
| CCATAAGGTC GCTCACAGAG CGGCTTTATA TCGGGGCCC | 120 |
| CCTGACCAAT TCAAAGGGGC AGAACTGCGG TTATCGCCGG | 160 |
| TGCCGCGCCA GCGGCGTACT GACGACCAGC TGCGGTAATA | 200 |
| CCCTTACATG TTACTTGAAG GCCTCTGCAG CCTGTCGAGC | 240 |
| CGCGAAGCTC CAGGACTGCA CGATGCTCGT GTGTGGGGAC | 280 |
| GACCTTGTCG TTATCTGTGA AAGCGCGGGA ACCCAGGAGG | 320 |
| ACGCGGCGAA CCTACGAGTC | 340 |

(2) INFORMATION FOR SEQ ID NO:10:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5gh6

(xi) SEQUENCE DESCRIPTION: SEQ ID NO: 10:

| | |
|---|---|
| CTCAACGGTC ACTGAGAGTG ACATCCGTGT CGAGGAGTCG | 40 |
| ATTTACCAAT GTTGTGACTT GGCCCCCGAA GCCAGGCAGG | 80 |
| CCATAAGGTC GCTCACCGAG CGACTTTATA TCGGGGCCC | 120 |
| CCTGACTAAT TCAAAAGGGC AGAACTGCGG TTATCGCCGG | 160 |
| TGCCGCGCGA GCGGCGTGCT GACGACTAGC TGCGGTAATA | 200 |
| CCCTCACATG TTACTTGAAG GCCTCTGCAG CCTGTCGAGC | 240 |
| TGCAAAGCTC CAGGACTGCA CGATGCTCGT GAACGGGGAC | 280 |
| GACCTTGTCG TTATCTGCGA GAGCGCGGGA ACCCAAGAGG | 320 |
| ACGCGGCGAG CCTACGAGTC | 340 |

(2) INFORMATION FOR SEQ ID NO:11:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5sp1

(xi) SEQUENCE DESCRIPTION: SEQ ID NO: 11:

| | |
|---|---|
| CTCCACAGTC ACTGAGAGTG ACATCCGTGT TGAGGAGTCA | 40 |
| ATTTACCAAT GTTGTGACTT GGCCCCCGAA GCCAGACAGG | 80 |
| CTATAAGGTC GCTCACAGAG CGGCTGTACA TCGGGGTCC | 120 |

| | |
|---|---|
| CCTGACTAAT TCAAAAGGGC AGAACTGCGG CTATCGCCGG | 160 |
| TGCCGCGCAA GCGGCGTGCT GACGACTAGC TGCGGTAACA | 200 |
| CCCTCACATG TTACTTGAAG GCCTCTGCGG CCTGTCGAGC | 240 |
| TGCGAAGCTC CAGGACTGCA CGATGCTCGT GTGCGGTGAC | 280 |
| GACCTTGTCG TTATCTGTGA GAGCGCGGGA ACCCAAGAGG | 320 |
| ACGCGGCGAG CCTACGAGTC | 340 |

(2) INFORMATION FOR SEQ ID NO:12:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5sp3

(xi) SEQUENCE DESCRIPTION: SEQ ID NO: 12:

| | |
|---|---|
| CTCAACAGTC ACTGAGAGTG ACATCCGTGT TGAGGAGTCA | 40 |
| ATCTACCAAT GTTGTGACTT GGCCCCCGAA GCCAGACAGG | 80 |
| CTATAAGGTC GCTCACAGAG CGGCTTTACA TCGGGGTCC | 120 |
| CCTGACTAAT TCAAAAGGGC AGAACTGCGG CTATCGCCGG | 160 |
| TGCCGCGCAA GCGGCGTGCT GACGACTAGC TGCGGTAATA | 200 |
| CCCTCACATG TTACCTGAAG GCCAGTGCGG CCTGTCGAGC | 240 |
| TGCGAAGCTC CAGGACTGCA CAATGCTCGT GTGCGGTGAC | 280 |
| GACCTTGTCG TTATCTGTGA GAGCGCGGGG ACCCAAGAGG | 320 |
| ACGCGGCGAG CCTACGAGTC | 340 |

(2) INFORMATION FOR SEQ ID NO:13:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5k2

(xi) SEQUENCE DESCRIPTION: SEQ ID NO: 13:

| | |
|---|---|
| CTCAACCGTC ACTGAGAGAG ACATCAGAAC TGAGGAGTCC | 40 |
| ATATACCGAG CCTGCTCCCT GCCTGAGGAG GCTCACATTG | 80 |
| CCATACACTC GCTGACTGAG AGGCTCTACG TGGGAGGGCC | 120 |
| CATGTTCAAC AGCAAGGGCC AGACCTGCGG GTACAGGCGT | 160 |
| TGCCGCGCCA GCGGGGTGCT CACCACTAGC ATGGGAACA | 200 |
| CCATCACATG CTATGTAAAA GCCCTAGCGG CTTGCAAGGC | 240 |
| TGCAGGGATA GTTGCACCCT CAATGCTGGT ATGCGGCGAC | 280 |
| GACTTAGTTG TCATCTCAGA AAGCCAGGGG ACTGAGGAGG | 320 |
| ACGAGCGGAA CCTGAGAGCT | 340 |

(2) INFORMATION FOR SEQ ID NO:14:

(i) SEQUENCE CHARACTERISTICS:
       (A) LENGTH: 340 nucleotides
       (B) TYPE: nucleic acid
       (C) STRANDEDNESS: single
       (D) TOPOLOGY: linear (ii) MOLECULE TYPE: DNA (vi) ORIGINAL SOURCE:
       (C) INDIVIDUAL ISOLATE: ns5arg8

(xi) SEQUENCE DESCRIPTION: SEQ ID NO: 14:

```
CTCTACAGTC ACGTAAAAGG ACATCACATC CTAGGAGTCC                40
ATCTACCAGT CCTGTTCACT GCCCGAGGAG GCTCGAACTG                80
CTATACACTC ACTGACTGAG AGACTATACG TAGGGGGGCC               120
CATGACAAAC AGCAAGGGCC AATCCTGCGG GTACAGGCGT               160
TGCCGCGCGA GCGCAGTGCT CACCACCAGC ATGGGCAACA               200
CACTCACGTG CTACGTAAAA GCCAGGGCGG CGTGTAACGC               240
CGCGGGATT GTTGCTCCCA CCATGCTGGT GTGCGGTGAC                280
GACCTGGTCG TCATCTCAGA GAGTCAAGGG GCTGAGGAGG               320
ACGAGCAGAA CCTGAGAGTC                                     340
```

(2) INFORMATION FOR SEQ ID NO:15:

(i) SEQUENCE CHARACTERISTICS:
       (A) LENGTH: 340 nucleotides
       (B) TYPE: nucleic acid
       (C) STRANDEDNESS: single
       (D) TOPOLOGY: linear (ii) MOLECULE TYPE: DNA (vi) ORIGINAL SOURCE:
       (C) INDIVIDUAL ISOLATE: ns5i10

(xi) SEQUENCE DESCRIPTION: SEQ ID NO: 15:

```
CTCTACAGTC ACAGAGAGGG ACATCAGAAC CGAGGAGTCC                40
ATCTATCTGT CCTGCTCACT GCCTGAGGAG GCCCGAACTG                80
CTATACACTC ACTGACTGAG AGACTGTACG TAGGGGGGCC               120
CATGACAAAC AGCAAGGGGC AATCCTGCGG GTACAGGCGT               160
TGCCGCGCGA GCGGAGTGCT CACCACCAGC ATGGGCAACA               200
CGCTCACGTG CTACGTGAAA GCCAGAGCGG CGTGTAACGC               240
CGCGGGCATT GTTGCTCCCA CCATGTTGGT GTGCGGCGAC               280
GACCTGGTTG TCATCTCAGA GAGTCAGGGG GTCGAGGAAG               320
ATGAGCGGAA CCTGAGAGTC                                     340
```

(2) INFORMATION FOR SEQ ID NO:16:

(i) SEQUENCE CHARACTERISTICS:
       (A) LENGTH: 340 nucleotides
       (B) TYPE: nucleic acid
       (C) STRANDEDNESS: single
       (D) TOPOLOGY: linear (ii) MOLECULE TYPE: DNA (vi) ORIGINAL SOURCE:
    (C) INDIVIDUAL ISOLATE: ns5arg6

(xi) SEQUENCE DESCRIPTION: SEQ ID NO: 16:

| | |
|---|---:|
| CTCTACAGTC ACGGAGAGGG ACATCAGAAC CGAGGAGTCC | 40 |
| ATCTATCTGT CCTGTTCACT GCCTGAGGAG GCTCGAACTG | 80 |
| CCATACACTC ACTGACTGAG AGGCTGTACG TAGGGGGGCC | 120 |
| CATGACAAAC AGCAAAGGGC AATCCTGCGG GTACAGGCGT | 160 |
| TGCCGCGCGA GCGGAGTGCT CACCACCAGC ATGGGTAACA | 200 |
| CACTCACGTG CTACGTGAAA GCTAAAGCGG CATGTAACGC | 240 |
| CGCGGGCATT GTTGCCCCCA CCATGTTGGT GTGCGGCGAC | 280 |
| GACCTAGTCG TCATCTCAGA GAGTCAAGGG GTCGAGGAGG | 320 |
| ATGAGCGAAA CCTGAGAGCT | 340 |

(2) INFORMATION FOR SEQ ID NO:17:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5k2b (xi) SEQUENCE DESCRIPTION: SEQ ID NO: 17:

| | |
|---|---:|
| CTCAACCGTC ACGGAGAGGG ACATAAGAAC AGAAGAATCC | 40 |
| ATATATCAGG GTTGTTCCCT GCCTCAGGAG GCTAGAACTG | 80 |
| CTATCCACTC GCTCACTGAG AGACTCTACG TAGGAGGGCC | 120 |
| CATGACAAAC AGCAAGGGAC AATCCTGCGG TTACAGGCGT | 160 |
| TGCCGCGCCA GCGGGGTCTT CACCACCAGC ATGGGGAATA | 200 |
| CCATGACATG CTACATCAAA GCCCTTGCAG CGTGCAAAGC | 240 |
| TGCAGGGATC GTGGACCCTA TCATGCTGGT GTGTGGAGAC | 280 |
| GACCTGGTCG TCATCTCGGA GAGCGAAGGT AACGAGGAGG | 320 |
| ACGAGCGAAA CCTGAGAGCT | 340 |

(2) INFORMATION FOR SEQ ID NO:18:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5sa283

(xi) SEQUENCE DESCRIPTION: SEQ ID NO: 18:

| | |
|---|---:|
| CTCGACCGTT ACCGAACATG ACATAATGAC TGAAGAGTCT | 40 |
| ATTTACCAAT CATTGTACTT GCAGCCTGAG GCGCGTGTGG | 80 |
| CAATACGGTC ACTCACCCAA CGCCTGTACT GTGGAGGCCC | 120 |

```
CATGTATAAC AGCAAGGGGC AACAATGTGG TTATCGTAGA                             160

TGCCGCGCCA GCGGCGTCTT CACCACTAGT ATGGGCAACA                             200

CCATGACGTG CTACATTAAG GCTTTAGCCT CCTGTAGAGC                             240

CGCAAAGCTC CAGGACTGCA CGCTCCTGGT GTGTGGTGAT                             280

GATCTTGTGG CCATTTGCGA GAGCCAGGGG ACGCACGAGG                             320

ATAAAGCGAG CCTGAGAGCC                                                   340
```

(2) INFORMATION FOR SEQ ID NO:19:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5sa156

(xi) SEQUENCE DESCRIPTION: SEQ ID NO: 19:

```
CTCGACCGTT ACCGAACATG ACATAATGAC TGAAGAGTCC                              40

ATTTACCAAT CATTGTACTT GCAGCCTGAG GCACGCGCGG                              80

CAATACGGTC ACTCACCCAA CGCCTGTACT GTGGAGGCCC                             120

CATGTATAAC AGCAAGGGGC AACAATGTGG TTACCGTAGA                             160

TGCCGCGCCA GCGGCGTCTT CACCACCAGT ATGGGCAACA                             200

CCATGACGTG CTACATCAAG GCTTCAGCCG CCTGTAGAGC                             240

TGCAAAGCTC CAGGACTGCA CGCTCCTGGT GTGTGGTGTG                             280

ACCTTGGTGG CCATTTGCGA GAGCCAAGGG ACGCACGAGG                             320

ATGAAGCGTG CCTGAGAGTC                                                   340
```

(2) INFORMATION FOR SEQ ID NO:20:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5il1

(xi) SEQUENCE DESCRIPTION: SEQ ID NO: 20:

```
CTCTACTGTC ACTGAACAGG ACATCAGGGT GGAAGAGGAG                              40

ATATACCAGT GCTGTAACCT TGAACCGGAG GCCAGGAAAG                              80

TGATCTCCTC CCTCACGGAG CGGCTTTACT GCGGGGGCCC                             120

TATGTTCAAC AGCAAGGGGG CCCAGTGTGG TTATCGCCGT                             160

TGCCGTGCTA GTGGAGTCCT GCCTACCAGC TTCGGCAACA                             200

CAATCACTTG TTACATCAAG GCTAGAGCGG CTTCGAAGGC                             240

CGCAGGCCTC CGGAACCCGG ACTTTCTTGT CTGCGGAGAT                             280

GATCTGGTCG TGGTGGCTGA GAGTGATGGC GTCGACGAGG                             320
```

| | |
|---|---|
| ATAGAGCAGC CCTGAGAGCC | 340 |

(2) INFORMATION FOR SEQ ID NO:21:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5i4

(xi) SEQUENCE DESCRIPTION: SEQ ID NO: 21:

| | |
|---|---|
| CTCGACTGTC ACTGAACAGG ACATCAGGGT GGAAGAGGAG | 40 |
| ATATACCAAT GCTGTAACCT TGAACCGGAG GCCAGGAAAG | 80 |
| TGATCTCCTC CCTCACGGAG CGGCTTTACT GCGGGGGCCC | 120 |
| TATGTTCAAT AGCAAGGGGG CCCAGTGTGG TTATCGCCGT | 160 |
| TGCCGTGCTA GTGGAGTTCT GCCTACCAGC TTCGGCAACA | 200 |
| CAATCACTTG TTACATCAAG GCTAGAGCGG CTGCGAAGGC | 240 |
| CGCAGGGCTC CGGACCCCGG ACTTTCTCGT CTGCGGAGAT | 280 |
| GATCTGGTTG TGGTGGCTGA GAGTGATGGC GTCGACGAGG | 320 |
| ATAGAACAGC CCTGCGAGCC | 340 |

(2) INFORMATION FOR SEQ ID NO:22:

(i) SEQUENCE CHARACTERISTICS:
        (A) LENGTH: 340 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ns5gh8

(xi) SEQUENCE DESCRIPTION: SEQ ID NO: 22:

| | |
|---|---|
| CTCAACTGTC ACTGAACAGG ACATCAGGGT GGAAGAGGAG | 40 |
| ATATACCAAT GCTGTAACCT TGAACCGGAG GCCAGGAAAG | 80 |
| TGATCTCCTC CCTCACGGAA CGGCTTTACT GCGGGGGCCC | 120 |
| TATGTTCAAC AGCAAGGGGG CCCAGTGTGG TTATCGCCGT | 160 |
| TGCCGTGCCA GTGGAGTTCT GCCTACCAGC TTCGGCAACA | 200 |
| CAATCACTTG TTACATCAAA GCTAGAGCGG CTGCCGAAGC | 240 |
| CGCAGGCCTC CGGAACCCGG ACTTTCTTGT CTGCGGAGAT | 280 |
| GATCTGGTTG TGGTGGCTGA GAGTGATGGC GTCAATGAGG | 320 |
| ATAGAGCAGC CCTGGGAGCC | 340 |

(2) INFORMATION FOR SEQ ID NO:23:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE: (ATCC # 40394)
    (C) INDIVIDUAL ISOLATE: hcv1

(xi) SEQUENCE DESCRIPTION: SEQ ID NO: 23:

```
GACGGCGTTG GTAATGGCTC AGCTGCTCCG GATCCCACAA                              40
GCCATCTTGG ACATGATCGC TGGTGCTCAC TGGGGAGTCC                              80
TGGCGGGCAT AGCGTATTTC                                                   100
```

(2) INFORMATION FOR SEQ ID NO:24:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: US5

(xi) SEQUENCE DESCRIPTION: SEQ ID NO: 24:

```
GACGGCGTTG GTGGTAGCTC AGGTACTCCG GATCCCACAA                              40
GCCATCATGG ACATGATCGC TGGAGCCCAC TGGGGAGTCC                              80
TGGCGGGCAT AGCGTATTTC                                                   100
```

(2) INFORMATION FOR SEQ ID NO:25:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: AUS5

(xi) SEQUENCE DESCRIPTION: SEQ ID NO: 25:

```
AACGGCGCTG GTAGTAGCTC AGCTGCTCAG GGTCCCGCAA                              40
GCCATCGTGG ACATGATCGC TGGTGCCCAC TGGGGAGTCC                              80
TAGCGGGCAT AGCGTATTTT                                                   100
```

(2) INFORMATION FOR SEQ ID NO:26:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: US4

(xi) SEQUENCE DESCRIPTION: SEQ ID NO: 26:

```
GACAGCCCTA GTGGTATCGC AGTTACTCCG GATCCCACAA                              40
GCCGTCATGG ATATGGTGGC GGGGGCCCAC TGGGGAGTCC                              80
TGGCGGGCCT TGCCTACTAT                                                   100
```

(2) INFORMATION FOR SEQ ID NO:27:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: ARG2

(xi) SEQUENCE DESCRIPTION: SEQ ID NO: 27:

```
AGCAGCCCTA GTGGTGTCGC AGTTACTCCG GATCCCACAA                40
AGCATCGTGG ACATGGTGGC GGGGGCCCAC TGGGGAGTCC                80
TGGCGGGCCT TGCTTACTAT                                     100
```

(2) INFORMATION FOR SEQ ID NO:28:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: I15

(xi) SEQUENCE DESCRIPTION: SEQ ID NO: 28:

```
GGCAGCCCTA GTGGTGTCGC AGTTACTCCG GATCCCGCAA                40
GCTGTCGTGG ACATGGTGGC GGGGGCCCAC TGGGGAATCC                80
TAGCGGGTCT TGCCTACTAT                                     100
```

(2) INFORMATION FOR SEQ ID NO:29:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: GH8

(xi) SEQUENCE DESCRIPTION: SEQ ID NO: 29:

```
TGTGGGTATG GTGGTGGCGC ACGTCCTGCG TTTGCCCCAG                40
ACCTTGTTCG ACATAATAGC CGGGGCCCAT TGGGGCATCT                80
TGGCGGGCTT GGCCTATTAC                                     100
```

(2) INFORMATION FOR SEQ ID NO:30:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: I4

(xi) SEQUENCE DESCRIPTION: SEQ ID NO: 30:

```
TGTGGGTATG GTGGTAGCAC ACGTCCTGCG TCTGCCCCAG          40
ACCTTGTTCG ACATAATAGC CGGGGCCCAT TGGGGCATCT          80
TGGCAGGCCT AGCCTATTAC                               100
```

(2) INFORMATION FOR SEQ ID NO:31:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: I11

(xi) SEQUENCE DESCRIPTION: SEQ ID NO: 31:

```
TGTGGGTATG GTGGTGGCGC AAGTCCTGCG TTTGCCCCAG          40
ACCTTGTTCG ACGTGCTAGC CGGGGCCCAT TGGGGCATCT          80
TGGCGGGCCT GGCCTATTAC                               100
```

(2) INFORMATION FOR SEQ ID NO:32:

(i) SEQUENCE CHARACTERISTICS:
        (A) LENGTH: 100 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: I10

(xi) SEQUENCE DESCRIPTION: SEQ ID NO: 32:

```
TACCACTATG CTCCTGGCAT ACTTGGTGCG CATCCCGGAG          40
GTCATCCTGG ACATTATCAC GGGAGGACAC TGGGGCGTGA          80
TGTTTGGCCT GGCTTATTTC                               100
```

(2) INFORMATION FOR SEQ ID NO:33:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE: (ATCC # 40394)
        (C) INDIVIDUAL ISOLATE: hcv1

(xi) SEQUENCE DESCRIPTION: SEQ ID NO: 33:

```
GTTAGTATGA GTGTCGTGCA GCCTCCAGGA CCCCCCCTCC          40
CGGGAGAGCC ATAGTGGTCT GCGGAACCGG TGAGTACACC          80
GGAATTGCCA GGACGACCGG GTCCTTTCTT GGATCAACCC         120
GCTCAATGCC TGGAGATTTG GGCGTGCCCC CGCAAGACTG         160
CTAGCCGAGT AGTGTTGGGT CGCGAAAGGC CTTGTGGTAC         200
```

```
TGCCTGATAG GGTGCTTGCG AGTGCCCCGG GAGGTCTCGT                      240

AGACCGTGCA CC                                                    252
```

(2) INFORMATION FOR SEQ ID NO:34:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: us5

(xi) SEQUENCE DESCRIPTION: SEQ ID NO: 34:

```
GTTAGTATGA GTGTCGTGCA GCCTCCAGGA CCCCCCCTCC                       40

CGGGAGAGCC ATAGTGGTCT GCGGAACCGG TGAGTACACC                       80

GGAATTGCCA GGACGACCGG GTCCTTTCTT GGATCAACCC                      120

GCTCAATGCC TGGAGATTTG GGCGTGCCCC CGCAAGACTG                      160

CTAGCCGAGT AGTGTTGGGT CGCGAAAGGC CTTGTGGTAC                      200

TGCCTGATAG GGTGCTTGCG AGTGCCCCGG GAGGTCTCGT                      240

AGACCGTGCA CC                                                    252
```

(2) INFORMATION FOR SEQ ID NO:35:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: aus1

(xi) SEQUENCE DESCRIPTION: SEQ ID NO: 35:

```
GTTAGTATGA GTGTCGTGCA GCCTCCAGGA CCCCCCCTCC                       40

CGGGAGAGCC ATAGTGGTCT GCGGAACCGG TGAGTACACC                       80

GGAATTGCCA GGACGACCGG GTCCTTTCTT GGATCAACCC                      120

GCTCAATGCC TGGAGATTTG GGCACGCCCC CGCAAGATCA                      160

CTAGCCGAGT AGTGTTGGGT CGCGAAAGGC CTTGTGGTAC                      200

TGCCTGATAG GGTGCTTGCG AGTGCCCCGG GAGGTCTCGT                      240

AGACCGTGCA CC                                                    252
```

(2) INFORMATION FOR SEQ ID NO:36:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: sp2

(xi) SEQUENCE DESCRIPTION: SEQ ID NO: 36:

```
GTTAGTATGA GTGTCGTGCA GCCTCCAGGA CCCCCCCTCC                      40

CGGGAGAGCC ATAGTGGTCT GCGGAACCGG TGAGTACACC                      80

GGAATTGCCA GGACGACCGG GTCCTTTCTT GGATAAACCC                     120

GCTCAATGCC TGGAGATTTG GGCGTGCCCC CGCGAGACTG                     160

CTAGCCGAGT AGTGTTGGGT CGCGAAAGGC CTTGTGGTAC                     200

TGCCTGATAG GGTGCTTGCG AGTGCCCCGG GAGGTCTCGT                     240

AGACCGTGCA CC                                                   252
```

(2) INFORMATION FOR SEQ ID NO:37:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: gm2

(xi) SEQUENCE DESCRIPTION: SEQ ID NO: 37:

```
GTTAGTATGA GTGTCGTGCA GCCTCCAGGA CCCCCCCTCC                      40

CGGGAGAGCC ATAGTGGTCT GCGGAACCGG TGAGTACACC                      80

GGAATTGCCA GGACGACCGG GTCCTTTCTT GGATCAACCC                     120

GCTCAATGCC TGGAGATTTG GGCGTGCCCC CGCAAGACTG                     160

CTAGCCGAGT AGTGTTGGGT CGCGAAAGGC CTTGTGGTAC                     200

TGCCTGATAG GGTGCTTGCG AGTGCCCCGG GAGGTCTCGT                     240

AGACCGTGCA CC                                                   252
```

(2) INFORMATION FOR SEQ ID NO:38:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: i21

(xi) SEQUENCE DESCRIPTION: SEQ ID NO: 38:

```
GTTAGTATGA GTGTCGTGCA GCCTCCAGGA CCCCCCCTCC                      40

CGGGAGAGCC ATAGTGGTCT GCGGAACCGG TGAGTACACC                      80

GGAATTGCCA GGACGACCGG GTCCTTTCTT GGATAAACCC                     120

GCTCAATGCC TGGAGATTTG GGCGTGCCCC CGCAAGACTG                     160

CTAGCCGAGT AGTGTTGGGT CGCGAAAGGC CTTGTGGTAC                     200

TGCCTGATAG GGTGCTTGCG AGTGCCCCGG GAGGTCTCGT                     240

AGACCGTGCA CC                                                   252
```

(2) INFORMATION FOR SEQ ID NO:39:

(i) SEQUENCE CHARACTERISTICS:

(A) LENGTH: 252 nucleotides
(B) TYPE: nucleic acid
(C) STRANDEDNESS: single
(D) TOPOLOGY: linear (ii) MOLECULE TYPE: DNA (vi) ORIGINAL SOURCE:
(C) INDIVIDUAL ISOLATE: us4

(xi) SEQUENCE DESCRIPTION: SEQ ID NO: 39:

| | | |
|---|---|---|
| GTTAGTATGA GTGTCGTGCA GCCTCCAGGA CCCCCCCTCC | | 40 |
| CGGGAGAGCC ATAGTGGTCT GCGGAACCGG TGAGTACACC | | 80 |
| GGAATTGCCA GGACGACCGG GTCCTTTCTT GGATCAACCC | | 120 |
| GCTCAATGCC TGGAGATTTG GGCGTGCCCC CGCGAGACTG | | 160 |
| CTAGCCGAGT AGTGTTGGGT CGCGAAAGGC CTTGTGGTAC | | 200 |
| TGCCTGATAG GGTGCTTGCG AGTGCCCCGG GAGGTCTCGT | | 240 |
| AGACCGTGCA CC | | 252 |

(2) INFORMATION FOR SEQ ID NO:40:

(i) SEQUENCE CHARACTERISTICS:
(A) LENGTH: 252 nucleotides
(B) TYPE: nucleic acid
(C) STRANDEDNESS: single
(D) TOPOLOGY: linear (ii) MOLECULE TYPE: DNA (vi) ORIGINAL SOURCE:
(C) INDIVIDUAL ISOLATE: jh1

(xi) SEQUENCE DESCRIPTION: SEQ ID NO: 40:

| | | |
|---|---|---|
| GTTAGTATGA GTGTCGTGCA GCCTCCAGGA CCCCCCCTCC | | 40 |
| CGGGAGAGCC ATAGTGGTCT GCGGAACCGG TGAGTACACC | | 80 |
| GGAATTGCCA GGACGACCGG GTCCTTTCTT GGATCAACCC | | 120 |
| GCTCAATGCC TGGAGATTTG GGCGTGCCCC CGCGAGACTG | | 160 |
| CTAGCCGAGT AGTGTTGGGT CGCGAAAGGC CTTGTGGTAC | | 200 |
| TGCCTGATAG GGTGCTTGCG AGTGCCCCGG GAGGTCTCGT | | 240 |
| AGACCGTGCA TC | | 252 |

(2) INFORMATION FOR SEQ ID NO:41:

(i) SEQUENCE CHARACTERISTICS:
(A) LENGTH: 252 nucleotides
(B) TYPE: nucleic acid
(C) STRANDEDNESS: single
(D) TOPOLOGY: linear (ii) MOLECULE TYPE: DNA (vi) ORIGINAL SOURCE:
(C) INDIVIDUAL ISOLATE: nac5

(xi) SEQUENCE DESCRIPTION: SEQ ID NO: 41:

| | | |
|---|---|---|
| GTTAGTATGA GTGTCGTGCA GCCTCCAGGA CCCCCCCTCC | | 40 |
| CGGGAGAGCC ATAGTGGTCT GCGGAACCGG TGAGTACACC | | 80 |
| GGAATTGCCA GGACGACCGG GTCCTTTCTT GGATCAACCC | | 120 |
| GCTCAATGCC TGGAGATTTG GGCGTGCCCC CGCGAGACTG | | 160 |

```
CTAGCCGAGT AGTGTTGGGT CGCGAAAGGC CTTGTGGTAC          200

TGCCTGATAG GGTGCTTGCG AGTGCCCCGG GAGGTCTCGT          240

AGACCGTGCA CC                                        252
```

(2) INFORMATION FOR SEQ ID NO:42:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: arg2

(xi) SEQUENCE DESCRIPTION: SEQ ID NO: 42:

```
GTTAGTATGA GTGTCGTGCA GCCTCCAGGA CCCCCCCTCC           40

CGGGAGAGCC ATAGTGGTCT GCGGAACCGG TGAGTACACC           80

GGAATTGCCA GGACGACCGG GTCCTTTCTT GGATCAACCC          120

GCTCAATGCC TGGAGATTTG GGCGTGCCCC CGCGAGACTG          160

CTAGCCGAGT AGTGTTGGGT CGCGAAAGGC CTTGTGGTAC          200

TGCCTGATAG GGTGCTTGCG AGTGCCCCGG GAGGTCTCGT          240

AGACCGTGCA CC                                        252
```

(2) INFORMATION FOR SEQ ID NO:43:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: sp1

(xi) SEQUENCE DESCRIPTION: SEQ ID NO: 43:

```
GTTAGTATGA GTGTCGTGCA GCCTCCAGGA CCCCCCCTCC           40

CGGGAGAGCC ATAGTGGTCT GCGGAACCGG TGAGTACACC           80

GGAATTGCCA GGACGACCGG GTCCTTTCTT GGATCAACCC          120

GCTCAATGCC TGGAGATTTG GGCGTGCCCC CGCGAGACTG          160

CTAGCCGAGT AGTGTTGGGT CGCGAAAGGC CTTGTGGTAC          200

TGCCTGATAG GGTGCTTGCG AGTGCCCCGG GAGGTCTCGT          240

AGACCGTGCA CC                                        252
```

(2) INFORMATION FOR SEQ ID NO:44:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:

(C) INDIVIDUAL ISOLATE: gh1

(xi) SEQUENCE DESCRIPTION: SEQ ID NO: 44:

| | |
|---|---|
| GTTAGTATGA GTGTCGTGCA GCCTCCAGGA CCCCCCCTCC | 40 |
| CGGGAGAGCC ATAGTGGTCT GCGGAACCGG TGAGTACACC | 80 |
| GGAATTGCCA GGACGACCGG GTCCTTTCTT GGATCAACCC | 120 |
| GCTCAATGCC TGGAGATTTG GGCGTGCCCC CGCGAGACTG | 160 |
| CTAGCCGAGT AGTGTTGGGT CGCGAAAGGC CTTGTGGTAC | 200 |
| TGCCTGATAG GGTGCTTGCG AGTGCCCCGG GAGGTCTCGT | 240 |
| AGACCGTGCA CC | 252 |

(2) INFORMATION FOR SEQ ID NO:45:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: i15

(xi) SEQUENCE DESCRIPTION: SEQ ID NO: 45:

| | |
|---|---|
| GTTAGTATGA GTGTCGTGCA GCCTCCAGGA CCCCCCCTCC | 40 |
| CGGGAGAGCC ATAGTGGTCT GCGGAACCGG TGAGTACACC | 80 |
| GGAATTGCCA GGACGACCGG GTCCTTTCTT GGATCAACCC | 120 |
| GCTCAATGCC TGGAGATTTG GGCGTGCCCC CGCGAGACTG | 160 |
| CTAGCCGAGT AGTGTTGGGT CGCGAAAGGC CTTGTGGTAC | 200 |
| TGCCTGATAG GGTGCTTGCG AGTGCCCCGG GAGGTCTCGT | 240 |
| AGACCGTGCA CC | 252 |

(2) INFORMATION FOR SEQ ID NO:46:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: i10

(xi) SEQUENCE DESCRIPTION: SEQ ID NO: 46:

| | |
|---|---|
| GCTAGTATCA GTGTCGTACA GCCTCCAGGC CCCCCCCTCC | 40 |
| CGGGAGAGCC ATAGTGGTCT GCGGAACCGG TGAGTACACC | 80 |
| GGAATTGCCG GGAAGACTGG GTCCTTTCTT GGATAAACCC | 120 |
| ACTCTATGCC CGGCCATTTG GGCGTGCCCC CGCAAGACTG | 160 |
| CTAGCCGAGT AGCGTTGGGT TGCGAAAGGC CTTGTGGTAC | 200 |
| TGCCTGATAG GGTGCTTGCG AGTGCCCCGG GAGGTCTCGT | 240 |
| AGACCGTGCA TC | 252 |

(2) INFORMATION FOR SEQ ID NO:47:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: arg6

(xi) SEQUENCE DESCRIPTION: SEQ ID NO: 47:

```
GTTAGTATGA GTCTCGTACA GCCTCCAGGC CCCCCCCTCC                 40

CGGGAGAGCC ATAGTGGTCT GCGGAACCGG TGAGTACACC                 80

GGAATTGCTG GGAAGACTGG GTCCTTTCTT GGATAAACCC                120

ACTCTATGCC CAGCCATTTG GGCGTGCCCC CGCAAGACTG                160

CTAGCCGAGT AGCGTTGGGT TGCGAAAGGC CTTGTGGTAC                200

TGCCTGATAG GGTGCTTGCG AGTGCCCCGG GAGGTCTCGT                240

AGACCGTGCA TC                                              252
```

(2) INFORMATION FOR SEQ ID NO:48:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: s21

(xi) SEQUENCE DESCRIPTION: SEQ ID NO: 48:

```
GTTAGTACGA GTGTCGTGCA GCCTCCAGGA CTCCCCCTCC                 40

CGGGAGAGCC ATAGTGGTCT GCGGAACCGG TGAGTACACC                 80

GGAATCGCTG GGGTGACCGG GTCCTTTCTT GGAGCAACCC                120

GCTCAATACC CAGAAATTTG GGCGTGCCCC CGCGAGATCA                160

CTAGCCGAGT AGTGTTGGGT CGCGAAAGGC CTTGTGGTAC                200

TGCCTGATAG GGTGCTTGCG AGTGCCCCGG GAGGTCTCGT                240

AGACCGTGCA AC                                              252
```

(2) INFORMATION FOR SEQ ID NO:49:

(i) SEQUENCE CHARACTERISTICS:
        (A) LENGTH: 252 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: gj61329

(xi) SEQUENCE DESCRIPTION: SEQ ID NO: 49:

```
GTTAGTACGA GTGTCGTGCA GCCTCCAGGA CCCCCCCTCC                 40

CGGGAGAGCC ATAGTGGTCT GCGGAACCGG TGAGTACACC                 80
```

-continued

```
GGAATCGCTG GGGTGACCGG GTCCTTTCTT GGAGTAACCC              120

GCTCAATACC CAGAAATTTG GGCGTGCCCC CGCGAGATCA              160

CTAGCCGAGT AGTGTTGGGT CGCGAAAGGC CTTGTGGTAC              200

TGCCTGATAG GGTGCTTGCG AGTGCCCCGG GAGGTCTCGT              240

AGACCGTGCA AC                                            252
```

(2) INFORMATION FOR SEQ ID NO:50:

(i) SEQUENCE CHARACTERISTICS:
        (A) LENGTH: 180 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: sa3

(xi) SEQUENCE DESCRIPTION: SEQ ID NO: 50:

```
GTTAGTATGA GTGTCGAACA GCCTCCAGGA CCCCCCCTCC              40

CGGGAGAGCC ATAGTGGTCT GCGGAACCGG TGAGTACACC              80

GGAATTGCCG GGATGACCGG GTCCTTTCTT GGATAAACCC              120

GCTCAATGCC CGGAGATTTG GGCGTGCCCC CGCGAGACTG              160

CTAGCCGAGT AGTGTTGGGT                                    180
```

(2) INFORMATION FOR SEQ ID NO:51:

(i) SEQUENCE CHARACTERISTICS:
        (A) LENGTH: 180 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: sa4

(xi) SEQUENCE DESCRIPTION: SEQ ID NO: 51:

```
GTTAGTATGA GTGTCGAACA GCCTCCAGGA CCCCCCCTCC              40

CGGGAGAGCC ATAGTGGTCT GCGGAACCGG TGAGTACACC              80

GGAATTGCCG GGATGACCGG GTCCTTTCTT GGATAAACCC              120

GCTCAATGCC CGGAGATTTG GGCGTGCCCC CGCGAGACTG              160

CTAGCCGAGT AGTGTTGGGT                                    180
```

(2) INFORMATION FOR SEQ ID NO:52:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE: (ATCC # 40394)
        (C) INDIVIDUAL ISOLATE: hcv1

(xi) SEQUENCE DESCRIPTION: SEQ ID NO: 52:

```
ATGAGCACGA ATCCTAAACC TCAAAAAAAA AACAAACGTA              40
```

```
ACACCAACCG TCGCCCACAG GACGTCAAGT TCCCGGGTGG                    80

CGGTCAGATC GTTGGTGGAG TTTACTTGTT GCCGCGCAGG                   120

GGCCCTAGAT TGGGTGTGCG CGCGACGAGA AAGACTTCCG                   160

AGCGGTCGCA ACCTCGAGGT AGACGTCAGC CTATCCCCAA                   200

GGCTCGTCGG CCCGAGGGCA GGACCTGGGC TCAGCCCGGG                   240

TACCCTTGGC CCCTCTATGG CAATGAGGGC TGCGGGTGGG                   280

CGGGATGGCT CCTGTCTCCC CGTGGCTCTC GGCCTAGCTG                   320

GGGCCCCACA GACCCCCGGC GTAGGTCGCG CAATTTGGGT                   360

AAGGTCATCG ATACCCTTAC GTGCGGCTTC GCCGACCTCA                   400

TGGGGTACAT ACCGCTCGTC GGCGCCCCTC TTGGAGGCGC                   440

TGCCAGGGCC CTGGCGCATG GCGTCCGGGT TCTGGAAGAC                   480

GGCGTGAACT ATGCAACAGG GAACCTTCCT GGTTGCTCTT                   520

TCTCTATCTT CCTTCTGGCC CTGCTCTCT                               549

(2) INFORMATION FOR SEQ ID NO:53:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
         (C) INDIVIDUAL ISOLATE: us5

(xi) SEQUENCE DESCRIPTION: SEQ ID NO: 53:

ATGAGCACGA ATCCTAAACC TCAAAGAAAA ACCAAACGTA                    40

ACACCAACCG TCGCCCACAG GACGTCAAGT TCCCGGGTGG                    80

CGGTCAGATC GTTGGTGGAG TTTACTTGTT GCCGCGCAGG                   120

GGCCCTAGAT TGGGTGTGCG CGCGACGAGG AAGACTTCCG                   160

AGCGGTCGCA ACCTCGAGGT AGACGTCAGC CTATCCCCAA                   200

GGCGCGTCGG CCCGAGGGCA GGACCTGGGC TCAGCCCGGG                   240

TACCCTTGGC CCCTCTATGG CAATGAGGGT TGCGGGTGGG                   280

CGGGATGGCT CCTGTCTCCC CGTGGCTCTC GGCCTAGTTG                   320

GGGCCCCACA GACCCCCGGC GTAGGTCGCG CAATTTGGGT                   360

AAGGTCATCG ATACCCTTAC GTGCGGCTTC GCCGACCACA                   400

TGGGGTACAT ACCGCTCGTC GGCGCCCCTC TTGGAGGCGC                   440

TGCCAGGGCT CTGGCGCATG GCGTCCGGGT TCTGGAAGAC                   480

GGCGTGAACT ATGCAACAGG GAACCTTCCT GGTTGCTCTT                   520

TCTCTATCTT CCTTCTGGCC CTGCTCTCT                               549

(2) INFORMATION FOR SEQ ID NO:54:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear
```

(ii) MOLECULE TYPE: DNA (vi) ORIGINAL SOURCE:
                 (C) INDIVIDUAL ISOLATE: aus1

(xi) SEQUENCE DESCRIPTION: SEQ ID NO: 54:

| | |
|---|---|
| ATGAGCACGA ATCCTAAACC TCAAAGAAAA ACCAAACGTA | 40 |
| ACACCAACCG TCGCCCACAG GACGTTAAGT TCCCGGGTGG | 80 |
| CGGTCAGATC GTTGGTGGAG TTTACTTGTT GCCGCGCAGG | 120 |
| GGCCCTAGAT TGGGTGTGCG CGCGACGAGG AAGACTTCCG | 160 |
| AGCGGTCGCA ACCTCGAGGT AGACGTCAGC CTATCCCTAA | 200 |
| GGCGCGTCGG CCCGAGGGCA GGACCTGGGC TCAGCCCGGG | 240 |
| TACCCCTGGC CCCTCTATGG TAATGAGGGT TGCGGATGGG | 280 |
| CGGGATGGCT CCTGTCCCCC CGTGGCTCTC GGCCTAGTTG | 320 |
| GGGCCCTACA GACCCCCGGC GTAGGTCGCG CAATTTGGGT | 360 |
| AAGGTCATCG ATACCCTCAC GTGCGGCTTC GCCGACCACA | 400 |
| TGGGGTACAT TCCGCTCGTT GGCGCCCCTC TTGGGGCGC  | 440 |
| TGCCAGGGCC CTGGCGCATG GCGTCCGGGT TCTGGAAGAC | 480 |
| GGCGTGAACT ATGCAACAGG GAATCTTCCT GGTTGCTCTT | 520 |
| TCTCTATCTT CCTTCTGGCC CTTCTCTCT             | 549 |

(2) INFORMATION FOR SEQ ID NO:55:

(i) SEQUENCE CHARACTERISTICS:
            (A) LENGTH: 549 nucleotides
            (B) TYPE: nucleic acid
            (C) STRANDEDNESS: single
            (D) TOPOLOGY: linear (ii) MOLECULE TYPE: DNA (vi) ORIGINAL SOURCE:
             (C) INDIVIDUAL ISOLATE: sp2

(xi) SEQUENCE DESCRIPTION: SEQ ID NO: 55:

| | |
|---|---|
| ATGAGCACGA ATCCTAAACC TCAAAGAAAA ACCAAACGTA | 40 |
| ACACCAACCG TCGCCCACAG GACGTCAAGT TCCCGGGTGG | 80 |
| CGGTCAGATC GTTGGTGGAG TTTACTTGTT GCCGCGCAGG | 120 |
| GGCCCTAGAT TGGGTGTGCG CACGACGAGG AAGACTTCCG | 160 |
| AGCGGTCGCA ACCTCGAGGT AGACGTCAGC CCATCCCCAA | 200 |
| GGCTCGTCGA CCCGAGGGCA GGACCTGGGC TCAGCCCGGG | 240 |
| TACCCTTGGC CCCTCTATGG CAATGAGGGC TGCGGGTGGG | 280 |
| CGGGATGGCT CCTGTCTCCC CGTGGCTCTC GGCCTAGCTG | 320 |
| GGGCCCCACA GACCCCCGGC GTAGGTCGCG CAATTTGGGT | 360 |
| AAGGTCATCG ATACCCTTAC GTGCGGCTTC GCCGACCTCA | 400 |
| TGGGGTACAT ACCGCTCGTC GGCGCCCCTC TTGGAGGCGC | 440 |
| TGCCAGAGCC CTGGCGCATG GCGTCCGGGT TCTGGAAGAC | 480 |
| GGCGTGAACT ATGCAACAGG GAACCTTCCC GGTTGCTCTT | 520 |
| TCTCTATCTT CCTTCTGGCC CTGCTCTCT             | 549 |

(2) INFORMATION FOR SEQ ID NO:56:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: gm2

(xi) SEQUENCE DESCRIPTION: SEQ ID NO: 56:

| | |
|---|---|
| ATGAGCACGA ATCCTAAACC TCAAAGAAGA ACCAAACGTA | 40 |
| ACACCAACCG TCGCCCACAG GACGTCAAGT TCCCGGGTGG | 80 |
| CGGTCAGATC GTTGGTGGAG TTTACTTGTT GCCGCGCAGG | 120 |
| GGCCCTAGAT TGGGTGTGCG CGCGACGAGG AAGACTTCCG | 160 |
| AGCGGTCGCA ACCTCGAGGT AGACGTCAGC CTATCCCCAA | 200 |
| GGCACGTCGG CCCGAGGGTA GGACCTGGGC TCAGCCCGGG | 240 |
| TACCCTTGGC CCCTCTATGG CAATGAGGGT TGCGGGTGGG | 280 |
| CGGGATGGCT CCTGTCTCCC CGCGGCTCTC GGCCTAACTG | 320 |
| GGGCCCCACA GACCCCCGGC GTAGGTCGCG CAATTTGGGT | 360 |
| AAGGTCATCG ATACCCTTAC GTGCGGCTTC GCCGACCTCA | 400 |
| TGGGGTACAT ACCGCTCGTC GGCGCCCCTC TTGGAGGCGC | 440 |
| TGCCAGGGCC CTGGCGCATG GCGTCCGGGT TCTGGAAGAC | 480 |
| GGCGTGAACT ATGCAACAGG GAACCTTCCT GGTTGCTCTT | 520 |
| TCTCTATCTT CCTTCTGGCC CTGCTCTCT | 549 |

(2) INFORMATION FOR SEQ ID NO:57:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: i21

(xi) SEQUENCE DESCRIPTION: SEQ ID NO: 57:

| | |
|---|---|
| ATGAGCACGA ATCCTAAACC TCAAAGAAAA ACCAAACGTA | 40 |
| ACACCAACCG TCGCCCACAG GACGTCAAGT TCCCGGGTGG | 80 |
| CGGTCAGATC GTTGGTGGAG TTTACTTGTT GCCGCGCAGG | 120 |
| GGCCCTAGAT TGGGTGTGCG CGCGACGAGG AAGACTTCCG | 160 |
| AGCGGTCGCA ACCTCGTGGT AGACGCCAGC CTATCCCCAA | 200 |
| GGCGCGTCGG CCCGAGGGCA GGACCTGGGC TCAGCCCGGG | 240 |
| TACCCTTGGC CCCTCTATGG CAATGAGGGT TGCGGGTGGG | 280 |
| CGGGATGGCT CCTGTCTCCC CGTGGCTCTC GGCCTAGCTG | 320 |
| GGGCCCCACA GACCCCCGGC GTAGGTCGCG CAATTTGGGT | 360 |

| | |
|---|---|
| AAGGTCATCG ATACCCTTAC GTGCGGCTTC GCCGACCTCA | 400 |
| TGGGGTACAT ACCGCTCGTC GGCGCCCCTC TTGGAGGCGC | 440 |
| TGCCAGGGCC CTGGCGCATG GCGTCCGGGT TCTGGAAGAC | 480 |
| GGCGTGAACT ATGCAACAGG GAACCTTCCT GGTTGCTCTT | 520 |
| TTTCTATTTT CCTTCTGGCC CTGCTCTCT | 549 |

(2) INFORMATION FOR SEQ ID NO:58:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: us4

(xi) SEQUENCE DESCRIPTION: SEQ ID NO: 58:

| | |
|---|---|
| ATGAGCACGA ATCCTAAACC TCAAAGAAAA ACCAAACGTA | 40 |
| ACACCAACCG CCGCCCACAG GACGTTAAGT TCCCGGGCGG | 80 |
| TGGCCAGGTC GTTGGTGGAG TTTACCTGTT GCCGCGCAGG | 120 |
| GGCCCCAGGT TGGGTGTGCG CGCGACTAGG AAGACTTCCG | 160 |
| AGCGGTCGCA ACCTCGTGGA AGGCGACAAC CTATCCCCAA | 200 |
| GGCTCGCCAG CCCGAGGGCA GGGCCTGGGC TCAGCCCGGG | 240 |
| TACCCTTGGC CCCTCTATGG CAATGAGGGT ATGGGGTGGG | 280 |
| CAGGATGGCT CCTGTCACCC CGTGGCTCTC GGCCTAGTTG | 320 |
| GGGCCCCACG GACCCCCGGC GTAGGTCGCG TAATTTGGGT | 360 |
| AAGGTCATCG ATACCCTCAC ATGCGGCTTC GCCGACCTCA | 400 |
| TGGGGTACAT TCCGCTCGTC GGCGCCCCCC TTAGGGGCGC | 440 |
| TGCCAGGGCC TTGGCGCATG GCGTCCGGGT TCTGGAGGAC | 480 |
| GGCGTGAACT ACGCAACAGG GAATCTGCCC GGTTGCTCCT | 520 |
| TTTCTATCTT CCTCTTGGCT CTGCTGTCC | 549 |

(2) INFORMATION FOR SEQ ID NO:59:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: jh1

(xi) SEQUENCE DESCRIPTION: SEQ ID NO: 59:

| | |
|---|---|
| ATGAGCACAA ATCCTAAACC TCAAAGAAAA ACCAAACGTA | 40 |
| ACACCAACCG CCGCCCACAG GACGTCAAGT TCCCGGGCGG | 80 |
| TGGTCAGATC GTTGGTGGAG TTTACCTGTT GCCGCGCAGG | 120 |
| GGCCCCAGGT TGGGTGTGCG CGCGACTAGG AAGACTTCCG | 160 |
| AGCGGTCGCA ACCTCGTGGA AGGCGACAAC CTATCCCCAA | 200 |

```
GGCTCGCCAG CCCGAGGGCA GGGCCTGGGC TCAGCCCGGG                      240

TACCCTTGGC CCCTCTATGG CAACGAGGGT ATGGGGTGGG                      280

CAGGATGGCT CCTGTCACCC CGTGGCTCTC GGCCTAGTTG                      320

GGGCCCCACG GACCCCCGGC GTAGGTCGCG TAATTTGGGT                      360

AAGGTCATCG ATACCCTCAC ATGCGGCTTC GCCGACCTCA                      400

TGGGGTACAT TCCGCTTGTC GGCGCCCCCC TAGGGGCGC                       440

TGCCAGGGCC CTGGCACATG GTGTCCGGGT TCTGGAGGAC                      480

GGCGTGAACT ATGCAACAGG GAATTTGCCC GGTTGCTCTT                      520

TCTCTATCTT CCTCTTGGCT CTGCTGTCC                                  549
```

(2) INFORMATION FOR SEQ ID NO:60:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: nac5

(xi) SEQUENCE DESCRIPTION: SEQ ID NO: 60:

```
ATGAGCACAA ATCCTAAACC CAAAGAAAA ACCAAACGTA                       40

ACACCAACCG TCGCCCACAG GACGTCAAGT TCCCGGGCGG                      80

TGGTCAGATC GTTGGTGGAG TTTACCTGTT GCCGCGCAGG                      120

GGCCCCAGGT TGGGTGTGCG CGCGACTAGG AAGACTTCCG                      160

AGCGGTCGCA ACCTCGTGGA AGGCGACAAC CTATCCCCAA                      200

GGCTCGCCGG CCCGAGGGCA GGTCCTGGGC TCAGCCCGGG                      240

TACCCTTGGC CCCTCTATGG CAACGAGGGT ATGGGGTGGG                      280

CAGGATGGCT CCTGTCACCC CGCGGCTCCC GGCCTAGTTG                      320

GGGCCCCACG GACCCCCGGC GTAGGTCGCG TAATTTGGGT                      360

AAGGTCATCG ATACCCTCAC ATGCGGCTTC GCCGACCTCA                      400

TGGGGTACAT TCCGCTCGTC GGCGCCCCCC TAGGGGCGC                       440

TGCCAGGGCC CTGGCACATG GTGTCCGGGT TCTGGAGGAC                      480

GGCGTGAACT ATGCAACAGG GAATTTGCCT GGTTGCTCTT                      520

TCTCTATCTT CCTCTTGGCT CTGCTGTCC                                  549
```

(2) INFORMATION FOR SEQ ID NO:61:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: arg2

(xi) SEQUENCE DESCRIPTION: SEQ ID NO: 61:

-continued

| | |
|---|---|
| ATGAGCACGA ATCCTAAACC TCAAAGAAAA ACCAAACGTA | 40 |
| ACACCAACCG CCGCCCACAG GACGTCAAGT TCCCGGGCGG | 80 |
| TGGTCAGATC GTTGGTGGAG TTTACTTGTT GCCGCGCAGG | 120 |
| GGCCCCAGGT TGGGTGTGCG CGCGACTAGG AAGACTTCCG | 160 |
| AGCGGTCGCA ACCTCGTGGA AGGCGACAAC CTATCCCCAA | 200 |
| GGCTCGCCAG CCCGAGGGTA GGGCCTGGGC TCAGCCCGGG | 240 |
| TACCCTTGGC CCCTCTATGG CAATGAGGGT ATGGGGTGGG | 280 |
| CAGGGTGGCT CCTGTCCCCC CGCGGCTCCC GGCCTAGTTG | 320 |
| GGGCCCCACA GACCCCCGGC GTAGGTCGCG TAATTTGGGT | 360 |
| AAGGTCATCG ATACCCTCAC ATGCGGCTTC GCCGACCTCA | 400 |
| TGGGGTACAT TCCGCTCGTC GGCGCCCCCC TAGGGGCGC | 440 |
| TGCCAGGGCC CTGGCGCATG GCGTCCGGGT TCTGGAGGAC | 480 |
| GGCGTGAACT ATGCAACAGG GAATCTGCCC GGTTGCTCTT | 520 |
| TCTCTATCTT CCTCTTGGCT TTGCTGTCC | 549 |

(2) INFORMATION FOR SEQ ID NO:62:

(i) SEQUENCE CHARACTERISTICS:
        (A) LENGTH: 549 nucleotides
        (B) TYPE: nucleic acid
        (C) STRANDEDNESS: single
        (D) TOPOLOGY: linear (ii) MOLECULE TYPE: DNA (vi) ORIGINAL SOURCE:
        (C) INDIVIDUAL ISOLATE: sp1

(xi) SEQUENCE DESCRIPTION: SEQ ID NO: 62:

| | |
|---|---|
| ATGAGCACGA ATCCTAAACC TCAAAGAAAA ACCAAACGTA | 40 |
| ACACCAACCG CCGCCCACAG GACGTCAAGT TCCCGGGCGG | 80 |
| TGGTCAGATC GTTGGTGGAG TTTACCTGTT GCCGCGCAGG | 120 |
| GGCCCCAGGT TGGGTGTGCG CGCGACTAGG AAGACTTCCG | 160 |
| AGCGGTCGCA ACCTCGTGGA AGGCGACAAC CTATCCCCAA | 200 |
| GGCTCGCCGG CCCGAGGGCA GGGCCTGGGC TCAGCCCGGG | 240 |
| TATCCTTGGC CCCTCTATGG CAATGAGGGT CTGGGGTGGG | 280 |
| CAGGATGGCT CCTGTCACCC CGCGGCTCTC GGCCTAGCTG | 320 |
| GGGCCCTACC GACCCCCGGC GTAGGTCGCG CAACTTGGGT | 360 |
| AAGGTCATCG ATACCCTTAC GTGCGGCTTC GCCGACCTCA | 400 |
| TGGGGTACAT TCCGCTCGTC GGCGCCCCCC TTAGGGCGC | 440 |
| TGCCAGGGCC CTGGCGCATG GCGTCCGGGT TCTGGAGGAC | 480 |
| GGCGTGAACT ATGCAACAGG GAATTTGCCC GGTTGCTCTT | 520 |
| TCTCTATCTT CCTCTTGGCT TTGCTGTCC | 549 |

(2) INFORMATION FOR SEQ ID NO:63:

(i) SEQUENCE CHARACTERISTICS:
        (A) LENGTH: 549 nucleotides
        (B) TYPE: nucleic acid
        (C) STRANDEDNESS: single

```
            (D) TOPOLOGY: linear (ii) MOLECULE TYPE:  DNA (vi) ORIGINAL SOURCE:
            (C) INDIVIDUAL ISOLATE:  gh1

(xi) SEQUENCE DESCRIPTION: SEQ ID NO: 63:

ATGAGCACGA ATCCTAAACC TCAAAGAAAA ACCAAACGTA              40

ACACCAACCG CCGCCCACAG GACGTCAAGT TCCCGGGCGG              80

TGGTCAGATC GTTGGTGGAG TTTACTTGTT GCCGCGCAGG             120

GGCCCCAGGT TGGGTGTGCG CGCGACTAGG AAGACTTCCG             160

AGCGGTCGCA ACCTCGTGGA AGGCGACAAC CTATCCCCAA             200

GGCTCGCCGG CCCGAGGGCA GGGCCTGGGC TCAGCCCGGG             240

TACCCTTGGC CCCTCTATGG CAATGAGGGT ATGGGGTGGG             280

CAGGATGGCT CCTGTCACCC CGTGGTTCTC GGCCTAGTTG             320

GGGCCCCACG GACCCCCGGC GTAGGTCGCG CAATTTGGGT             360

AAGATCATCG ATACCCTCAC GTGCGGCTTC GCCGACCTCA             400

TGGGGTACAT TCCGCTCGTC GGCGCCCCCC TAGGGGCGC              440

TGCCAGGGCC CTGGCGCATG GCGTCCGGGT TCTGGAGGAC             480

GGCGTGAACT ATGCAACAGG GAATCTGCCC GGTTGCTCCT             520

TTTCTATCTT CCTTCTGGCT TTGCTGTCC                         549

(2) INFORMATION FOR SEQ ID NO:64:

(i) SEQUENCE CHARACTERISTICS:
            (A) LENGTH: 549 nucleotides
            (B) TYPE: nucleic acid
            (C) STRANDEDNESS:  single
            (D) TOPOLOGY: linear (ii) MOLECULE TYPE:  DNA (vi) ORIGINAL SOURCE:
            (C) INDIVIDUAL ISOLATE:  i15

(xi) SEQUENCE DESCRIPTION: SEQ ID NO: 64:

ATGAGCACGA ATCCTAAACC TCAAAGAAAA ACCAAACGTA              40

ACACCAACCG CCGCCCACAG GACGTCAAGT TCCCGGGCGG              80

TGGTCAGATC GTTGGTGGAG TTTACCTGTT GCCGCGCAGG             120

GGCCCCAGGT TGGGTGTGCG CGCGACTAGG AAGACTTCCG             160

AGCGGTCGCA ACCTCGTGGA AGGCGACAAC CTATCCCCAA             200

GGCTCGCCAG CCCGAGGGCA GGGCCTGGGC TCAGCCCGGG             240

TACCCCTGGC CCCTCTATGG CAATGAGGGT ATGGGGTGGG             280

CAGGATGGCT CCTGTCACCC CGCGGCTCCC GGCCTAGTTG             320

GGGCCCCAAA GACCCCCGGC GTAGGTCGCG TAATTTGGGT             360

AAGGTCATCG ATACCCTCAC ATGCGGCTTC GCCGACCTCA             400

TGGGGTACAT TCCGCTCGTC GGCGCCCCCT TAGGGGCGC              440

TGCCAGGGCC CTGGCGCATG GCGTCCGGGT TCTGGAGGAC             480

GGCGTGAACT ATGCAACAGG GAATCTACCC GGTTGCTCTT             520
```

```
TCTCTATCTT CCTCTTGGCT TTGCTGTCC                                              549

(2) INFORMATION FOR SEQ ID NO:65:

(i) SEQUENCE CHARACTERISTICS:
        (A) LENGTH: 549 nucleotides
        (B) TYPE: nucleic acid
        (C) STRANDEDNESS:  single
        (D) TOPOLOGY: linear (ii) MOLECULE TYPE:  DNA (vi) ORIGINAL SOURCE:
        (C) INDIVIDUAL ISOLATE:  i10

(xi) SEQUENCE DESCRIPTION: SEQ ID NO: 65:

ATGAGCACAA ATCCTAAACC TCAAAGAAAA ACCAAAAGAA                                    40

ACACTAACCG CCGCCCACAG GACGTCAAGT TCCCGGGCGG                                    80

TGGCCAGATC GTTGGCGGAG TATACTTGCT GCCGCGCAGG                                   120

GGCCCGAGAT TGGGTGTGCG CGCGACGAGG AAAACTTCCG                                   160

AACGATCCCA GCCACGCGGA AGGCGTCAGC CCATCCCTAA                                   200

AGATCGTCGC ACCGCTGGCA AGTCCTGGGG AAGGCCAGGA                                   240

TATCCTTGGC CCCTGTATGG GAATGAGGGT CTCGGCTGGG                                   280

CAGGGTGGCT CCTGTCCCCC CGTGGCTCTC GCCCTTCATG                                   320

GGGCCCCACT GACCCCCGGC ATAGATCGCG CAACTTGGGT                                   360

AAGGTCATCG ATACCCTAAC GTGCGGTTTT GCCGACCTCA                                   400

TGGGGTACAT TCCCGTCATC GGCGCCCCCG TTGGAGGCGT                                   440

TGCCAGAGCT CTCGCCCACG GAGTGAGGGT TCTGGAGGAT                                   480

GGGGTAAATT ATGCAACAGG GAATTTGCCC GGTTGCTCTT                                   520

TCTCTATCTT TCTCTTAGCC CTCTTGTCT                                              549

(2) INFORMATION FOR SEQ ID NO:66:

(i) SEQUENCE CHARACTERISTICS:
        (A) LENGTH: 510 nucleotides
        (B) TYPE: nucleic acid
        (C) STRANDEDNESS:  single
        (D) TOPOLOGY: linear (ii) MOLECULE TYPE:  DNA (vi) ORIGINAL SOURCE:
        (C) INDIVIDUAL ISOLATE:  arg6

(xi) SEQUENCE DESCRIPTION: SEQ ID NO: 66:

ATGAGCACAA ATCCTCAACC TCAAAGAAAA ACCAAAAGAA                                    40

ACACTAACCG CCGCCCACAG GACGTCAAGT TCCCGGGCGG                                    80

TGGTCAGATC GTTGGCGGAG TATACTTGTT GCCGCGCAGG                                   120

GGCCCCAGGT TGGGTGTGCG CGCGACGAGG AAAACTTCCG                                   160

AACGGTCCCA GCCACGTGGG AGGCGCCAGC CCATCCCCAA                                   200

AGATCGGCGC ACCACTGGCA AGTCCTGGGG GAAGCCAGGA                                   240

TACCCTTGGC CCCTGTATGG GAATGAGGGT CTCGGCTGGG                                   280

CAGGGTGGCT CCTGTCCCCC CGCGGTTCTC GCCCTTCATG                                   320

GGGCCCCACT GACCCCCGGC ATAGATCACG CAACTTGGGT                                   360
```

```
AAGGTCATCG ATACCCTAAC GTGTGGTTTT GCCGACCTCA                              400

TGGGGTACAT TCCCGTCGGT GGTGCCCCCG TTGGTGGTGT                              440

CGCCAGAGCC CTTGCCCATG GGGTGAGGGT TCTGGAAGAC                              480

GGGATAAATT ATGCAACAGG GAATCTGCCC                                         510

(2) INFORMATION FOR SEQ ID NO:67:

(i) SEQUENCE CHARACTERISTICS:
        (A) LENGTH: 29 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 67:

CAAACGTAAC ACCAACCGRC GCCCACAGG                                          29

(2) INFORMATION FOR SEQ ID NO:68:

(i) SEQUENCE CHARACTERISTICS:
        (A) LENGTH: 24 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 68:

ACAGAYCCGC AKAGRTCCCC CACG                                               24

(2) INFORMATION FOR SEQ ID NO:69:

(i) SEQUENCE CHARACTERISTICS:
        (A) LENGTH: 30 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 69:

CGAACCTCGA GGTAGACGTC AGCCTATCCC                                         30

(2) INFORMATION FOR SEQ ID NO:70:

(i) SEQUENCE CHARACTERISTICS:
        (A) LENGTH: 30 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 70:

GCAACCTCGT GGAAGGCGAC AACCTATCCC                                         30

(2) INFORMATION FOR SEQ ID NO:71:

(i) SEQUENCE CHARACTERISTICS:
        (A) LENGTH: 30 nucleotides
        (B) TYPE: nucleic acid
        (C) STRANDEDNESS:  single
        (D) TOPOLOGY: linear (ii) MOLECULE TYPE:  DNA
```

(xi) SEQUENCE DESCRIPTION: SEQ ID NO: 71:

GTCACCAATG ATTGCCCTAA CTCGAGTATT                                    30

(2) INFORMATION FOR SEQ ID NO:72:

(i) SEQUENCE CHARACTERISTICS:
        (A) LENGTH: 26 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 72:

GTCACGAACG ACTGCTCCAA CTCAAG                                        26

(2) INFORMATION FOR SEQ ID NO:73:

(i) SEQUENCE CHARACTERISTICS:
        (A) LENGTH: 28 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 73:

TGGACATGAT CGCTGGWGCY CACTGGGG                                      28

(2) INFORMATION FOR SEQ ID NO:74:

(i) SEQUENCE CHARACTERISTICS:
        (A) LENGTH: 28 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 74:

TGGAYATGGT GGYGGGGGCY CACTGGGG                                      28

(2) INFORMATION FOR SEQ ID NO:75:

(i) SEQUENCE CHARACTERISTICS:
        (A) LENGTH: 20 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 75:

ATGATGAACT GGTCVCCYAC                                               20

(2) INFORMATION FOR SEQ ID NO:76:

(i) SEQUENCE CHARACTERISTICS:
        (A) LENGTH: 26 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 76:

ACCTTVGCCC AGTTSCCCRC CATGGA                                        26

(2) INFORMATION FOR SEQ ID NO:77:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 77:

AACCCACTCT ATGYCCGGYC AT                                          22

(2) INFORMATION FOR SEQ ID NO:78:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 78:

GAATCGCTGG GGTGACCG                                              18

(2) INFORMATION FOR SEQ ID NO:79:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 79:

CCATGAATCA CTCCCCTGTG AGGAACTA                              28

(2) INFORMATION FOR SEQ ID NO:80:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 80:

TTGCGGGGGC ACGCCCAA                                              18

(2) INFORMATION FOR SEQ ID NO:81:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 81:

YGAAGCGGGC ACAGTCARRC AAGARAGCAG GGC                        33

(2) INFORMATION FOR SEQ ID NO:82:

(i) SEQUENCE CHARACTERISTICS:
    (A) LENGTH: 33 nucleotides
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 82:

RTARAGCCCY GWGGAGTTGC GCACTTGGTR GGC                                    33

(2) INFORMATION FOR SEQ ID NO:83:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 83:

RATACTCGAG TTAGGGCAAT CATTGGTGAC RTG                                    33

(2) INFORMATION FOR SEQ ID NO:84:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 84:

AGYRTGCAGG ATGGYATCRK BCGYCTCGTA CAC                                    33

(2) INFORMATION FOR SEQ ID NO:85:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 85:

GTTRCCCTCR CGAACGCAAG GGACRCACCC CGG                                    33

(2) INFORMATION FOR SEQ ID NO:86:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 86:

CGTRGGGGTY AYCGCCACCC AACACCTCGA GRC                                    33

(2) INFORMATION FOR SEQ ID NO:87:

(i) SEQUENCE CHARACTERISTICS:
        (A) LENGTH: 33 nucleotides
        (B) TYPE: nucleic acid
        (C) STRANDEDNESS: single (D) TOPOLOGY: linear (ii) MOLECULE TYPE:  DNA (xi) SEQUENCE DESCRIPTION: SEQ ID NO: 87:

CGTYGYGGGG AGTTTGCCRT CCCTGGTGGC YAC                33

(2) INFORMATION FOR SEQ ID NO:88:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 88:

CCCGACAAGC AGATCGATGT GACGTCGAAG CTG                33

(2) INFORMATION FOR SEQ ID NO:89:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 89:

CCCCACGTAG ARGGCCGARC AGAGRGTGGC GCY                33

(2) INFORMATION FOR SEQ ID NO:90:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 90:

YTGRCCGACA AGAAAGACAG ACCCGCAYAR GTC                33

(2) INFORMATION FOR SEQ ID NO:91:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 91:

CGTCCAGTGG YGCCTGGGAG AGAAGGTGAA CAG                33

(2) INFORMATION FOR SEQ ID NO:92:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 92:

GCCGGGATAG ATRGARCAAT TGCARYCTTG CGT                                33

(2) INFORMATION FOR SEQ ID NO:93:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 93:

CATATCCCAT GCCATGCGGT GACCCGTTAY ATG                                33

(2) INFORMATION FOR SEQ ID NO:94:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 94:

YACCAAYGCC GTCGTAGGGG ACCARTTCAT CAT                                33

(2) INFORMATION FOR SEQ ID NO:95:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 95:

GATGGCTTGT GGGATCCGGA GYASCTGAGC YAY                                33

(2) INFORMATION FOR SEQ ID NO:96:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 96:

GACTCCCCAG TGRGCWCCAG CGATCATRTC CAW                                33

(2) INFORMATION FOR SEQ ID NO:97:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 97:

CCCCACCATG GAGAAATACG CTATGCCCGC YAG                                33

(2) INFORMATION FOR SEQ ID NO:98:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 98:

TAGYAGCAGY ACTACYARGA CCTTCGCCCA GTT                33

(2) INFORMATION FOR SEQ ID NO:99:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 99:

GSTGACGTGR GTKTCYGCGT CRACGCCGGC RAA                33

(2) INFORMATION FOR SEQ ID NO:100:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 100:

GGAAGYTGGG ATGGTYARRC ARGASAGCAR AGC                33

(2) INFORMATION FOR SEQ ID NO:101:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 101:

GTAYAYYCCG GACRCGTTGC GCACTTCRTA AGC                33

(2) INFORMATION FOR SEQ ID NO:102:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 102:

AATRCTTGMG TTGGAGCART CGTTYGTGAC ATG                33

(2) INFORMATION FOR SEQ ID NO:103:

(i) SEQUENCE CHARACTERISTICS:

(A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 103:

RGYRTGCATG ATCAYGTCCG YYGCCTCATA CAC                33

(2) INFORMATION FOR SEQ ID NO:104:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 104:

RTTGTYYTCC CGRACGCARG GCACGCACCC RGG                33

(2) INFORMATION FOR SEQ ID NO:105:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 105:

CGTGGGRGTS AGCGCYACCC AGCARCGGGA GSW                33

(2) INFORMATION FOR SEQ ID NO:106:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 106:

YGTRGTGGGG AYGCTGKHRT TCCTGGCCGC VAR                33

(2) INFORMATION FOR SEQ ID NO:107:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 107:

CCCRACGAGC AARTCGACRT GRCGTCGTAW TGT                33

(2) INFORMATION FOR SEQ ID NO:108:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 108:

YCCCACGTAC ATAGCSGAMS AGARRGYAGC CGY                              33

(2) INFORMATION FOR SEQ ID NO:109:

(i) SEQUENCE CHARACTERISTICS:
            (A) LENGTH: 33 nucleotides
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 109:

CTGGGAGAYR AGRAAAACAG ATCCGCARAG RTC                              33

(2) INFORMATION FOR SEQ ID NO:110:

(i) SEQUENCE CHARACTERISTICS:
            (A) LENGTH: 33 nucleotides
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 110:

YGTCTCRTGC CGGCCAGSBG AGAAGGTGAA YAG                              33

(2) INFORMATION FOR SEQ ID NO:111:

(i) SEQUENCE CHARACTERISTICS:
            (A) LENGTH: 33 nucleotides
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 111:

GCCGGGATAG AKKGAGCART TGCAKTCCTG YAC                              33

(2) INFORMATION FOR SEQ ID NO:112:

(i) SEQUENCE CHARACTERISTICS:
            (A) LENGTH: 33 nucleotides
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 112:

CATATCCCAA GCCATRCGRT GGCCTGAYAC CTG                              33

(2) INFORMATION FOR SEQ ID NO:113:

(i) SEQUENCE CHARACTERISTICS:
            (A) LENGTH: 33 nucleotides
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 113:

CACTARGGCT GYYGTRGGYG ACCAGTTCAT CAT                                              33

(2) INFORMATION FOR SEQ ID NO:114:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 114:

GACRGCTTGT GGGATCCGGA GTAACTGCGA YAC                                              33

(2) INFORMATION FOR SEQ ID NO:115:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 115:

GACTCCCCAG TGRGCCCCCG CCACCATRTC CAT                                              33

(2) INFORMATION FOR SEQ ID NO:116:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 116:

SCCCACCATG GAWWAGTAGG CAAGGCCCGC YAG                                              33

(2) INFORMATION FOR SEQ ID NO:117:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 117:

GAGTAGCATC ACAATCAADA CCTTAGCCCA GTT                                              33

(2) INFORMATION FOR SEQ ID NO:118:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 118:

YGWCRYGYRG GTRTKCCCGT CAACGCCGGC AAA                                              33

(2) INFORMATION FOR SEQ ID NO:119:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 119:

TCCTCACAGG GGAGTGATTC ATGGTGGAGT GTC                    33

(2) INFORMATION FOR SEQ ID NO:120:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 120:

ATGGCTAGAC GCTTTCTGCG TGAAGACAGT AGT                    33

(2) INFORMATION FOR SEQ ID NO:121:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 121:

GCCTGGAGGC TGCACGRCAC TCATACTAAC GCC                    33

(2) INFORMATION FOR SEQ ID NO:122:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 122:

CGCAGACCAC TATGGCTCTY CCGGGAGGGG GGG                    33

(2) INFORMATION FOR SEQ ID NO:123:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 123:

TCRTCCYGGC AATTCCGGTG TACTCACCGG TTC                    33

(2) INFORMATION FOR SEQ ID NO:124:

(i) SEQUENCE CHARACTERISTICS:
        (A) LENGTH: 33 nucleotides

```
              (B) TYPE: nucleic acid
              (C) STRANDEDNESS:  single
              (D) TOPOLOGY: linear (ii) MOLECULE TYPE:  DNA (xi) SEQUENCE DESCRIPTION: SEQ ID NO: 124:

GCATTGAGCG GGTTDATCCA AGAAAGGACC CGG                                    33

(2) INFORMATION FOR SEQ ID NO:125:

(i) SEQUENCE CHARACTERISTICS:
              (A) LENGTH: 33 nucleotides
              (B) TYPE: nucleic acid
              (C) STRANDEDNESS:  single
              (D) TOPOLOGY: linear (ii) MOLECULE TYPE:  DNA (xi) SEQUENCE DESCRIPTION: SEQ ID NO: 125:

AGCAGTCTYG CGGGGGCACG CCCAARTCTC CAG                                    33

(2) INFORMATION FOR SEQ ID NO:126:

(i) SEQUENCE CHARACTERISTICS:
              (A) LENGTH: 33 nucleotides
              (B) TYPE: nucleic acid
              (C) STRANDEDNESS:  single
              (D) TOPOLOGY: linear (ii) MOLECULE TYPE:  DNA (xi) SEQUENCE DESCRIPTION: SEQ ID NO: 126:

ACAAGGCCTT TCGCGACCCA ACACTACTCG GCT                                    33

(2) INFORMATION FOR SEQ ID NO:127:

(i) SEQUENCE CHARACTERISTICS:
              (A) LENGTH: 33 nucleotides
              (B) TYPE: nucleic acid
              (C) STRANDEDNESS:  single
              (D) TOPOLOGY: linear (ii) MOLECULE TYPE:  DNA (xi) SEQUENCE DESCRIPTION: SEQ ID NO: 127:

GGGGCACTCG CAAGCACCCT ATCAGGCAGT ACC                                    33

(2) INFORMATION FOR SEQ ID NO:128:

(i) SEQUENCE CHARACTERISTICS:
              (A) LENGTH: 33 nucleotides
              (B) TYPE: nucleic acid
              (C) STRANDEDNESS:  single
              (D) TOPOLOGY: linear (ii) MOLECULE TYPE:  DNA (xi) SEQUENCE DESCRIPTION: SEQ ID NO: 128:

YGTGCTCATG RTGCACGGTC TACGAGACCT CCC                                    33

(2) INFORMATION FOR SEQ ID NO:129:

(i) SEQUENCE CHARACTERISTICS:
              (A) LENGTH: 33 nucleotides
              (B) TYPE: nucleic acid
              (C) STRANDEDNESS:  single
              (D) TOPOLOGY: linear
```

```
    (ii) MOLECULE TYPE:  DNA (xi) SEQUENCE DESCRIPTION: SEQ ID NO: 129:

GTTACGTTTG KTTYTTYTTT GRGGTTTRGG AWT                                33

(2) INFORMATION FOR SEQ ID NO:130:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 130:

CGGGAACTTR ACGTCCTGTG GGCGRCGGTT GGT                                33

(2) INFORMATION FOR SEQ ID NO:131:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 131:

CARGTAAACT CCACCRACGA TCTGRCCRCC RCC                                33

(2) INFORMATION FOR SEQ ID NO:132:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 132:

RCGCACACCC AAYCTRGGGC CCCTGCGCGG CAA                                33

(2) INFORMATION FOR SEQ ID NO:133:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 133:

AGGTTGCGAC CGCTCGGAAG TCTTYCTRGT CGC                                33

(2) INFORMATION FOR SEQ ID NO:134:

(i) SEQUENCE CHARACTERISTICS:
        (A) LENGTH: 33 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 134:
```

```
RCGHRCCTTG GGGATAGGCT GACGTCWACC TCG                                    33

(2) INFORMATION FOR SEQ ID NO:135:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 135:

RCGHRCCTTG GGGATAGGTT GTCGCCWTCC ACG                                    33

(2) INFORMATION FOR SEQ ID NO:136:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 136:

YCCRGGCTGR GCCCAGRYCC TRCCCTCGGR YYG                                    33

(2) INFORMATION FOR SEQ ID NO:137:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 137:

BSHRCCCTCR TTRCCRTAGA GGGGCCADGG RTA                                    33

(2) INFORMATION FOR SEQ ID NO:138:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 138:

GCCRCGGGGW GACAGGAGCC ATCCYGCCCA CCC                                    33

(2) INFORMATION FOR SEQ ID NO:139:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 139:

CCGGGGGTCY GTGGGGCCCC AYCTAGGCCG RGA                                    33

(2) INFORMATION FOR SEQ ID NO:140:
```

(i) SEQUENCE CHARACTERISTICS:
    (A) LENGTH: 33 nucleotides
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 140:

ATCGATGACC TTACCCAART TRCGCGACCT RCG        33

(2) INFORMATION FOR SEQ ID NO:141:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 141:

CCCCATGAGR TCGGCGAAGC CGCAYGTRAG GGT        33

(2) INFORMATION FOR SEQ ID NO:142:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 142:

GCCYCCWARR GGGGCGCCGA CGAGCGGWAT RTA        33

(2) INFORMATION FOR SEQ ID NO:143:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 143:

AACCCGGACR CCRTGYGCCA RGGCCCTGGC AGC        33

(2) INFORMATION FOR SEQ ID NO:144:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 144:

RTTCCCTGTT GCATAGTTCA CGCCGTCYTC CAG        33

(2) INFORMATION FOR SEQ ID NO:145:

(i) SEQUENCE CHARACTERISTICS:
        (A) LENGTH: 33 nucleotides
        (B) TYPE: nucleic acid -continued

```
        (C) STRANDEDNESS:  single
        (D) TOPOLOGY:  linear (ii) MOLECULE TYPE:  DNA (xi) SEQUENCE DESCRIPTION: SEQ ID NO: 145:

CARRAGGAAG AKAGAGAAAG AGCAACCRGG MAR                               33

(2) INFORMATION FOR SEQ ID NO:146:

(i) SEQUENCE CHARACTERISTICS:
        (A) LENGTH: 20 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 146:

AGGCATAGGA CCCGTGTCTT                                              20

(2) INFORMATION FOR SEQ ID NO:147:

(i) SEQUENCE CHARACTERISTICS:
        (A) LENGTH: 20 nucleotides
        (B) TYPE: nucleic acid
        (C) STRANDEDNESS:  single
        (D) TOPOLOGY: linear (ii) MOLECULE TYPE:  DNA (xi) SEQUENCE DESCRIPTION: SEQ ID NO: 147:

CTTCTTTGGA GAAAGTGGTG                                              20
```

HCV GENOMIC SEQUENCES FOR DIAGNOSTICS AND THERAPEUTICS

This application is a divisional, of application Ser. No. 08/221,653, filed Apr. 1, 1994, now U.S. Pat. No. 6,190,864 which is a continuation of application Ser. No. 07/881,528, filed May 8, 1992 now abandoned which is a continuation-in-part of U.S. Ser. No. 07/697,326 entitled "Polynucleotide Probes Useful for Screening for Hepatitis C Virus, filed May 8, 1991, now abandoned.

TECHNICAL FIELD

The invention relates to compositions and methods for the detection and treatment of hepatitis C virus, (HCV) infection, formerly referred to as blood-borne non-A, non-B hepatitis virus (NANBV) infection. More specifically, embodiments of the present invention feature compositions and methods for the detection of HCV, and for the development of vaccines for the prophylactic treatment of infections of HCV, and development of antibody products for conveying passive immunity to HCV.

BACKGROUND OF THE INVENTION

The prototype isolate of HCV was characterized in U.S. patent application Ser. No. 122,714 (See also EPO Publication No. 318,216). As used herein, the term "HCV" includes new isolates of the same viral species. The term "HCV-1" referred to in U.S. patent application Ser. No. 122,714.

HCV is a transmissible disease distinguishable from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). HCV was first identified in individuals who had received blood transfusions.

The demand for sensitive, specific methods for screening and identifying carriers of HCV and HCV contaminated blood or blood products is significant. Post-transfusion hepatitis (PTH) occurs in approximately 10% of transfused patients, and HCV accounts for up to 90% of these cases. The disease frequently progresses to chronic liver damage (25–55%).

Patient care as well as the prevention of transmission of HCV by blood and blood products or by close personal contact require reliable screening, diagnostic and prognostic tools to detect nucleic acids, antigens and antibodies related to HCV.

Information in this application suggests the HCV has several genotypes. That is, the genetic information of the HCV virus may not be totally identical for all HCV, but encompasses groups with differing genetic information.

Genetic information is stored in thread-like molecules of DNA and RNA. DNA consists of covalently linked chains of deoxyribonucleotides and RNA consists of covalently linked chains of ribonucleotides. Each nucleotide is characterized by one of four bases: adenine (A), guanine (G), thymine (T), and cytosine (C). The bases are complementary in the sense that, due to the orientation of functional groups, certain base pairs attract and bond to each other through hydrogen bonding and $\pi$-stacking interactions. Adenine in one strand of DNA pairs with thymine in an opposing complementary strand. Guanine in one strand of DNA pairs with cytosine in an opposing complementary strand. In RNA, the thymine base is replaced by uracil (U) which pairs with adenine in an opposing complementary strand. The genetic code of living organism is carried in the sequence of base pairs. Living cells interpret, transcribe and translate the information of nucleic acid to make proteins and peptides.

The HCV genome is comprised of a single positive strand of RNA. The HCV genome possesses a continuous, translational open reading frame (ORF) that encodes a polyprotein of about 3,000 amino acids. In the ORF, the structural protein(s) appear to be encoded in approximately the first quarter of the N-terminus region, with the majority of the polyprotein responsible for non-structural proteins.

The HCV polyprotein comprises, from the amino terminus to the carboxy terminus, the nucleocapsid protein (C), the envelope protein (E), and the non-structural proteins (NS) 1, 2 (b), 3, 4 (b), and 5.

HCV of differing genotypes may encode for proteins which present an altered response to host immune systems. HCV of differing genotypes may be difficult to detect by immuno diagnostic techniques and nucleic acid probe techniques which are not specifically directed to such genotype.

Definitions for selected terms used in the application are set forth below to facilitate an understanding of the invention. The term "corresponding" means homologous to or complementary to a particular sequence of nucleic acid. As between nucleic acids and peptides, corresponding refers to amino acids of a peptide in an order derived from the sequence of a nucleic acid or its complement.

The term "non-naturally occurring nucleic acid" refers to a portion of genomic nucleic acid, cDNA, semisynthetic nucleic acid, or synthetic origin nucleic acid which, by virtue of its origin or manipulation: (1) is not associated with all of a nucleic acid with which it is associated in nature, (2) is linked to a nucleic acid or other chemical agent other than that to which it is linked in nature, or (3) does not occur in nature.

Similarly the term, "a non-naturally occurring peptide" refers to a portion of a large naturally occurring peptide or protein, or semi-synthetic or synthetic peptide, which by virtue of its origin or manipulation (1) is not associated with all of a peptide with which it is associated in nature, (2) is linked to peptides, functional groups or chemical agents other than that to which it is linked in nature, or (3) does not occur in nature.

The term "primer" refers to a nucleic acid which is capable of initiating the synthesis of a larger nucleic acid when placed under appropriate conditions. The primer will be completely or substantially complementary to a region of the nucleic acid to be copied. Thus, under conditions conducive to hybridization, the primer will anneal to a complementary region of a larger nucleic acid. Upon addition of suitable reactants, the primer is extended by the polymerizing agent to form a copy of the larger nucleic acid.

The term "binding pair" refers to any pair of molecules which exhibit mutual affinity or binding capacity. For the purposes of the present application, the term "ligand" will refer to one molecule of the binding pair, and the term "antiligand" or "receptor" or "target" will refer to the opposite molecule of the binding pair. For example, with respect to nucleic acids, a binding pair may comprise two complementary nucleic acids. One of the nucleic acids may be designated the ligand and the other strand is designated the antiligand receptor or target. The designation of ligand or antiligand is a matter of arbitrary convenience. Other binding pairs comprise, by way of example, antigens and antibodies, drugs and drug receptor sites and enzymes and enzyme substrates, to name a few.

The term "label" refers to a molecular moiety capable of detection including, by way of example, without limitation, radioactive isotopes, enzymes, luminescent agents, precipitating agents, and dyes.

The term "support" includes conventional supports such as filters and membranes as well as retrievable supports which can be substantially dispersed within a medium and removed or separated from the medium by immobilization, filtering, partitioning, or the like. The term "support means" refers to supports capable of being associated to nucleic acids, peptides or antibodies by binding partners, or covalent or noncovalent linkages.

A number of HCV strains and isolates have been identified. When compared with the sequence of the original isolate derived from the USA ("HCV-1"; see Q.-L. Choo et al. (1989) *Science* 244:359–362, Q.-L. Choo et al. (1990) *Brit. Med. Bull.* 46:423–441, Q.-L. Choo et al., *Proc. Natl. Acad. Sci.* 88:2451–2455 (1991), and E.P.O. Patent Publication No. 318,216, cited supra), it was found that a Japanese isolate ("HCV J1") differed significantly in both nucleotide and polypeptide sequence within the NS3 and NS4 regions. This conclusion was later extended to the NS5 and envelope (E1/S and E2/NS1) regions (see K. Takeuchi et al., *J. Gen. Virol.* (1990) 71:3027–3033, Y. Kubo, *Nucl. Acids. Res.* (1989) 17:10367–10372, and K. Takeuchi et al., *Gene* (1990) 91:287–291). The former group of isolates, originally identified in the United States, is termed "Genotype I" throughout the present disclosure, while the latter group of isolates, initially identified in Japan, is termed "Genotype II" herein.

BRIEF DESCRIPTION OF THE INVENTION

The present invention features compositions of matter comprising nucleic acids and peptides corresponding to the HCV viral genome which define different genotypes. The present invention also features methods of using the compositions corresponding to sequences of the HCV viral genome which define different genotypes described herein.

A. Nucleic Acid Compositions

The nucleic acid of the present invention, corresponding to the HCV viral genome which define different genotypes, have utility as probes in nucleic acid hybridization assays, as primers for reactions involving the synthesis of nucleic acid, as binding partners for separating HCV viral nucleic acid from other constituents which may be present, and as anti-sense nucleic acid for preventing the transcription or translation of viral nucleic acid.

One embodiment of the present invention features a composition comprising a non-naturally occurring nucleic acid having a nucleic acid sequence of at least eight nucleotides corresponding to a non-HCV-1 nucleotide sequence of the hepatitis C viral genome. Preferably, the nucleotide sequence is selected from a sequence present in at least one region consisting of the NS5 region, envelope 1 region, 5'UT region, and the core region.

Preferably, with respect to sequences which correspond to the NS5 region, the sequence is selected from a sequence within a sequence numbered 2–22. The sequence numbered 1 corresponds to HCV-1. Sequences numbered 1–22 are defined in the Sequence Listing of the application.

Preferably, with respect to sequences corresponding to the envelope 1 region, the sequence is selected from a sequence within sequences numbered 24–32. Sequence No. 23 corresponds to HCV-1. Sequences numbered 23–32 are set forth in the Sequence Listing of the application.

Preferably, with respect to the sequences which correspond to the 5'UT regions, the sequence is selected from a sequence within sequences numbered 34–51. Sequence No. 33 corresponds to HCV-1. Sequence No. 33–51 are set forth in the Sequence Listing of this application.

Preferably, with respect to the sequences which correspond to the core region, the sequence is selected from a sequence within the sequences numbered 53–66. Sequence No. 52 corresponds to HCV-1. Sequences 52–66 are set forth in the Sequence Listing of this application.

The compositions of the present invention form hybridization products with nucleic acid corresponding to different genotypes of HCV.

HCV has at least five genotypes, which will be referred to in this application by the designations GI–GV. The first genotype, GI, is exemplified by sequences numbered 1–6, 23–25, 33–38 and 52–57. The second genotype, GII, is exemplified by the sequences numbered 7–12, 26–28, 39–45 and 58–64. The third genotype, GIII, is exemplified by sequences numbered 13–17, 32, 46–47 and 65–66. The fourth genotype, GIV, is exemplified by sequences numbered 20–22, and 29–31 and 48–49. The fifth genotype, GV, is exemplified by sequences numbered 18, 19, 50 and 51.

One embodiment of the present invention features compositions comprising a nucleic acid having a sequence corresponding to one or more sequences which exemplify a genotype of HCV.

B. Method of Forming a Hybridization Product

Embodiments of the present invention also feature a method of forming a hybridization product with nucleic acid having a sequence corresponding to HCV nucleic acid. One method comprises the steps of placing a non-naturally occurring nucleic acid having a non-HCV-1 sequence corresponding to HCV nucleic acid under conditions in which hybridization may occur. The non-naturally occurring nucleic acid is capable of forming a hybridization product with HCV nucleic acid, under hybridization conditions. The method further comprises the step of imposing hybridization conditions to form a hybridization product in the presence of nucleic acid corresponding to a region of the HCV genome.

The formation of a hybridization product has utility for detecting the presence of one or more genotypes of HCV. Preferably, the non-naturally occurring nucleic acid forms a hybridization product with nucleic acid of HCV in one or more regions comprising the NS5 region, envelope 1 region, 5'UT region and the core region. To detect the hybridization product, it is useful to associate the non-naturally occurring nucleic acid with a label. The formation of the hybridization product is detected by separating the hybridization product from labeled non-naturally occurring nucleic acid, which has not formed a hybridization product.

The formation of a hybridization product has utility as a means of separating one or more genotypes of HCV nucleic acid from other constituents potentially present. For such applications, it is useful to associate the non-naturally occurring nucleic acid with a support for separating the resultant hybridization product from the the other constituents.

Nucleic acid "sandwich assays" employ one nucleic acid associated with a label and a second nucleic acid associated with a support. An embodiment of the present invention features a sandwich assay comprising two nucleic acids, both have sequences which correspond to HCV nucleic acids; however, at least one non-naturally occurring nucleic acid has a sequence corresponding to non-HCV-1 HCV nucleic acid. At least one nucleic acid is capable of associating with a label, and the other is capable of associating with a support. The support associated non-naturally occurring nucleic acid is used to separate the hybridization products which include an HCV nucleic acid and the non-naturally occurring nucleic acid having a non-HCV-1 sequence.

One embodiment of the present invention features a method of detecting one or more genotypes of HCV. The method comprises the steps of placing a non-naturally occurring nucleic acid under conditions which hybridization may occur. The non-naturally occurring nucleic acid is capable of forming a hybridization product with nucleic acid from one or more-genotypes of HCV. The first genotype, GI, is exemplified by sequences numbered 1–6, 23–25, 33–38 and 52–57. The second genotype, GII, is exemplified by the sequences numbered 7–12, 26–28, 39–45 and 58–64. The third genotype, GIII, is exemplified by sequences numbered 13–17, 32, 46–47 and 65–66. The fourth genotype, GIV, is exemplified sequences numbered 20–22 and 29–31. The fifth genotype, GV, is exemplified by sequences numbered 18, 19, 50 and 51.

The hybridization product of HCV nucleic acid with a non-naturally occurring nucleic acid having non-HCV-1 sequence corresponding to sequences within the HCV genome has utility for priming a reaction for the synthesis of nucleic acid.

The hybridization product of HCV nucleic acid with a non-naturally occurring nucleic acid having a sequence corresponding to a particular genotype of HCV has utility for priming a reaction for the synthesis of nucleic acid of such genotype. In one embodiment, the synthesized nucleic acid is indicative of the presence of one or more genotypes of HCV.

The synthesis of nucleic acid may also facilitate cloning of the nucleic acid into expression vectors which synthesize viral proteins.

Embodiments of the present methods have utility as anti-sense agents for preventing the transcription or translation of viral nucleic acid. The formation of a hybridization product of a non-naturally occurring nucleic acid having sequences which correspond to a particular genotype of HCV genomic sequencing with HCV nucleic acid may block translation or transcription of such genotype. Therapeutic agents can be engineered to include all five genotypes for inclusivity.

C. Peptide and Antibody Composition

A further embodiment of the present invention features a composition of matter comprising a non-naturally occurring peptide of three or more amino acids corresponding to a nucleic acid having a non-HCV-1 sequence. Preferably, the non-HCV-1 sequence corresponds with a sequence within one or more regions consisting of the NS5 region, the envelope 1 region, the 5'UT region, and the core region.

Preferably, with respect to peptides corresponding to a nucleic acid having a non-HCV-1 sequence of the NS5 region, the sequence is within sequences numbered 2–22. The sequence numbered 1 corresponds to HCV-1. Sequences numbered 1–22 are set forth in the Sequence Listing.

Preferably, with respect to peptides corresponding to a nucleic acid having a non-HCV-1 sequence of the envelope 1 region, the sequence is within sequences numbered 24–32. The sequence numbered 23 corresponds to HCV-1. Sequences numbered 23–32 are set forth in the Sequence Listing.

Preferably, with respect to peptides corresponding to a nucleic acid having a non-HCV-1 sequence directed to the core region, the sequence is within sequences numbered 53–66. Sequence numbered 52 corresponds to HCV-1. Sequences numbered 52–66 are set forth in the Sequence Listing.

The further embodiment of the present invention features peptide compositions corresponding to nucleic acid sequences of a genotype of HCV. The first genotype, GI, is exemplified by sequences numbered 1–6, 23–25, 33–38 and 52–57. The second genotype, GII, is exemplified by the sequences numbered 7–12, 26–28, 39–45 and 58–64. The third genotype, GIII, is exemplified by sequences numbered 13–17, 32, 46–47 and 65–66. The fourth genotype, GIV, is exemplified sequences numbered 20–22, 29–31, 48 and 49. The fifth genotype, GV, is exemplified by sequences numbered 18, 19, 50 and 51.

The non-naturally occurring peptides of the present invention are useful as a component of a vaccine. The sequence information of the present invention permits the design of vaccines which are inclusive for all or some of the different genotypes of HCV. Directing a vaccine to a particular genotype allows prophylactic treatment to be tailored to maximize the protection to those agents likely to be encountered. Directing a vaccine to more than one genotype allows the vaccine to be more inclusive.

The peptide compositions are also useful for the development of specific antibodies to the HCV proteins. One embodiment of the present invention features as a composition of matter, an antibody to peptides corresponding to a non-HCV-1 sequence of the HCV genome. Preferably, the non-HCV-1 sequence is selected from the sequence within a region consisting of the NS5 region, the envelope 1 region, and the core region. There are no peptides associated with the untranslated 5'UT region.

Preferably, with respect to antibodies directed to peptides of the NS5 region, the peptide corresponds to a sequence within sequences numbered 2–22. Preferably, with respect to antibodies directed to a peptide corresponding to the envelope 1 region, the peptide corresponds to a sequence within sequences numbered 24–32. Preferably, with respect to the antibodies directed to peptides corresponding to the core region, the peptide corresponds to a sequence within sequences numbered 53–66.

Antibodies directed to peptides which reflect a particular genotype have utility for the detection of such genotypes of HCV and therapeutic agents.

One embodiment of the present invention features an antibody directed to a peptide corresponding to nucleic acid having sequences of a particular genotype. The first genotype, GI, is exemplified by sequences numbered 1–6, 23–25, 33–38 and 52–57. The second genotype, GII, is exemplified by the sequences numbered 7–12, 26–28, 39–45 and 58–64. The third genotype, GIII, is exemplified by sequences numbered 13–17, 32, 46–47 and 65–66. The fourth genotype, GIV, is exemplified sequences numbered 20–22, 29–31, 48 and 49. The fifth genotype, GV, is exemplified by sequences numbered 18, 19, 50 and 51.

Individuals skilled in the art will readily recognize that the compositions of the present invention can be packaged with instructions for use in the form of a kit for performing nucleic acid hybridizations or immunochemical reactions.

The present invention is further described in the following figures which illustrate sequences demonstrating genotypes of HCV. The sequences are designated by numerals 1–145, which numerals and sequences are consistent with the numerals and sequences set forth in the Sequence Listing. Sequences 146 and 147 facilitate the discussion of an assay which numerals and sequences are consistent with the numerals and sequences set forth in-the Sequence Listing.

BRIEF DESCRIPTION OF THE FIGURES AND SEQUENCE LISTING

FIG. 1 depicts schematically the genetic organization of HCV;

FIG. 2 sets forth nucleic acid sequences numbered 1–22 which sequences are derived from the NS5 region of the HCV viral genome;

FIG. 3 sets forth nucleic acid sequences numbered 23–32 which sequences are derived from the envelope 1 region of the HCV viral genome;

FIG. 4 sets forth nucleic acid sequences numbered 33–51 which sequences are derived from the 5'UT region of the HCV viral genome; and, FIG. 5 sets forth nucleic acid sequences numbered 52–66 which sequences are derived from the core region of the HCV viral genome.

The Sequence Listing sets forth the sequences of sequences numbered 1–147.

DETAILED DESCRIPTION OF THE INVENTION

The present invention will be described in detail as as nucleic acid having sequences corresponding to the HCV genome and related peptides and binding partners, for diagnostic and therapeutic applications.

The practice of the present invention will employ, unless otherwise indicated, conventional techniques of chemistry, molecular biology, microbiology, recombinant DNA, and immunology, which are within the skill of the art. Such techniques are explained fully in the literature. See e.g., Maniatis, Fitsch & Sambrook, Molecular Cloning; A Laboratory Manual (1982); DNA Cloning, Volumes I and I: (D. N Glover ed. 1985); Oligonucleotide Synthesis (M. J. Gait ed, 1984); Nucleic Acid Hybridization (B. D. Hames & S. J. Higgins eds. 1984); the series, Methods in Enzymology (Academic Press, Inc.), particularly Vol. 154 and Vol. 155 (Wu and Grossman, eds.).

The cDNA libraries are derived from nucleic acid sequences present in the plasma of an HCV-infected chimpanzee. The construction of one of these libraries, the "c" library (ATCC No. 40394), is described in PCT Pub. No. WO90/14436. The sequences of the library relevant to the present invention are set forth herein as sequence numbers 1, 23, 33 and 52.

Nucleic acids isolated or synthesized in accordance with features of the present invention are useful, by way of example without limitation as probes, primers, anti-sense genes and for developing expression systems for the synthesis of peptides corresponding to such sequences.

The nucleic acid sequences described define genotypes of HCV with respect to four regions of the viral genome. FIG. 1 depicts schematically the organization of HCV. The four regions of particular interest are the NS5 region, the envelope 1 region, the 5'UT region and the core region.

The sequences set forth in the present application as sequences numbered 1–22 suggest at least five genotypes in the NS5 region. Sequences numbered 1–22 are depicted in FIG. 2 as well as the Sequence Listing. Each sequence numbered 1–22 is derived from nucleic acid having 340 nucleotides from the NS5 region.

The five genotypes are defined by groupings of the sequences defined by sequence numbered 1–22. For convenience, in the present application, the different genotypes will be assigned roman numerals and the letter "G".

The first genotype (GI) is exemplified by sequences within sequences numbered 1–6. A second genotype (GII) is exemplified by sequences within sequences numbered 7–12. A third genotype (GIII) is exemplified by the sequences within sequences numbered 13–17. A fourth genotype (GIV) is exemplified by sequences within sequences numbered 20–22. A fifth genotype (GV) is exemplified by sequences within sequences numbered 18 and 19.

The sequences set forth in the present application as sequences numbered 23–32 suggest at least four genotypes in the envelope 1 region of HCV. Sequences numbered 23–32 are depicted in FIG. 3 as well as in the Sequence Listing. Each sequence numbered 23–32 is derived from nucleic acid having 100 nucleotides from the envelope 1 region.

A first envelope 1 genotype group (GI) is exemplified by the sequences within the sequences numbered 23–25. A second envelope 1 genotype (GII) region is exemplified by sequences within sequences numbered 26–28. A third envelope 1 genotype (GIII) is exemplified by the sequences within sequences numbered 32. A fourth envelope 1 genotype (GIV) is exemplified by the sequences within sequence numbered 29–31.

The sequences set forth in the present application as sequences numbered 33–51 suggest at least three genotypes in the 5'UT region of HCV. Sequences numbered 33–51 are depicted in FIG. 4 as well as in the Sequence Listing. Each sequence numbered 33–51 is derived from the nucleic acid having 252 nucleotides from the 5'UT region, although sequences 50 and 51 are somewhat shorter at approximately 180 nucleotides.

The first 5'UT genotype (GI) is exemplified by the sequences within sequences numbered 33–38. A second 5'UT genotype (GII) is exemplified by the sequences within sequences numbered 39–45. A third 5'UT genotype (GIII) is exemplified by the sequences within sequences numbered 46–47. A fourth 5'UT genotype (GIV) is exemplified by sequences within sequences humbered 48 and 49. A fifth 5'UT genotype (GV) is exemplified by sequences within sequences numbered 50 and 51.

The sequences numbered 48–62 suggest at least three genotypes in the core region of HCV. The sequences numbered 52–66 are depicted in FIG. 5 as well as in the Sequence Listing.

The first core region genotype (GI) is exemplified by the sequences within sequences numbered 52–57. The second core region genotype (GII) is exemplified by sequences within sequences numbered 58–64. The third core region genotype (GIII) is exemplified by sequences within sequences numbered 65 and 66. Sequences numbered 52–65 are comprised of 549 nucleotides. Sequence numbered 66 is comprised of 510 nucleotides.

The various genotypes described with respect to each region are consistent. That is, HCV having features of the first genotype with respect to the NS5 region will substantially conform to features of the first genotype of the envelope 1 region, the 5'UT region and the core region.

Nucleic acid isolated or synthesized in accordance with the sequences set forth in sequence numbers 1–66 are useful as probes, primers, capture ligands and anti-sense agents. As probes, primers, capture ligands and anti-sense agents, the nucleic acid wil normally comprise approximately eight or more nucleotides for specificity as well as the ability to form stable hybridization products.

Probes

A nucleic acid isolated or synthesized in accordance with a sequence defining a particular genotype of a region of the HCV genome can be used as a probe to detect such genotype or used in combination with other nucleic acid probes to detect substantially all genotypes of HCV.

With the sequence information set forth in the present application, sequences of eight or more nucleotides are identified which provide the desired inclusivity and exclusivity with respect to various genotypes within HCV, and extraneous nucleic acid sequences likely to be encountered during hybridization conditions.

Individuals skilled in the art will readily recognize that the nucleic acid sequences, for use as probes, can be provided with a label to facilitate detection of a hybridization product.

Capture Ligand

For use as a capture ligand, the nucleic acid selected in the manner described above with respect to probes, can be readily associated with supports. The manner in which nucleic acid is associated with supports is well known. Nucleic acid having sequences corresponding to a sequence within sequences numbered 1–66 have utility to separate viral nucleic acid of one genotype from the nucleic acid of HCV of a different genotype. Nucleic acid isolated or synthesized in accordance with sequences within sequences numbered 1–66, used in combinations, have utility to capture substantially all nucleic acid of all HCV genotypes.

Primers

Nucleic acid isolated or synthesized in accordance with the sequences described herein have utility as primers for the amplification of HCV sequences. With respect to polymerase chain reaction (PCR) techniques, nucleic acid sequences of eight or more nucleotides corresponding to one or more sequences of sequences numbered 1–66 have utility in conjunction with suitable enzymes and reagents to create copies of the viral nucleic acid. A plurality of primers having different sequences corresponding to more than one genotype can be used to create copies of viral nucleic acid for such genotypes.

The copies can be used in diagnostic assays to detect HCV virus. The copies can also be incorporated into cloning and expression vectors to generate polypeptides corresponding to the nucleic acid synthesized by PCR, as will be described in greater detail below.

Anti-sense

Nucleic acid isolated or synthesized in accordance with the sequences described herein have utility as anti-sense genes to prevent the expression of HCV.

Nucleic acid corresponding to a genotype of HCV is loaded into a suitable carrier such as a liposome for introduction into a cell infected with HCV. A nucleic acid having eight or more nucleotides is capable of binding to viral nucleic acid or viral messenger RNA. Preferably, the antisense nucleic acid is comprised of 30 or more nucleotides to provide necessary stability of a hybridization product of viral nucleic acid or viral messenger RNA. Methods for loading anti-sense nucleic acid is known in the art as exemplified by U.S. Pat. No. 4,241,046 issued Dec. 23, 1980 to Papahadjopoulos et al.

Peptide Synthesis

Nucleic acid isolated or synthesized in accordance with the sequences described herein have utility to generate peptides. The sequences exemplified by sequences numbered 1–32 and 52–66 can be cloned into suitable vectors or used to isolate nucleic acid. The isolated nucleic acid is combined with suitable DNA linkers and cloned into a suitable vector. The vector can be used to transform a suitable host organism such as E. coli and the peptide encoded by the sequences isolated.

Molecular cloning techniques are described in the text Molecular Cloning: A Laboratory Manual, Maniatis et al., Coldspring Harbor Laboratory (1982).

The isolated peptide has utility as an antigenic substance for the development of vaccines and antibodies directed to the particular genotype of HCV.

Vaccines and Antibodies

The peptide materials of the present invention have utility for the development of antibodies and vaccines.

The availability of cDNA sequences, or nucleotide sequences derived therefrom (including segments and modifications of the sequence), permits the construction of expression vectors encoding antigenically active regions of the peptide encoded in either strand. The antigenically active regions may be derived from the NS5 region, envelope 1 regions, and the core region.

Fragments encoding the desired peptides are derived from the cDNA clones using conventional restriction digestion or by synthetic methods, and are ligated into vectors which may, for example, contain portions of fusion sequences such as beta galactosidase or superoxide dismutase (SOD), preferably SOD. Methods and vectors which are useful for the production of polypeptides which contain fusion sequences of SOD are described in European Patent Office Publication number 0196056, published Oct. 1, 1986.

Any desired portion of the HCV cDNA containing an open reading frame, in either sense strand, can be obtained as a recombinant peptide, such as a mature or fusion protein; alternatively, a peptide encoded in the cDNA can be provided by chemical synthesis.

The DNA encoding the desired peptide, whether in fused or mature form, and whether or not containing a signal sequence to permit secretion, may be ligated into expression vectors suitable for any convenient host. Both eukaryotic and prokaryotic host systems are presently used in forming recombinant peptides. The peptide is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, Methods in Enzymology for a variety of methods for purifying proteins. Such peptides can be used as diagnostics, or those which give rise to neutralizing antibodies may be formulated into vaccines. Antibodies raised against these peptides can also be used as diagnostics, or for passive immunotherapy or for isolating and identifying HCV.

An antigenic region of a peptide is generally relatively small—typically 8 to 10 amino acids or less in length. Fragments of as few as 5 amino acids may characterize an antigenic region. These segments may correspond to NS5 region, envelope 1 region, and the core region of the HCV genome. The 5'UT region is not known to be translated. Accordingly, using the cDNAs of such regions, DNAs encoding short segments of HCV peptides corresponding to such regions can be expressed recombinantly either as fusion proteins, or as isolated peptides. In addition, short amino acid sequences can be conveniently obtained by chemical synthesis. In instances wherein the synthesized peptide is correctly configured so as to provide the correct epitope, but is too small to be immunogenic, the peptide may be linked to a suitable carrier.

A number of techniques for obtaining such linkage are known in the art, including the formation of disulfide linkages using N-succinimidyl-3-(2-pyridylthio)propionate (SPDP) and succinimidyl 4-(N-maleimido-methyl) cyclohexane-1-carboxylate (SMCC) obtained from Pierce Company, Rockford, Ill. (if the peptide lacks a sulfhydryl group, this can be provided by addition of a cysteine residue). These reagents create a disulfide linkage between themselves and peptide cysteine residues on one protein and an amide linkage through the epsilon-amino on a lysine, or other free amino group in the other. A variety of such disulfide/amide-forming agents are known. See, for example, *Immun Rev* (1982) 62:185. Other bifunctional coupling agents form a thioether rather than a disulfide linkage. Many of these thio-ether-forming agents are commercially available and include reactive esters of 6-maleimidocaprioc acid, 2-bromoacetic acid, 2-iodoacetic acid, 4-N-maleimido-methyl)cyclohexane-1-carboxylic acid, and the like. The carboxyl groups can be activated by combining them with succinimide or 1-hydroxyl-2 nitro-4-sulfonic acid, sodium salt. Additional methods of coupling antigens employs the rotavirus/"binding peptide" system described in EPO Pub. No. 259,149, the disclosure of which is incorporated herein by reference. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysacaharides, such as latex functionalized Sepharose, agarose, cellulose, cellulose beads and the like; polymeric amino acids, such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, tetanus toxoid, and other proteins well known to those skilled in the art.

Peptides comprising HCV amino acid sequences encoding at least one viral epitope derived from the NS5, envelope 1, and core region are useful immunological reagents. The 5'UT region is not known to be translated. For example, peptides comprising such truncated sequences can be used as reagents in an immunoassay. These peptides also are candidate subunit antigens in compositions for antiserum production or vaccines. While the truncated sequences can be produced by various known treatments of native viral protein, it is generally preferred to make synthetic or recombinant peptides comprising HCV sequence. Peptides comprising these truncated HCV sequences can be made up entirely of HCV sequences (one or more epitopes, either contiguous or noncontiguous), or HCV sequences and heterologous sequences in a fusion protein. Useful heterologous sequences include sequences that provide for secretion from a recombinant host, enhance the immunological reactivity of the HCV epitope(s), or facilitate the coupling of the polypeptide to an immunoassay support or a vaccine carrier. See, E.G., EPO Pub. No. 116,201; U.S. Pat. No. 4,722,840; EPO Pub. No. 259,149; U.S. Pat. No. 4,629,783.

The size of peptides comprising the truncated HCV sequences can vary widely, the minimum size being a sequence of sufficient size to provide an HCV epitope, while the maximum size is not critical. For convenience, the maximum size usually is not substantially greater than that required to provide the desired HCV epitopes and function (s) of the heterologous sequence, if any. Typically, the truncated HCV amino acid sequence will range from about 5 to about 100 amino acids in length. More typically, however, the HCV sequence will be a maximum of about 50 amino acids in length, preferably a maximum of about 30 amino acids. It is usually desirable to select HCV sequences of at least about 10, 12 or 15 amino acids, up to a maximum of about 20 or 2.5 amino acids.

HCV amino acid sequences comprising epitopes can be identified in a number of ways. For example, the entire protein sequence corresponding to each of the NS5, envelope 1, and core regions can be screened by preparing a series of short peptides that together span the entire protein sequence of such regions. By starting with, for example, peptides of approximately 100 amino acids, it would be routine to test each peptide for the presence of epitope(s) showing a desired reactivity, and then testing progressively smaller and overlapping fragments from an identified peptides of 100 amino acids to map the epitope of interest. Screening such peptides in an immunoassay is within the skill of the art. It is also known to carry out a computer analysis of a protein sequence to identify potential epitopes, and then prepare peptides comprising the identified regions for screening.

The immunogenicity of the epitopes of HCV may also be enhanced by preparing them in mammalian or yeast systems fused with or assembled with particle-forming proteins such as, for example, that associated with hepatitis B surface antigen. See, eg., U.S. Pat. No. 4,722,840. Constructs wherein the HCV epitope is linked directly to the particle-forming protein coding sequences produce hybrids which are immunogenic with respect to the HCV epitope. In addition, all of the vectors prepared include epitopes specific to HBV, having various degrees of immunogenicity, such as, for example, the pre-S peptide. Thus, particles constructed from particle forming protein which include HCV sequences are immunogenic with respect to HCVUand HBV.

Hepatitis surface antigen (HBSAg) has been shown to be formed and assembled into particles in *S. cerevisiae* (P. Valenzuela et al. (1982)), as well as in, for example, mammalian cells (P. Valenzuela et al. 1984)). The formation of such particles has been shown to enhance the immunogenicity of the monomer subunit. The constructs may also include the immunodominant epitope of HBSAg, comprising the 55 amino acids of the presurface (pre-S) region. Neurath et al. (1984). Constructs of the pre-S-HBSAg particle expressible in yeast are disclosed in EPO 174,444, published Mar. 19, 1986; hybrids including heterologous viral sequences for yeast expression are disclosed in EPO 175,261, published Mar. 26, 1966. These constructs may also be expressed in mammalian cells such as Chinese hamster ovary (CHO) cells using an SV40-dihydrofolate reductase vector (Michelle et al. (1984)).

In addition, portions of the particle-forming protein coding sequence may be replaced with codons encoding an HCV epitope. In this replacement, regions which are not required to mediate the aggregation of the units to form immunogenic particles in yeast of mammals can be deleted, thus eliminating additional HBV antigenic sites from competition with the HCV epitope.

Vaccines

Vaccines may be prepared from one or more immunogenic peptides derived from HCV. The observed homology between HCV and Flaviviruses provides information concerning the peptides which are likely to be most effective as vaccines, as well as the regions of the genome in which they are encoded.

Multivalent vaccines against HCV may be comprised of one or more epitopes from one or more proteins derived from the NS5, envelope 1, and core regions. In particular, vaccines are contemplated comprising one or more HCV proteins or subunit antigens derived from the NS5, envelope 1, and core regions. The 5'UT region is not known to be translated.

The preparation of vaccines which contain an immunogenic peptide as an active ingredient, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-theronyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1-2-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+ TDM+CWS) in a 2% squalene/Tween 80 emulsion. The effectiveness of an adjuvant may be determined by measuring the amount of antibodies directed against an immunogenic peptide containing an HCV antigenic sequence resulting from administration of this peptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0/5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like.

The examples below are provided for illustrative purposes and are not intended to limit the scope of the present invention.

I. Detection of HCV RNA from Serum

RNA was extracted from serum using guanidinium salt, phenol and chloroform according to the instructions of the kit manufacturer (RNAzol™ B kit, Cinna/Biotecx). Extracted RNA was precipitated with isopropanol and washed with ethanol. A total of 25 µl serum was processed for RNA isolation, and the purified RNA was resuspended in 5 µl diethyl pyrocarbonate treated water for subsequent cDNA synthesis.

II. cDNA Synthesis and Polymerase Chain Reaction (PCR) Amplification

Table 1 lists the sequence and position (with reference to HCV1) of all the PCR-primers and probes used in these examples. Letter designations for nucleotides are consistent with 37 C.F.R. §§1.821–1.825. Thus, the letters A, C, G, T, and U are used in the ordinary sense of adenine, cytosine, guanine, thymine, and uracil. The letter M means A or C; R means A or G; W means A or T/U; S means C or G; Y means C or T/U; K means G or TIU; V means A or C or G. not T/U; H means A or C or T/U, not G; D means A or G or T/U, not C; B means C or G or T/U, not A; N means (A or C or G or T/U) or (unknown or other). Table 1 is set forth below:

TABLE 1

| Seq. No. | Sequence (5'-3') | Nucleotide Position |
|---|---|---|
| 67 | CAAACGTAACACCAACCGRCGCCCACAGG | 374–402 |
| 68 | ACAGAYCCGCAKAGRTCCCCCACG | 1192–1169 |
| 69 | GCAACCTCGAGGTAGACGTCAGCCTATCCC | 509–538 |
| 70 | GCAACCTCGTGGAAGGCGACAACCTATCCC | 509–538 |
| 71 | GTCACCAATGATTGCCCTAACTCGAGTATT | 948–977 |
| 72 | GTCACGAACGACTGCTCCAACTCAAG | 948–973 |
| 73 | TGGACATGATCGCTGGWGCYCACTGGGG | 1375–1402 |
| 74 | TGGAYATGGTGGYGGGGCYCACTGGGG | 1375–1402 |
| 75 | ATGATGAACTGGTCVCCYAC | 1308–1327 |
| 76 | ACCTTVGCCCAGTTSCCCRCCATGGA | 1453–1428 |
| 77 | AACCCACTCTATGYCCGGYCAT | 205–226 |
| 78 | GAATCGCTGGGGTGACCG | 171–188 |
| 79 | CCATGAATCACTCCCCTGTGAGGAACTA | 30–57 |
| 80 | TTGCGGGGGCACGCCCAA | 244–227 |

For cDNA synthesis and PCR amplification, a protocol developed by Perkin-Elmer/Cetus (GeneAmp® RNA PCR kit) was used. Both random hexamer and primers with specific complementary sequences to HCV were employed to prime the reverse transcription (RT) reaction. All processes, except for adding and mixing reaction components, were performed in a thermal cycler (MJ Research, Inc.). The first strand cDNA synthesis reaction was inactivated at 99° C. for 5 min, and then cooled at 50° C. for 5 min before adding reaction components for subsequent amplification. After an initial 5 cycles of 97° C. for 1 min, 50° C. for 2 min, and 72° C. for 3 min, 30 cycles of 94° C. for 1 min, 55° C. for 2 min, and 72° C. for 3 min followed, and then a final 7 min of elongation at 72° C.

For the genotyping analysis, sequences 67 and 68 were used as primers in the PCR reaction. These primers amplify a segment corresponding to the core and envelope regions. After amplification, the reaction products were separated on an agarose gel and then transferred to a nylon membrane. The immobilized reaction products were allowed to hybridize with a $^{32}$P-labelled nucleic acid corresponding to either Genotype I (core or envelope 1) or Genotype II (core or envelope 1). Nucleic acid corresponding to Genotype 1 comprised sequences numbered 69 (core), 71 (envelope), and 73 (envelope). Nucleic acid corresponding to Genotype II comprised sequences numbered 70 (core), 72 (envelope), and 74 (envelope).

The Genotype I probes only hybridized to the product amplified from isolates which had Genotype I sequence. Similarly, Genotype II probes only hybridized to the product amplified from isolates which had Genotype II sequence.

In another experiment, PCR products were generated using sequences 79 and 80. The products were analyzed as described above except Sequence No. 73 was used to detect Genotype I, Sequence No. 74 was used to detect Genotype II, Sequence No. 77 (5'UT) was used to detect Genotype III, and Sequence No. 78 (5'UT) was used to detect Genotype IV. Each sequence hybridized in a genotype specific manner.

III. Detection of HCV GI-GIV Using a Sandwich Hybridization Assay for HCV RNA

An amplified solution phase nucleic acid sandwich hybridization assay format is described in this example. The assay format employs several nucleic acid probes to effect capture and detection. A capture probe nucleic acid is capable of associating a complementary probe bound to a solid support and HCV nucleic acid to effect capture. A detection probe nucleic acid has a first segment (A) that binds to HCV nucleic acid and a second segment (B) that hybridizes to a second amplifier nucleic acid. The amplifier nucleic acid has a first segment (B*) that hybridizes to segment (B) of the probe nucleic acid and also comprises fifteen iterations of a segment (C). Segment C of the amplifier nucleic acid is capable of hybridizing to three labeled nucleic acids.

Nucleic acid sequences which correspond to nucleotide sequences of the envelope 1 gene of Group I HCV isolates are set forth in sequences numbered 81–99. Table 2 sets forth the area of the HCV genome to which the nucleic acid sequences correspond and a preferred use of the sequences.

TABLE 2

| Probe Type | Sequence No. | Complement of Nucleotide Numbers |
| --- | --- | --- |
| Label | 81 | 879–911 |
| Label | 82 | 912–944 |
| Capture | 83 | 945–977 |
| Label | 84 | 978–1010 |
| Label | 85 | 1011–1043 |
| Label | 86 | 1044–1076 |
| Label | 87 | 1077–1109 |
| Capture | 88 | 1110–1142 |
| Label | 89 | 1143–1175 |
| Label | 90 | 1176–1208 |
| Label | 91 | 1209–1241 |
| Label | 92 | 1242=1274 |
| Capture | 93 | 1275–1307 |
| Label | 94 | 1308–1340 |
| Label | 95 | 1341–1373 |
| Label | 96 | 1374–1406 |
| Label | 97 | 1407–1439 |
| Capture | 98 | 1440–1472 |
| Label | 99 | 1473–1505 |

Nucleic acid sequences which correspond to nucleotide sequences of the envelope 1 gene of Group II HCV isolates are set forth in sequences 100–118. Table 3 sets forth the area of the HCV genome to which the nucleic acid corresponds and the preferred use of the sequences.

TABLE 3

| Probe Type | Sequence No. | Complement of Nucleotide Numbers |
| --- | --- | --- |
| Label | 100 | 879–911 |
| Label | 101 | 912–944 |
| Capture | 102 | 945–977 |
| Label | 103 | 978–1010 |
| Label | 104 | 1011–1043 |
| Label | 105 | 1044–1076 |
| Label | 106 | 1077–1109 |
| Capture | 107 | 1110–1142 |
| Label | 108 | 1143–1175 |
| Label | 109 | 1176–1208 |
| Label | 110 | 1209–1241 |

TABLE 3-continued

| Probe Type | Sequence No. | Complement of Nucleotide Numbers |
| --- | --- | --- |
| Label | 111 | 1242=1274 |
| Capture | 112 | 1275–1307 |
| Label | 113 | 1308–1340 |
| Label | 114 | 1341–1373 |
| Label | 115 | 1374–1406 |
| Label | 116 | 1407–1439 |
| Capture | 117 | 1440–1472 |
| Label | 118 | 1473–1505 |

Nucleic acid sequences which correspond to nucleotide sequences in the C gene and the 5'UT region are set forth in sequences 119–145. Table 4 identifies the sequence with a preferred use.

TABLE 4

| Probe Type | Sequence No. |
| --- | --- |
| Capture | 119 |
| Label | 120 |
| Label | 121 |
| Label | 122 |
| Capture | 123 |
| Label | 124 |
| Label | 125 |
| Label | 126 |
| Capture | 127 |
| Label | 128 |
| Label | 129 |
| Label | 130 |
| Capture | 131 |
| Label | 132 |
| Label | 133 |
| Label | 134 |
| Label | 135 |
| Capture | 136 |
| Label | 137 |
| Label | 138 |
| Label | 139 |
| Capture | 140 |
| Label | 141 |
| Label | 142 |
| Label | 143 |
| Capture | 144 |
| Label | 145 |

The detection and capture probe HCV-specific segments, and their respective names as used in this assay were as follows.

Capture sequences are sequences numbered 119–122 and 141–144.

Detection sequences are sequences numbered 119–140.

Each detection sequence contained, in addition to the sequences substantially complementary to the HCV sequences, a 5' extension (B) which extension (B) is complementary to a segment of the second amplifier nucleic acid. The extension (B) sequence is identified in the Sequence Listing as Sequence No. 146, and is reproduced below.

AGGCATAGGACCCGTGTCTT

Each capture sequence contained, in addition to the sequences substantially complementary to HCV sequences, a sequence complementary to DNA bound to a solid phase. The sequence complementary to DNA bound to a solid support was carried downstream from the capture sequence. The sequence complementary to the DNA bound to the support is set forth as Sequence No. 147 and is reproduced below.

CTTCTTTGGAGAAAGTGGTG

Microtiter plates were prepared as follows. White Microlite 1 Removawell strips (polystyrene microtiter plates, 96 wells/plate) were purchased from Dynatech Inc.

Each well was filled with 200 µl N HCl and incubated at room temperature for 15–20 min. The plates were then washed 4 times with 1×PBS and the wells aspirated to remove liquid. The wells were then filled with 200 µl N NaOH and incubated at room temperature for 15–20 min. The plates were again washed 4 times with 1×PBS and the wells aspirated to remove liquid.

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/mole. A 1 mg/ml solution of the polypeptide was mixed with 2M NaCl/1× PBS to a final concentration of 0.1 mg/ml (pH 6.0). A volume of 200 µl of this solution was added to each well. The plate was wrapped in plastic to prevent drying and incubated at 30° C. overnight. The plate was then washed 4 times with 1×PBS and the wells aspirated to remove liquid.

The following procedure was used to couple the nucleic acid, a complementary sequence to Sequence No. 147, to the plates, hereinafter referred to as immobilized nucleic acid. Synthesis of immobilized nucleic acid having a sequence complementary to Sequence No. 133 was described in EPA 883096976. A quantity of 20 mg disuccinimidyl suberate was dissolved in 300 µl dimethyl-formamide (DMF). A quantity of 26 $OD_{260}$ units of immobilized nucleic acid was added to 100 µl coupling buffer (50 mM sodium phosphate, pH 7.8). The coupling mixture was then added to the DSS-DMF solution and stirred with a magnetic stirrer for 30 min. An NAP-25 column was equilibrated with 10 mM sodium phosphate, pH 6.5. The coupling mixture DSS-DMF solution was added to 2 ml 10 mM sodium phosphate, pH 6.5, at 4° C. The mixture was vortexed to mix and loaded onto the equilibrated NAP-25 column. DSS-activated immobilized nucleic acid DNA was eluted from the column with 3.5 ml 10 mM sodium phosphate, pH 6.5. A quantity of 5.6 $OD_{260}$ units of eluted DSS-activated immobilized nucleic acid DNA was added to 1500 ml 50 mM sodium phosphate, pH 7.8. A volume of 50 µl of this solution was added to each well and the plates were incubated overnight. The plate was then washed 4 times with 1×PBS and the wells aspirated to remove liquid.

Final stripping of plates was accomplished as follows. A volume of 200 µl of 0.2N NaOH containing 0.5% (w/v) SDS was added to each well. The plate was wrapped in plastic and incubated at 65° C. for 60 min. The plate was then washed 4 times with 1×PBS and the wells aspirated to remove liquid. The stripped plate was stored with desiccant beads at 2–8° C.

Serum samples to be assayed were analyzed using PCR followed by sequence analysis to determine the genotype.

Sample preparation consisted of delivering 50 µl of the serum sample and 150 µl P-K Buffer (2 mg/ml proteinase K in 53 mM Tris-HCl, pH 8.0/0.6 M NaCl/0.06 M sodium citrate/8 mM EDTA, pH 8.0/1.3% SDS/16 µg/ml sonicated salmon sperm DNA/7% formamide/50 fmoles capture probes/160 fmoles detection probes) to each well. Plates were agitated to mix the contents in the well, covered and incubated for 16 hr at 62° C.

After a further 10 minute period at room temperature, the contents of each well were aspirated to remove all fluid, and the wells washed 2× with washing buffer (0.1% SDS/0.015 M NaCl/0.0015 M sodium citrate). The amplifier nucleic acid was then added to each well (50 µl of 0.7 fmole/µl solution in 0.48 M NaCl/0.048 M sodium citrate/0.1% SDS/0.5% "blocking reagent" (Boehringer Mannheim, catalog No. 1096 176)). After covering the plates and agitating to mix the contents in the wells, the plates were incubated for 30 min. at 52° C.

After a further 10 min period at room temperature, the wells were washed as described above.

Alkaline phosphatase label nucleic acid, disclosed in EP 883096976, was then added to each well (50 µl/well of 2.66 fmoles/µl). After incubation at 52° C. for 15 min., and 10 min. at room temperature, the wells were washed twice as above and then 3× with 0.015 M NaCl/0.0015 M sodium citrate.

An enzyme-triggered dioxetane (Schaap et al., Tet. Lett. (1987) 28:1159–1162 and EPA Pub. No. 0254051), obtained from Lumigen, Inc., was employed. A quantity of 50 µl Lumiphos 530 (Lumigen) was added to each well. The wells were tapped lightly so that the reagent would fall to the bottom and gently swirled to distribute the reagent evenly over the bottom. The wells were covered and incubated at 37° C. for 20–40 min.

Plates were then read on a Dynatech ML 1000 luminometer. Output was given as the full integral of the light produced during the reaction.

The assay positively detected each of the serum samples, regardless of genotype.

IV. Expression of the Polypeptide Encoded in Sequences Defined by Differing Genotypes HCV polypeptides encoded by a sequence within sequences 1–66 are expressed as a fusion polypeptide with superoxide dismutase (SOD). A cDNA carrying such sequences is subcloned into the expression vector pSODcf1 (Steimer et al. 1986)).

First, DNA isolated from pSODcf1 is treated with BamHI and EcoRI, and the following linker was ligated into the linear DNA created by the restriction enzymes:

```
5 GAT CCT GGA ATT CTG ATA AGA
     CCT TAA GAC TAT TTT AA 3
```

After cloning, the plasmid containing the insert is isolated.

Plasmid containing the insert is restricted with EcoRI. The HCV cDNA is ligated into this EcoRI linearized plasmid DNA. The DNA mixture is used to transform *E. coli* strain D1210 (Sadler et al. (1980)). Polypeptides are isolated on gels.

V. Antigenicity of Polypeptides

The antigenicity of polypeptides formed in Section IV is evaluated in the following manner. Polyethylene pins arranged on a block in an 8 12 array (Coselco Mimetopes, Victoria, Australia) are prepared by placing the pins in a bath (20% v/v piperidine in dimethylformamide (DMF)) for 30 minutes at room temperature. The pins are removed, washed in DMF for 5 minutes, then washed in methanol four times (2 min/wash). The pins are allowed to air dry for at least 10 minutes, then washed a final time in DMF (5 Min). 1-Hydroxybenzotriazole (HOBt, 367 mg) is dissolved in DMF (80 µL) for use in coupling Fmoc-protected polypeptides prepared in Section IV.

The protected amino acids are placed in micro-titer plate wells with HOBt, and the pin block placed over the plate, immersing the pins in the wells. The assembly is then sealed in a plastic bag and allowed to react at 25° C. for 18 hours to couple the first amino acids to the pins. The block is then removed, and the pins washed with DMF (2 min.), MeOH (4×2 min.), and again with DMF (2 min.) to clean and deprotect the bound amino acids. The procedure is repeated for each additional amino acid coupled, until all octamers are prepared.

The free N-termini are then acetylated to compensate for the free amide, as most of the epitopes are not found at the N-terminus and thus would not have the associated positive charge. Acetylation is accomplished by filling the wells of a microtiter plate with DMF/acetic anhydride/triethylamine (5:2:1 v/v/v) and allowing the pins to react in the wells for 90 minutes at 20° C. The pins are then washed with DMF (2 min.) and MeOH (4×2 min.), and air dried for at least 10 minutes.

The side chain protecting groups are removed by treating the pins with trifluoroacetic acid/phenol/dithioethane (95:2.5:1.5, v/v/v) in polypropylene bags for 4 hours at room temperature. The pins are then washed in dichloromethane (2×2 min.), 5% di-isopropylethylamine/dichloromethane (2×5 min.), dichloromethane. (5 min.), and air-dried for at least 10 minutes. The pins are then washed in water (2 min.), MeOH (18 hours), dried in vacuo, and stored in sealed plastic bags over silica gel. IV.B.15.b *Assay of Peptides.*

Octamer-bearing pins are treated by sonicating for 30 minutes in a disruption buffer (1% sodium dodecylsulfate, 0.1% 2-mercaptoethanol, 0.1 M NaH2PO4) at 60° C. The pins are then immersed several times in water (60° C.), followed by boiling MeOH (2 min.), and allowed to air dry.

The pins are then precoated for 1 hour at 25° C. in microtiter wells containing 200 µL blocking buffer (1% ovalbumin, 1% BSA, 0.1% Tween, and 0.05% NaN3 in PBS), with agitation. The pins are then immersed in microtiter wells containing 175 µL antisera obtained from human patients diagnosed as having HCV and allowed to incubate at 4° C. overnight. The formation of a complex between polyclonal antibodies of the serum and the polypeptide initiates that the peptides give rise to an immune response in vivo. Such peptides are candidates for the development of vaccines.

Thus, this invention has been described and illustrated. It will be apparent to those skilled in the art that many variations and modifications can be made without departing from the purview of the appended claims and without departing from the teaching and scope of the present invention.

What is claimed is:

1. A non-naturally occurring nucleic acid comprising a necleotide sequence of about 15 or more nucleotides wherein at least fifteen contiguous nucleotides are fully homologous or fully complementary to a nucleotide sequence within a hepatitis C viral genome, wherein said nucleotide sequence is selected from or within a sequence selected from the group consisting of SEQ ID NOs: 24–32, provided that said nucleotide sequence is within a hepatitis C viral genome which is not HCV-1, HCV-J1, HCV-J4, or HCV-J7, and wherein the nucleic acid is no longer than about 100 nucleotides.

2. A non-naturally occurring nucleic acid comprising a nucleotide sequence of about 24 or more nucleotides wherein at least twenty-four contiguous nucleotides are fully homologous or fully complementary to a nucleotide sequence within a hepatitis C viral genome, wherein said nucleotide sequence is selected from or within a sequence selected from the group consisting of SEQ ID NOs: 24–32, provided that said nucleotide sequence is within a hepatitis C viral genome which is not HCV-1, HCV-J1, HCV-J4, or HCV-J7, and wherein the nucleic acid is no longer than about 100 nucleonides.

3. A non-naturally occurring nucleic acid comprising a nucleotide sequence of about 24 or more nucleotides wherein at least fifteen contiguous nucleotides are fully homologous or fully complementary to a nucleotide sequence within a hepaitis C viral genome, wherein said nucleotide sequence is selected from the group consisting of or within a sequence selected from SEQ ID NOs: 35, 36, 38–45, 48, and 49, provided that said nucleotide sequence is within a hepatitis C viral genome which is not HCV-1, HCV-J1, HCV-J4, HCV-J7, and wherein the nucleic acid is no longer than about 252 nucleotides.

4. A non-naturally occurring nucleic acid comprising a nucleotide seqence of about 24 or more nucleotides wherein at least fifteen contiguous nucleotides are fully homologous or fully complementary to a nucleotide sequence with a hepatitis C viral genome, wherein said nucleotide sequence is selected from the group consisting of or within a sequence selected from SEQ ID NOs: 50 and 51, provided that said nucleotide sequence is within a hepatitis C viral genorme which is not HCV-1, HCV-J1, HCV-J4, HCV-J37, and wherein the nucleic acid is no longer than about 180 nucleotides.

5. A non-naturally occurring nucleic acid comprising a nucleotide sequence of about 24 or more nucleotides wherein at least twenty-four contiguous nucleotides are fully homologous or fully complementary to a nucleotide sequence within a hepatitis C viral genome, wherein said nucleotide sequence is selected from the group consisting of or within a sequence selected from SEQ ID NOs: 35, 36, 38–45, 48, and 49, provided that said nuclcotide sequence is within a hepatitis C viral genome which is not HCV-1, HCV-J1, HCV-J4, HCV-J7, and wherein the nucleic acid is no longer thin about 252 nucleotides.

6. A non-naturally occurring nucleic acid comprising a nucleotide sequence of about 24 or more nucleotides wherein at least twenty-four contiguous nucleotides are fully homologous or fully complementsy to a nucleotide sequence within a hepatitis C viral genome, wherein said nucleotide sequence is selected from the group consisting of or within a sequence selected from SEQ ID NOs: 50 and 51, provided that said nucleotide sequence is within a hepatitis C viral genome which is not HCV-1, HCV-J1, HCV-J4, HCV-J7, and wherein the nucleic acid is no longer than about 180 nucleotides.

7. The composition of any one of claims 1, 2, 3, 4, 5, or 6 wherein said non-naturally occurring nucleic acid is capable of priming a reaction for the synthesis of nucleic acid to form a nucleic acid having a nucleotide sequence fully homologous to or fully complementary to a sequence within the hepatitis C virus genome.

8. The composition of any one of claims 1, 2, 3, 4, 5, or 6 wherein said non-naturally occurring nucleic acid has label means for detecting a hybridization product.

9. The composition of any one of claims 1, 2, 3, 4, 5, or 6 wherein said non-naturally occurring nucleic acid has support means for separating a hybridization product from solution.

10. The composition of any one of claims 1, 2, 3, 4, 5, or 6 wherein said non-naturally occurring nucleic prevents the transcription or translation of viral nucleic acid.

11. The nucleic acid of any one of claims 3, 4, 5, or 6, wherein the nucleotide sequence is of about 30 or more nucleotides.

* * * * *